United States Patent
Look et al.

(10) Patent No.: US 9,000,027 B2
(45) Date of Patent: Apr. 7, 2015

(54) CHK1 SUPPRESSES A CASPASE-2 APOPTOTIC RESPONSE TO DNA DAMAGE THAT BYPASSES P53, BCL-2 AND CASPASE-3

(75) Inventors: A. Thomas Look, North Reading, MA (US); Samuel Sidi, New York, NY (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 929 days.

(21) Appl. No.: 12/866,133

(22) PCT Filed: Feb. 4, 2009

(86) PCT No.: PCT/US2009/000702
§ 371 (c)(1), (2), (4) Date: Nov. 9, 2010

(87) PCT Pub. No.: WO2009/099601
PCT Pub. Date: Aug. 13, 2009

(65) Prior Publication Data
US 2011/0054001 A1      Mar. 3, 2011

Related U.S. Application Data

(60) Provisional application No. 61/063,506, filed on Feb. 4, 2008.

(51) Int. Cl.
*A61K 31/407* (2006.01)
*A61P 35/00* (2006.01)
*C12Q 1/37* (2006.01)
*C12Q 1/68* (2006.01)
*G01N 33/574* (2006.01)
*A61K 49/00* (2006.01)

(52) U.S. Cl.
CPC .......... *G01N 33/574* (2013.01); *A61K 49/0008* (2013.01); *G01N 2333/4704* (2013.01); *G01N 2333/96413* (2013.01); *G01N 2800/52* (2013.01)

(58) Field of Classification Search
CPC .................. A61K 49/0008; G01N 2333/4704; G01N 2333/96413; G01N 2800/52; G01N 33/574
USPC ........................ 514/410, 19.3; 435/24, 6.18
See application file for complete search history.

(56) References Cited

U.S. PATENT DOCUMENTS

| 7,067,506 B2 | 6/2006 | Keegan et al. |
| 2002/0147145 A1 | 10/2002 | Mailand et al. |
| 2003/0069284 A1 | 4/2003 | Keegan et al. |

(Continued)

FOREIGN PATENT DOCUMENTS

WO    WO2004044154    *    5/2004

OTHER PUBLICATIONS

Samuel et al. abstract (Blood (ASH Annual Meeting Abstracts) 2006 108: Abstract 1432.*

(Continued)

*Primary Examiner* — Savitha Rao
(74) *Attorney, Agent, or Firm* — Wolf, Greenfield & Sacks, P.C.

(57) ABSTRACT

The invention describes methods that are useful for treating cancer by administering a Chk1 inhibitor which can induce apoptosis in p53-defective cells when combined with a chemotherapy and/or radiotherapy. Methods for screening candidates for a Chk1 inhibitor-based cancer treatment regimen are also described.

10 Claims, 47 Drawing Sheets

(56) References Cited

U.S. PATENT DOCUMENTS

| | | |
|---|---|---|
| 2004/0014765 A1 | 1/2004 | Boyle et al. |
| 2004/0092535 A1 | 5/2004 | Barsanti et al. |
| 2004/0191168 A1 | 9/2004 | Dent et al. |
| 2005/0043381 A1 | 2/2005 | Johnson et al. |
| 2005/0148643 A1 | 7/2005 | Rui et al. |
| 2005/0203101 A1 | 9/2005 | Barsanti et al. |
| 2005/0245525 A1 | 11/2005 | Keegan et al. |
| 2005/0256157 A1 | 11/2005 | Gesner et al. |
| 2007/0179161 A1 | 8/2007 | Parratt et al. |
| 2007/0185013 A1 | 8/2007 | Clark |
| 2007/0254879 A1 | 11/2007 | Arrington et al. |
| 2007/0275961 A1 | 11/2007 | Bower et al. |

OTHER PUBLICATIONS

Afshar et al., Radiation-induced caspase-8 mediates p53-independent apoptosis in glioma cells. Cancer Res. Apr. 15, 2006;66(8):4223-32.

Arienti et al., Checkpoint kinase inhibitors: SAR and radioprotective properties of a series of 2-arylbenzimidazoles. J Med Chem. Mar. 24, 2005;48(6):1873-85.

Bergeron et al., Defects in regulation of apoptosis in caspase-2-deficient mice. Genes Dev. May 1, 1998;12(9):1304-14.

Berghmans et al., tp53 mutant zebrafish develop malignant peripheral nerve sheath tumors. Proc Natl Acad Sci U S A. Jan. 11, 2005;102(2):407-12. Epub Jan. 3, 2005.

Berman et al., Zebrafish as a model for myelopoiesis during embryogenesis. Exp Hematol. Sep. 2005;33(9):997-1006.

Bernassola et al., The promyelocytic leukaemia protein tumour suppressor functions as a transcriptional regulator of p63. Oncogene. Oct. 20, 2005;24(46):6982-6.

Bernassola et al., Ubiquitin-dependent degradation of p73 is inhibited by PML. J Exp Med. Jun. 7, 2004;199(11):1545-57.

Bonzon et al., Caspase-2-induced apoptosis requires bid cleavage: a physiological role for bid in heat shock-induced death. Mol Biol Cell. May 2006;17(5):2150-7. Epub Feb. 22, 2006.

Bunz et al., Requirement for p53 and p21 to sustain G2 arrest after DNA damage. Science. Nov. 20, 1998;282(5393):1497-501.

Castedo et al., Cell death by mitotic catastrophe: a molecular definition. Oncogene. Apr. 12, 2004;23(16):2825-37.

Castedo et al., The cell cycle checkpoint kinase Chk2 is a negative regulator of mitotic catastrophe. Oncogene. May 27, 2004;23(25):4353-61.

Chan et al., Cooperative effects of genes controlling the G(2)/M checkpoint. Genes Dev. Jul. 1, 2000;14(13):1584-8.

Chen et al., Chk1 in the DNA damage response: conserved roles from yeasts to mammals. DNA Repair (Amst). Aug.-Sep. 2004;3(8-9):1025-32.

Chen et al., Human Chk1 expression is dispensable for somatic cell death and critical for sustaining G2 DNA damage checkpoint. Mol Cancer Ther. Jun. 2003;2(6):543-8.

Chen et al., Selective Chk1 inhibitors differentially sensitize p53-deficient cancer cells to cancer therapeutics. Int J Cancer. Dec. 15, 2006;119(12):2784-94.

Colell et al., GAPDH and autophagy preserve survival after apoptotic cytochrome c release in the absence of caspase activation. Cell. Jun. 1, 2007;129(5):983-97.

Collis et al,. Enhanced radiation and chemotherapy-mediated cell killing of human cancer cells by small inhibitory RNA silencing of DNA repair factors. Cancer Res. Apr. 1, 2003;63(7):1550-4.

Cuadrado et al., "ATR activation in response to ionizing radiation: still ATM territory". Cell Div. May 17, 2006;1(1):7.

Cuadrado et al., ATM regulates ATR chromatin loading in response to DNA double-strand breaks. J Exp Med. Feb. 20, 2006;203(2):297-303. Epub Feb. 6, 2006.

Eimon et al., Delineation of the cell-extrinsic apoptosis pathway in the zebrafish. Cell Death Differ. Oct. 2006;13(10):1619-30. Epub Aug. 4, 2006.

Fogarty et al., The Drosophila grapes gene is related to checkpoint gene chk1/rad27 and is required for late syncytial division fidelity. Curr Biol. Jun. 1, 1997;7(6):418-26.

Franken et al., Clonogenic assay of cells in vitro. Nat Protoc. 2006;1(5):2315-9.

Frenkel et al., Accentuated apoptosis in normally developing p53 knockout mouse embryos following genotoxic stress. Oncogene. May 6, 1999;18(18):2901-7.

Garber, New checkpoint blockers begin human trials. J Natl Cancer Inst. Jul. 20, 2005;97(14):1026-8.

Giraldez et al., MicroRNAs regulate brain morphogenesis in zebrafish. Science. May 6, 2005;308(5723):833-8. Epub Mar. 17, 2005.

Goldstein et al., The coordinate release of cytochrome c during apoptosis is rapid, complete and kinetically invariant. Nat Cell Biol. Mar. 2000;2(3):156-62.

Gong et al., The tyrosine kinase c-Abl regulates p73 in apoptotic response to cisplatin-induced DNA damage. Nature. Jun. 24, 1999;399(6738):806-9.

Hengartner, The biochemistry of apoptosis. Nature. Oct. 12, 2000;407(6805):770-6.

Hickson et al., Identification and characterization of a novel and specific inhibitor of the ataxia-telangiectasia mutated kinase ATM. Cancer Res. Dec. 15, 2004;64(24):9152-9.

Hsu et al., The pu.1 promoter drives myeloid gene expression in zebrafish. Blood. Sep. 1, 2004;104(5):1291-7. Epub Mar. 2, 2004.

Huang et al., CDK2-dependent phosphorylation of FOXO1 as an apoptotic response to DNA damage. Science. Oct. 13, 2006;314(5797):294-7.

Imamura et al., Molecular cloning and functional characterization of zebrafish ATM. Int J Biochem Cell Biol. May 2005;37(5):1105-16. Epub Jan. 7, 2005.

Inohara et al., Genes with homology to mammalian apoptosis regulators identified in zebrafish. Cell Death Differ. May 2000;7(5):509-10.

Ishii et al., Frequent co-alterations of TP53, p16/CDKN2A, p14ARF, PTEN tumor suppressor genes in human glioma cell lines. Brain Pathol. Jul. 1999;9(3):469-79.

Kasibhatla et al., DNA damaging agents induce expression of Fas ligand and subsequent apoptosis in T lymphocytes via the activation of NF-kappa B and AP-1. Mol Cell. Mar. 1998;1(4):543-51.

Kastan et al., Cell-cycle checkpoints and cancer. Nature. Nov. 18, 2004;432(7015):316-23.

Kawabe, G2 checkpoint abrogators as anticancer drugs. Mol Cancer Ther. Apr. 2004;3(4):513-9.

Kohn et al., The protein kinase C inhibitor Gö6976 is a potent inhibitor of DNA damage-induced S and G2 cell cycle checkpoints. Cancer Res. Jan. 1, 2003;63(1):31-5.

Kolesnick et al., Radiation and ceramide-induced apoptosis. Oncogene. Sep. 1, 2003;22(37):5897-906.

Kratz et al., Functional characterization of the Bcl-2 gene family in the zebrafish. Cell Death Differ. Oct. 2006;13(10):1631-40. Epub Aug. 4, 2006.

Lam et al., Chk1 is haploinsufficient for multiple functions critical to tumor suppression. Cancer Cell. Jul. 2004;6(1):45-59.

Langenau et al., Myc-induced T cell leukemia in transgenic zebrafish. Science. Feb. 7, 2003;299(5608):887-90.

Langenau et al., Suppression of apoptosis by bcl-2 overexpression in lymphoid cells of transgenic zebrafish. Blood. Apr. 15, 2005;105(8):3278-85. Epub Dec. 23, 2004.

Langheinrich et al., Zebrafish as a model organism for the identification and characterization of drugs and genes affecting p53 signaling. Curr Biol. Dec. 10, 2002;12(23):2023-8.

Lassus, Requirement for caspase-2 in stress-induced apoptosis before mitochondrial permeabilization. Science. Aug. 23, 2002;297(5585):1352-4.

Levesque et al., Defective p53 signaling in p53 wild-type tumors attenuates p21waf1 induction and cyclin B repression rendering them sensitive to Chk1 inhibitors that abrogate DNA damage-induced S and G2 arrest. Mol Cancer Ther. Feb. 2008;7(2):252-62.

Li et al., Activation of caspase-2 in apoptosis. J Biol Chem. Aug. 22, 1997;272(34):21010-7.

(56) References Cited

OTHER PUBLICATIONS

Li et al., Cytochrome c release and apoptosis induced by mitochondrial targeting of nuclear orphan receptor TR3. Science. Aug. 18, 2000;289(5482):1159-64.
Lin et al., Conversion of Bcl-2 from protector to killer by interaction with nuclear orphan receptor.
Nur77/TR3. Cell. Feb. 20, 2004;116(4):527-40.
Liu et al., Chk1 is an essential kinase that is regulated by Atr and required for the G(2)/M DNA damage checkpoint. Genes Dev. Jun. 15, 2000;14(12):1448-59.
Lowe et al., Intrinsic tumour suppression. Nature. Nov. 18, 2004;432(7015):307-15.
Moffat et al., A lentiviral RNAi library for human and mouse genes applied to an arrayed viral high-content screen. Cell. Mar. 24, 2006;124(6):1283-98.
Mukhopadhyay et al., RNA silencing of checkpoint regulators sensitizes p53-defective prostate cancer cells to chemotherapy while sparing normal cells. Cancer Res. Apr. 1, 2005;65(7):2872-81.
Nutt et al., Metabolic regulation of oocyte cell death through the CaMKII-mediated phosphorylation of caspase-2. Cell. Oct. 7, 2005;123(1):89-103.
Okada et al., Pathways of apoptotic and non-apoptotic death in tumour cells. Nat Rev Cancer. Aug. 2004;4(8):592-603.
Prudhomme, Novel checkpoint 1 inhibitors. Recent Pat Anticancer Drug Discov. Jan. 2006;1(1):55-68.
Pyati et al., Zebrafish as a powerful vertebrate model system for in vivo studies of cell death. Semin Cancer Biol. Apr. 2007;17(2):154-65. Epub Dec. 15, 2006.
Reinhardt et al., p53-deficient cells rely on ATM- and ATR-mediated checkpoint signaling through the p38MAPK/MK2 pathway for survival after DNA damage. Cancer Cell. Feb. 2007;11(2):175-89.
Rentzsch et al., Specific and conserved roles of TAp73 during zebrafish development. Gene. Dec. 24, 2003;323:19-30.
Rhodes et al., Interplay of pu.1 and gata1 determines myelo-erythroid progenitor cell fate in zebrafish. Dev Cell. Jan. 2005;8(1):97-108.
Roninson et al., If not apoptosis, then what? Treatment-induced senescence and mitotic catastrophe in tumor cells. Drug Resist Updat. Oct. 2001;4(5):303-13.
Roos et al., DNA damage-induced cell death by apoptosis. Trends Mol Med. Sep. 2006;12(9):440-50. Epub Aug. 8, 2006.
Shin et al., Caspase-2 primes cancer cells for TRAIL-mediated apoptosis by processing procaspase-8. EMBO J. Oct. 19, 2005;24(20):3532-42. Epub Sep. 29, 2005.
Sidi et al., Chk1 suppresses a caspase-2 apoptotic response to DNA damage that bypasses p53, Bcl-2, and caspase-3. Cell. May 30, 2008;133(5):864-77.
Sidi et al., Modifier genetics in zebrafish identify Chk1 and an associated survival pathway as targets for pharmacotherapy of MDS/AML with P53 mutations. Blood. Nov. 16, 2006;108(11):416A. Abstract 1432.
Stern et al., Small molecules that delay S phase suppress a zebrafish bmyb mutant. Nat Chem Biol. Dec. 2005;1(7):366-70.
Syljuasen et al., Inhibition of Chk1 by CEP-3891 accelerates mitotic nuclear fragmentation in response to ionizing Radiation. Cancer Res. Dec. 15, 2004;64(24):9035-40.
Syljuåsen et al., Inhibition of human Chk1 causes increased initiation of DNA replication, phosphorylation of ATR targets, and DNA breakage. Mol Cell Biol. May 2005;25(9):3553-62.
Tao et al., Chk1 inhibitors for novel cancer treatment. Anticancer Agents Med Chem. Jul. 2006;6(4):377-88.
Tinel et al., The PIDDosome, a protein complex implicated in activation of caspase-2 in response to genotoxic stress. Science. May 7, 2004;304(5672):843-6. Epub Apr. 8, 2004.
Troy et al., Caspase-2 redux. Cell Death Differ. Jan. 2003;10(1):101-7.
Tse et al., Targeting checkpoint kinase 1 in cancer therapeutics. Clin Cancer Res. Apr. 1, 2007;13(7):1955-60.
Tu et al., In situ trapping of activated initiator caspases reveals a role for caspase-2 in heat shock-induced apoptosis. Nat Cell Biol. Jan. 2006;8(1):72-7. Epub Dec. 18, 2005.
Urist et al., p73 induction after DNA damage is regulated by checkpoint kinases Chk1 and Chk2. Genes Dev. Dec. 15, 2004;18(24):3041-54.
Vousden et al., Live or let die: the cell's response to p53. Nat Rev Cancer. Aug. 2002;2(8):594-604.
Wagner et al., Caspase-2 can function upstream of bid cleavage in the TRAIL apoptosis pathway. J Biol Chem. Aug. 13, 2004;279(33):35047-52. Epub Jun. 1, 2004.
Wang et al., Chk1-mediated phosphorylation of FANCE is required for the Fanconi anemia/BRCA pathway. Mol Cell Biol. Apr. 2007;27(8):3098-108. Epub Feb. 12, 2007.
Westerfield et al., An on-line database for zebrafish development and genetics research. Semin Cell Dev Biol. Oct. 1997;8(5):477-88.
Wichmann et al., Ionizing radiation induces caspase-dependent but Chk2- and p53-independent cell death in *Drosophila melanogaster*. Proc Natl Acad Sci U S A. Jun. 27, 2006;103(26):9952-7. Epub Jun. 19, 2006.
Wyllie et al., Cell death: the significance of apoptosis. Int Rev Cytol. 1980;68:251-306.
Xiao et al., A novel mechanism of checkpoint abrogation conferred by Chk1 downregulation. Oncogene. Feb. 17, 2005;24(8):1403-11.
Yang et al., Targeted expression of human MYCN selectively causes pancreatic neuroendocrine tumors in transgenic zebrafish. Cancer Res. Oct. 15, 2004;64(20):7256-62.
Yount et al., Transcriptional activation of TRADD mediates p53-independent radiation-induced apoptosis of glioma cells. Oncogene. May 17, 2001;20(22):2826-35.
Yuan et al., p73 is regulated by tyrosine kinase c-Abl in the apoptotic response to DNA damage. Nature. Jun. 24, 1999;399(6738):814-7.
Zachos et al., Chk1-deficient tumour cells are viable but exhibit multiple checkpoint and survival defects. EMBO J. Feb. 3, 2003;22(3):713-23.
Zhivotovsky et al., Caspase-2 function in response to DNA damage. Biochem Biophys Res Commun. Jun. 10, 2005;331(3):859-67.
Zhou et al., Targeting the checkpoint kinases: chemosensitization versus chemoprotection. Nat Rev Cancer. Mar. 2004;4(3):216-25. Epub 1-10.
Zhou et al., The DNA damage response: putting checkpoints in perspective. Nature. Nov. 23, 2000;408(6811):433-9.
Gilley et al., One INK4 gene and no ARF at the Fugu equivalent of the human INK4A/ARF/INK4B tumour suppressor locus. Oncogene. 2001; 20:7447-7452.
Manzl, Lack of Chk1-suppressed alternative cell death pathway in murine cells. Eur. Molec. Biol. Org. Workshop Schedule. Mar. 10-14, 2011; 8 pages.

* cited by examiner

▽ = band3

⇓ = mpo/l-plastin

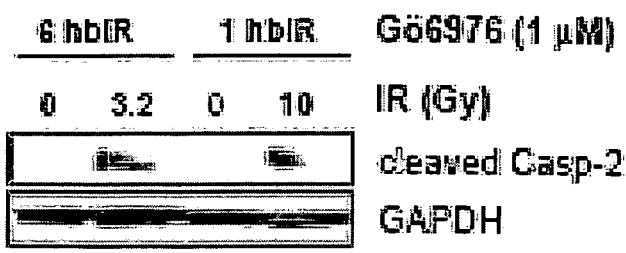
FIG. 7E
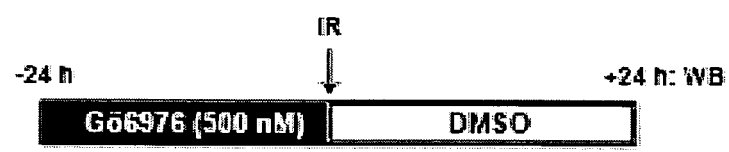
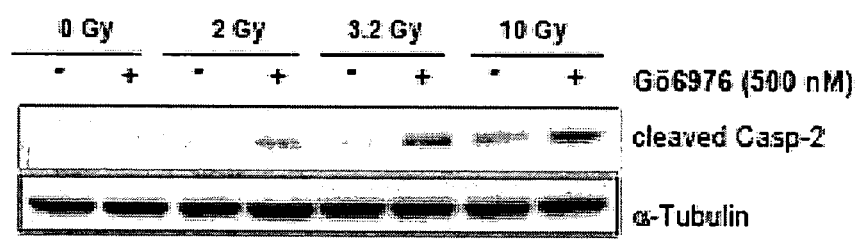
FIG. 7F
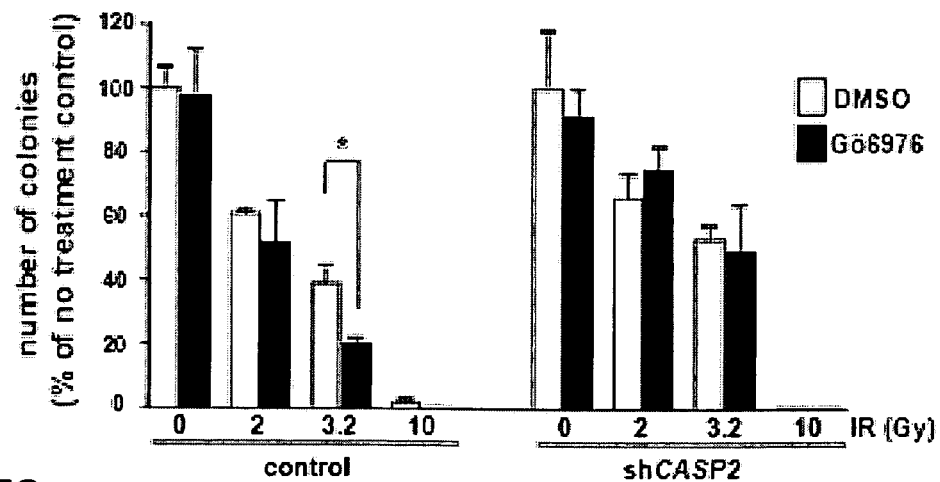
FIG. 7G

SEQUENCE LISTING

<160> NUMBER OF SEQ ID NOS: 31

<210> SEQ ID NO 1
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 1
aacgtacgcg gaatacttcg a                                              21

<210> SEQ ID NO 2
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 2
aagaagcagt cgcagtgaag a                                              21

<210> SEQ ID NO 3
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 3
gatatgttgc tcaccaccct t                                              21

<210> SEQ ID NO 4
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 4
ggagatgtct gaatactgca g                                              21

<210> SEQ ID NO 5
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 5
acacacttcc agctggcata t                                              21

<210> SEQ ID NO 6
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 6
ccgaaaggtg gcaacagaat t                                              21

<210> SEQ ID NO 7
<211> LENGTH: 21
<212> TYPE: DNA
<213> ORGANISM: Artificial sequence

```
<220> FEATURE:
<223> OTHER INFORMATION: Synthetic oligonucleotide

<400> SEQUENCE: 7
gcaagctgac cctgaagttc a                                              21

<210> SEQ ID NO 8
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 8
gtgacagctg tcaggagtat t                                              21

<210> SEQ ID NO 9
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 9
gcaacagtat ttcggtataa t                                              21

<210> SEQ ID NO 10
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 10
ctaagcacat tcaatccaat t                                              21

<210> SEQ ID NO 11
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 11
aggcacagcc attatgcaat cttcg                                          25

<210> SEQ ID NO 12
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 12
agccagagcg attatccaat gttcg                                          25

<210> SEQ ID NO 13
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 13
tccagcttcc tcagacatga tgctt                                          25
```

<210> SEQ ID NO 14
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 14
gaaaacggca ccacctggta aaaac                                                25

<210> SEQ ID NO 15
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 15
tgacatttct agtccttgct ccatc                                                25

<210> SEQ ID NO 16
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 16
gagtaaatcc attggagtag gtacc                                                25

<210> SEQ ID NO 17
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 17
tgcatacata ccgagtttca agtca                                                25

<210> SEQ ID NO 18
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 18
ggaatcaaaa acgctaccta gtttg                                                25

<210> SEQ ID NO 19
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 19
cgtgattatc agactgacct tagtg                                                25

<210> SEQ ID NO 20
<211> LENGTH: 25
<212> TYPE: DNA
<213> ORGANISM: Artificial sequence
<220> FEATURE:
<223> OTHER INFORMATION: Synthetic oligonucleotide

```
<400> SEQUENCE: 20
ctttaagtag cccatgctga accac                                         25

<210> SEQ ID NO 21
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 21
taataaagag gtctgacctg tgatg                                         25

<210> SEQ ID NO 22
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 22
cgctgaaacc ctgttgtacc tgtgg                                         25

<210> SEQ ID NO 23
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 23
accatactaa agtaccaacc atgag                                         25

<210> SEQ ID NO 24
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 24
cggtgaaagc ctcttctacc tctgg                                         25

<210> SEQ ID NO 25
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 25
acagggtttt aactcacagt agatc                                         25

<210> SEQ ID NO 26
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 26
gatggaaaaa cacacttacg gactg                                         25

<210> SEQ ID NO 27
```

```
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 27
aaccaagcat gactcttacc ctctg                                           25

<210> SEQ ID NO 28
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 28
aaagagtggc ataccgtcat tgaac                                           25

<210> SEQ ID NO 29
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 29
ggatgttgga caatccaccg caggg                                           25

<210> SEQ ID NO 30
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 30
taacgttacc aacctcgctc tttcg                                           25

<210> SEQ ID NO 31
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 31
gcgccattgc tttgcaagaa ttg                                             23
```

CHK1 SUPPRESSES A CASPASE-2 APOPTOTIC RESPONSE TO DNA DAMAGE THAT BYPASSES P53, BCL-2 AND CASPASE-3

RELATED APPLICATION

This application is a national stage filing under 35 U.S.C. §371 of international application PCT/US2009/000702, filed Feb. 4, 2009, which was published under PCT Article 21(2) in English, which claims the benefit under 35 U.S.C. §119(e) of U.S. Provisional Application Ser. No. 61/063,506, filed Feb. 4, 2008, the entire disclosures of which are incorporated herein by reference.

GOVERNMENT SUPPORT

This invention was made in part with government support under grant numbers HL-88664 and AI-47891 from the National Institute of Health. The United States government may have certain rights in this invention.

FIELD OF THE INVENTION

This invention relates to use of Chk1 inhibitors for cancer treatment and screening methods. More specifically, the invention describes methods for treating cancer by administering to a subject a Chk1 inhibitor used in conjunction with a chemotherapy and/or a radiotherapy. The invention is also useful for identifying candidates who will likely to respond to a cancer treatment regimen that includes a Chk1 inhibitor, and for monitoring effectiveness of such a treatment in a subject.

BACKGROUND OF THE INVENTION

The stress-inducible p53 protein acts as a central signal transduction node in the apoptotic response to DNA damage, mainly through its ability to transactivate intrinsic (mitochondrial) and extrinsic (death-receptor) pathway genes (Vousden and Lu, 2002). However, ample evidence supports the existence of p53-independent apoptotic responses to DNA damage. Most convincingly, in Drosophila and mouse p53 null embryos, several cell types undergo apoptosis in response to irradiation (IR), but with slower kinetics than p53$^{+/+}$ cells (Frenkel et al., 1999; Wichmann et al., 2006).

Candidate p53-independent apoptotic pathways have recently emerged from in vitro studies. ATM/ATR-activated ABL, Chk1 and Chk2, for instance, can upregulate p73 protein levels via diverse mechanisms in genotoxically challenged p53-deficient cells, restoring transactivation of PUMA and other proapoptotic p53 targets (Gong et al., 1999; Roos and Kaina, 2006; Urist et al., 2004; Yuan et al., 1999). p53-independent coupling of DNA damage to mitochondria can also occur through translocation of the nuclear orphan protein Nur77 into the cytosol, activation of nuclear and/or cytosolic caspase-2, or de novo ceramide synthesis by mitochondrial ceramide synthase, all converging on caspase-3 activation (Kolesnick and Fuks, 2003; Li et al., 2000; Lin et al., 2004; Zhivotovsky and Orrenius, 2005). Other p53-independent processes, involving MAPKs (e.g., SAPK/JNKs, p38) and the transcription factors E2F1, NF-κB and FOXO1, couple DNA damage to caspase-3 activation independently of mitochondria by upregulating death-receptor pathway genes including CASP8, whose product cleaves caspase-3 (Afshar et al., 2006; Huang et al., 2006; Kasibhatla et al., 1998; Yount et al., 2001). Whether any of the p53-independent apoptotic pathways also operate in vivo remains an active field of investigation.

Radioresistant/chemoresistant p53 mutant human cancer cell lines cultured in vitro can be induced to die after genotoxic stress upon pharmacologic or RNAi targeting of DNA damage-response (DDR) kinases involved in intra-S and/or G2/M checkpoint control, including ATM, ATR, Chk1, Chk2, Polo-like kinases (Plks), and as most recently shown, the p38/MAPK-activated kinase MAPKAPK2 (MK-2) (Bunz et al., 1998; Castedo et al., 2004a; Chan et al., 2000; Chen et al., 2003; Collis et al., 2003; Reinhardt et al., 2007; Roninson et al., 2001; Zhou and Bartek, 2004). Interestingly, such treatments might spare cells endowed with wild-type p53, presumably because their intact G1 checkpoint enables them to repair and thus survive DNA damage (Chen et al., 2006; Mukhopadhyay et al., 2005; Reinhardt et al., 2007). Although the observed sensitization of, and selectivity for, p53 mutant cells is at the root of anticancer strategies that target DDR kinases, none of these concepts have been rigorously tested in vivo in an animal model (Garber, 2005; Kastan and Bartek, 2004; Kawabe, 2004; Zhou and Elledge, 2000). Furthermore, the p53-independent cell death program triggered by DDR kinase inactivation remains elusive, with contradictory results as to the involvement of certain caspases and Bcl-2 family members in the regulation of apoptotic or reproductive cell death (i.e., 'mitotic catastrophe'; see, for example, Castedo et al., 2004a).

SUMMARY OF THE INVENTION

To accelerate the discovery of physiologic p53-independent DDRs, we generated p53 mutant zebrafish lines for use in whole organism-based modifier genetic screens (Berghmans et al., 2005). Zebrafish faithfully recapitulate mammalian intrinsic and extrinsic apoptotic signaling (Eimon et al., 2006; Inohara and Nunez, 2000; Kratz et al., 2006; Pyati et al., 2006). The zebrafish p53$^{M214K}$ allele (or p53$^{e7}$, for mutation in exon 7) affects a conserved amino acid residue within a region of the DNA-binding domain corresponding to a mutational hotspot in human cancer, producing a transactivation-dead p53 variant. Homozygosity for p53$^{e7}$ recapitulates key traits associated with p53 deficiency in mammalian systems, including a strong tumor-prone phenotype, lack of G1 checkpoint function and widespread cellular radioresistance (Berghmans et al., 2005).

Here we identify chk1 as a loss-of-function suppressor of p53$^{e7/e7}$-based radioresistance, thus validating the DDR kinase-targeting concept in vivo. Through epistasis analyses, we find that the underlying cell death mechanism differs from the p53-independent processes previously identified in vitro. Indeed, rather than restoring caspase-3 activation downstream of defective p53, Chk1 depletion activates an ATM/ATR-caspase-2 axis that bypasses the mitochondrial and death-receptor pathways. We show that this 'Chk1-suppressed' pathway is conserved in p53-deficient and BCL2-overexpressing human tumor cells, providing a mechanistic rationale the use of Chk1 inhibitors in cancer therapy.

The present invention, thus, is based on a newly identified apoptotic pathway that is distinct from the classic mitochondria-mediated "intrinsic" pathway and the Death Receptor-mediated "extrinsic" pathway. This new pathway involves caspase-2 and is triggered by genomic stress (e.g., DNA damage) provided that Chk1 activity is also compromised. Based on these findings, the invention provides various aspects relevant to cancer therapy.

The present invention provides, inter alia, screening methods that are useful for identifying cancer patients who may benefit from a treatment regimen that incorporates a Chk1 inhibitor in addition to a genotoxic therapy, such as a chemotherapy and a radiotherapy. One aspect of the invention is directed to methods for determining whether a subject having a cancer is a candidate for a Chk1 inhibitor-based cancer therapy. Thus, the methods comprise contacting cancer cells of the subject with a Chk1 inhibitor, in conjunction with a genotoxic stress, and then determining caspase-2 activation in the cancer cells. If there is caspase-2 activation in the cancer cells, then the subject is identified as a candidate for a Chk1 inhibitor-based cancer treatment regimen.

In some embodiments of this aspect of the invention, the cancer cells are contacted with the Chk1 inhibitor, in conjunction with a genotoxic stress, in vivo. In some cases, caspase-2 activation is determined by comparing a first level of caspase-2 activity determined in the cancer cells after the cancer cells are contacted with the Chk1 inhibitor, in conjunction with the genotoxic stress to a second level of caspase-2 activity determined in control cells. If the first level of caspase-2 activity is greater than the second level of caspase-2 activity, then there is caspase-2 activation. In some embodiments, the control cells are HeLa cells, Jurkat cells, HCT116 colon carcinoma cells, SAOS2 osteosarcoma, the MDA-MB-435 breast cancer line, or LN-428 glioblastoma cells. In other embodiments, the control cells are a sample of cancer cells obtained from the subject before contacting in vivo the cancer cells with the Chk1 inhibitor in conjunction with a genotoxic stress. In any of these embodiments, the genotoxic stress may include a chemotherapy, a radiotherapy or combination thereof.

In further embodiments, the cancer cells are a first sample of cancer cells obtained from the subject and contacted with the Chk1 inhibitor, in conjunction with a genotoxic stress, ex vivo or in vitro. In some circumstances, the caspase-2 activation is determined by comparing a first level of caspase-2 activity determined in the first sample of cancer cells after the first sample of cancer cells is contacted with the Chk1 inhibitor, in conjunction with the genotoxic stress to a second level of caspase-2 activity in determined in control cells. If the first level of caspase-2 activity is found to be greater than the second level of caspase-2 activity, then there is caspase-2 activation. In some embodiments, the control cells are HeLa cells, Jurkat cells, HCT116 colon carcinoma cells, SAOS2 osteosarcoma, the MDA-MB-435 breast cancer line, or LN-428 glioblastoma cells. In yet other embodiments, the control cells are a second sample of cancer cells obtained from the subject and not contacted with the Chk1 inhibitor.

According to a further aspect of the invention, methods for determining a course of cancer treatment regimen are provided. In some embodiments of this aspect, the methods comprise administering a Chk1 inhibitor to a subject having a cancer, in conjunction with a chemotherapy and/or radiotherapy, and determining caspase-2 activation in a biopsy sample obtained from the subject. If the biopsy sample indicates caspase-2 activation, a treatment regimen including a Chk1 inhibitor is continued; however, if the biopsy sample indicates no caspase-2 activation, a Chk1 inhibitor is excluded from a treatment regimen.

In yet other aspects of the invention, the methods comprise identifying a subject having a cancer with an abnormal p53 genotype based on an analysis of a biopsy sample obtained from the subject. If the biopsy sample indicates an abnormal p53 genotype, a treatment regimen including a Chk1 inhibitor is continued; and if the biopsy sample indicates a normal p53 genotype, a Chk1 inhibitor is excluded from a treatment regimen.

A further aspect of the invention provides methods for monitoring effectiveness of a Chk1 inhibitor-based cancer treatment regimen in a subject. The methods comprise obtaining a biopsy sample containing a cancer cell from a subject having a cancer following a treatment with a Chk1 inhibitor, in conjunction with a chemotherapy and/or radiotherapy, and determining caspase-2 activation in the sample. Greater caspase-2 activity in the sample relative to caspase-2 activity in a control sample indicates an effective Chk1 inhibitor-based cancer treatment regimen. A number of cell lines may be used as control, including but not limited to Hela cells, Jurkat cells, HCT116 colon carcinoma cells, SAOS2 osteosarcoma, the MDA-MB-435 breast cancer cells, and LN-428 glioblastoma cells.

According to another aspect of the invention, various methods that combine screening and treatment of cancer are provided. In some embodiments, the invention provides methods for treating a cancer in a subject, comprising determining a p53 genotype in a biopsy sample obtained from a subject having a cancer, wherein if the biopsy sample indicates a defective p53 genotype, then administering to the subject a Chk1 inhibitor, in conjunction with a chemotherapy and/or a radiotherapy, in an amount effective to treat the cancer.

In other embodiments, the methods for treating a cancer in a subject comprise determining caspase-2 activation in a cancer cell contacted with a Chk1 inhibitor, in conjunction with a genotoxic stress, the cancer cell being obtained from the subject, wherein if caspase-2 activation is present, then administering to the subject a Chk1 inhibitor, in conjunction with a chemotherapy and/or a radiotherapy, in an amount effective to treat the cancer.

Further aspects of the invention include methods for treating a cancer in a subject, comprising obtaining cancer cells from a subject having the cancer, subjecting a first sample of the cancer cells to a genotoxic stress in conjunction with contacting the first sample of cells with a Chk1 inhibitor, subjecting a second sample of the cancer cells to the genotoxic stress, wherein the second sample of cancer cells is not treated with a Chk1 inhibitor, determining relative caspase-2 activity in the first and second samples, wherein greater caspase-2 activity in the first sample relative to the second test sample indicates an effective response of the cancer cells to the Chk1 inhibitor, and if the effective response is present, then administering a Chk1 inhibitor to the subject, in conjunction with a chemotherapy and/or a radiotherapy, in an amount effective to treat the cancer.

In yet further aspects, the methods comprise determining a p53 genotype in a first cancer cell obtained from the cancer, determining caspase-2 activation in a second cancer cell contacted with a Chk1 inhibitor, in conjunction with a genotoxic stress, the second cancer cell being obtained from the cancer, wherein if the first cancer cell has a defective p53 genotype and the second cancer cell has caspase-2 activation, then administering to the subject a Chk1 inhibitor, in conjunction with a chemotherapy and/or a radiotherapy, in an amount effective to treat the cancer.

The methods of the invention also include administering a Chk1 inhibitor to the subject, in conjunction with a chemotherapy and/or a radiotherapy, in an amount effective to treat cancer, where the subject is selected on a basis of a biomarker indicative of responsiveness to the Chk1 inhibitor. In some cases, the biomarker is caspase-2 activation in a cancer cell of the subject when the cancer cell is contacted with a Chk1 inhibitor in conjunction with a genotoxic stress, a defective p53 genotype, or combination thereof.

The methods for treating cancer in a subject according to the invention further include monitoring effectiveness of the Chk1 inhibitor. Here, caspase-2 activation in a cancer cell in response to the Chk1 inhibitor in conjunction with a chemotherapy and/or a radiotherapy, indicates an effective cancer treatment.

DETAILED DESCRIPTION OF THE INVENTION

Figure 1A:
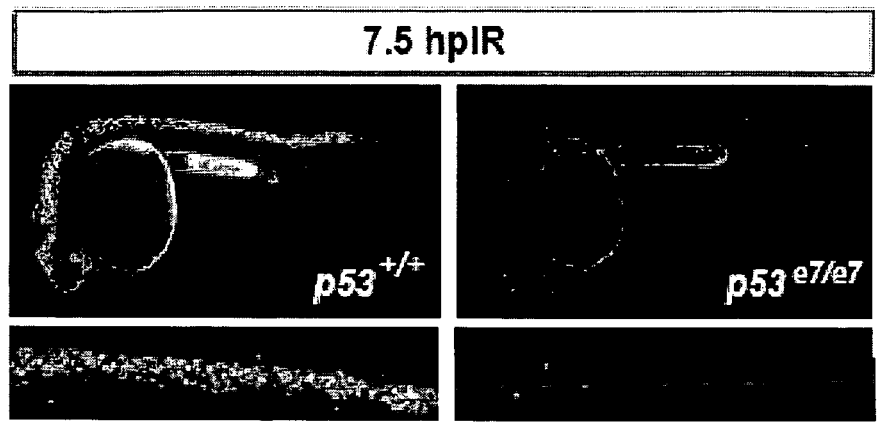
FIG. 1 provides panels of fluorescence images and a graph showing AO positivity. A morpholino screen identifies chk1 as a loss-of-function suppressor of $p53^{e7/e7}$-associated radioresistance. (A) Live embryos of the indicated genotypes stained with AO at 7.5 hpIR (12.5 Gy). Anterior, left. Note the complete absence of AO labeling in the brain and spinal cord of the irradiated p53 mutant. (B) MO screen for loss-of-function suppressors of $p53^{e7/e7}$-associated radioresistance. Noninjected and 1 cell-stage MO-injected embryos were irradiated at 18 hpf (12.5 Gy). AO uptake by cells was quantified by analyzing images of whole embryos photographed live at 7.5 hpIR (y-axis) (images as in FIG. 1C). Injected MOs are indicated along the x axis. Bars also indicate the genetic background used for injections (light gray, $p53^{+/+}$; dark gray, $p53^{e7/e7}$). AO staining was quantified in ≥8 embryos per knockdown, with 50 or more embryos scored per knockdown (except †, >1000); ‡, embryos showed developmental defects. All data are reported as means+/−SEM. Statistical significance versus the noninjected $p53^{e7/e7}$ response: *P<0.05; P<0.005; *P<0.0005; ns, not significant (two-tailed Student's t-test). (C) Fluorescence images of AO-labeled, live p53 mutants injected with indicated MOs and representative of the phenotypes quantified in FIG. 1B.

The present invention is based in part on the finding that a Chk1 inhibitor, when used in conjunction with an agent that causes genotoxic stress to a cell, can selectively inhibit cancer cells, provided that the cancer cells contain one or more mutation(s) in p53 or one or more gene(s) that are functionally linked to the p53 signaling pathway such that p53-mediated signal transduction is impaired. It has been surprisingly discovered that activation of caspase-2 can act as a biomarker for this process.

As used herein, a "Chk1 inhibitor" is an agent that has an effect of suppressing or inhibiting Chk1 activity, either directly or indirectly. Thus, a Chk1 inhibitor may act upon the Chk1 protein itself, for instance by binding to and blocking the kinase activity, or alternatively it may inhibit an upstream or downstream effector (e.g., a substrate) along the Chk1-based signal transduction pathway, such that a net effect is that Chk1 activity is suppressed. A preferred Chk1 inhibitor is selective. A selective Chk1 inhibitor can preferentially inhibit Chk1 activity but have no or little effect on the activity of related kinases at a certain concentration range.

A number of Chk1 inhibitors have been identified. Some of the known Chk1 inhibitors are reviewed, for example, in the article by Prudhomme entitled *Novel Checkpoint 1 Inhibitors* (Recent Patents on Anti-Cancer Drug Discovery, 2006, 1, 55-68 55). See also U.S. Pat. No. 7,067,506 (Keegan et al.) issued on Jun. 27, 2006; U.S. Patent Applications published as: 20070275961 entitled Triazolo' 1, 5-A ! Pyrimidines and Their Use in Medicine; 20070254879 entitled Inhibitors of checkpoint kinases; 20070185013 entitled Use of chk1 inhibitors to control cell proliferation; 20070179161 entitled Pyrazolopyrimidine compounds and their use in medicine; 20050256157 entitled Combination therapy with CHK1 inhibitors; 20050245525 entitled Compounds useful for inhibiting CHK1; 20050203101 entitled Benzimidazole quinolinones and uses thereof; 20050148643 entitled Carbamate compositions and methods for modulating the activity of the CHK1 enzyme; 20050043381 entitled Aminopyrazole compounds; 20040191168 entitled Tumor cell killing by cell cycle checkpoint abrogation combined with Inhibition of the classical mitogen activated protein (map) kinase pathway; 20040092535 entitled Benzimidazole quinolinones and uses thereof; 20040014765 entitled Chk-1 inhibitors; 20030069284 entitled Compounds useful for inhibiting Chk1; 20020147145 entitled Materials and methods relating to the degradation of Cdc25A in response to DNA damage.

When cells are contacted with a Chk1 inhibitor, in conjunction with an agent that can cause genotoxic stress, e.g., DNA damage, cell death can occur in cells that are abnormally susceptible to an inhibitor of checkpoint control (e.g., cancer cells), but not in normal cells (e.g., healthy cells). Without being bound to a particular theory of underlying mechanisms, it is thought that the selective killing of cancer cells occurs via caspase-dependant apoptosis.

The term "contact" or "contacting" as used herein shall mean contacting a cell, in vivo, ex vivo or in vitro, with an agent (e.g., compound and/or any physiochemical treatment) so as to effectuate a biological response in the cell. For example, a biopsy sample may be obtained from a subject having a cancer, and the biopsy sample (e.g., cancer cells) may be subjected to a genotoxic stress, such as radiation, in vivo, ex vivo or in vitro. Similarly, the biopsy sample may be subjected to a compound, such as a Chk1 inhibitor, in vivo, ex vivo or in vitro.

As used herein, "in conjunction with" shall broadly mean "used together or concurrently," and it is not meant to be limiting to a simultaneous treatment with two or more agents. Thus, "a Chk1 inhibitor in conjunction with a genotoxic stress" refers to the use of the Chk1 inhibitor together with a genotoxic stress such that the effect of the Chk1 inhibitor overlaps with that of the genotoxic stress, where the former may be given before the latter, or vice versa. In some embodiments of the present invention, a Chk1 inhibitor may be contacted with a cell simultaneously with a genotoxic treatment of the cell. In other embodiments, a Chk1 inhibitor and a genotoxic treatment are given separately but within a proximity in time close enough such that the effects are concurrent at least in part. Suitable timing of each treatment can depend, for example in the case of a chemical agent, on the pharmacokinetic characteristics of the agent. It should be appreciated that a Chk1 inhibitor treatment thus may precede a genotoxic stress, follow a genotoxic stress, or be at the same time as a genotoxic stress.

As used herein, "genotoxic" agents are agents that cause DNA damage. DNA damage can be induced by drugs or radiation. Genotoxic agents include, but are not limited to: ultra violet (UV) light, ionizing radiation (IR), radiomimetic drugs, platins such as cisplatin, oxaliplatin, and carboplatin, hydroxyureas, PARP inhibitors, taxanes such as taxol and taxotere, capecitabine, gemcitabine, among others. Thus, "genotoxic stress" refers to exposure of a cell to one or more of such agents that cause DNA damage in the cell. In a context of cancer therapy, genotoxic treatments are chemotherapy and radiotherapy, or combination thereof.

It is generally understood that radiation and most chemotherapeutic agents are therapeutically beneficial because they take advantage of inappropriate tumor cell proliferation. Cellular processes, such as DNA damage repair and cell cycle checkpoints, protect tumor cells from the toxic effects of physical and chemical agents. Treatments that modulate the underlying molecular mechanisms of cell cycle progression and resistance to DNA damage can potentiate tumor cell killing and enhance the therapeutic index of existing therapies.

Many anti-cancer chemotherapeutic agents act by disrupting DNA metabolism. Because these processes are shared by both normal and tumor cells, and because the maintenance of DNA integrity is essential to cell viability, anticancer drugs have the lowest therapeutic index of any drug class. By identifying and inhibiting cellular processes that tumor cells rely upon, the effectiveness of radiation and chemotherapy treatment regimens can be enhanced.

A "subject" is a vertebrate animal, preferably a mammal, more preferably a human. Thus a subject according to the invention includes, but is not limited to a rodent, dog, cat, horse, cow, pig, sheep, goat, chicken, primate, e.g., monkey.

A "subject having a cancer" is a subject that has detectable cancerous cells. Cancerous cells refer to tumors or neoplasms, including growths of tissue cells wherein multiplication of cells is uncontrolled and progressive. In some cases such growths are benign, but others are termed "malignant" and can lead to death of the animal. Malignant neoplasms are distinguished from benign growths in that, in addition to exhibiting aggressive cellular proliferation, can invade surrounding tissues and metastasize. Moreover, malignant neoplasms are characterized by showing a greater loss of differentiation (greater "dedifferentiation") and organization relative to one another and surrounding tissues. This property is called "anaplasia."

The invention contemplates use of a Chk1 inhibitor for a wide array of cancers or cancer-related conditions. Neoplasms relevant to the present invention also include solid tumors, i.e., carcinomas and sarcomas. Carcinomas include malignant neoplasms derived from epithelial cells which infiltrate (i.e., invade) surrounding tissues and give rise to metastases. Adenocarcinomas are carcinomas derived from glandular tissue, or from tissues that form recognizable glandular structures. Another broad category of cancers includes sarcomas, which are tumors whose cells are embedded in a fibrillar or homogeneous substance, like embryonic connective tissue. The invention also enables treatment of cancers of the myeloid or lymphoid systems, including leukemias, lymphomas, and other cancers that typically are not present as a tumor mass, but are distributed in the vascular or lymphoreticular systems. The present invention is particularly deemed useful for the treatment of cancer. Cancers as referred to herein include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one or more of the above-identified conditions.

Chk1 activity has been reported to be associated with various forms of cancer. Thus, the invention is particularly suitable for screening and/or treating these forms of cancer that are implicated to involve a Chk1-dependent signaling. Examples of Chk1-associated cancers include but are not limited to: adult and pediatric oncology, growth of solid tumors/malignancies, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer (including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma), gastrointestinal cancers (including stomach cancer, colon cancer, colorectal cancer, and polyps associated with colorectal neoplasia), pancreatic cancer, liver cancer, urological cancers (including bladder cancer, such as primary superficial bladder tumors, invasive transitional cell carcinoma of the bladder, and muscle-invasive bladder cancer), prostate cancer, malignancies of the female genital tract (including ovarian carcinoma, primary peritoneal epithelial neoplasms, cervical carcinoma, uterine endometrial cancers, vaginal cancer, cancer of the vulva, uterine cancer and solid tumors in the ovarian follicle), malignancies of the male genital tract (including testicular cancer and penile cancer), kidney cancer (including renal cell carcinoma, brain cancer (including intrinsic brain tumors, neuroblastoma, astrocytic brain tumors, gliomas, and metastatic tumor cell invasion in the central nervous system), bone cancers (including osteomas and osteosarcomas), skin cancers (including malignant melanoma, tumor progression of human skin keratinocytes, and squamous cell cancer), thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

Given the great diversity of cancer genetics and pathogenesis, it is desirable to identify and to direct a patient to a treatment regimen that is tailored to the specific presentation of the disease and/or genetic background of the patient. Determining a course of cancer treatment regimen therefore involves the determination of suitable therapies for the patient based on the pathological presentation of the patient, e.g., optimization of treatment strategy. Pathological presentation includes genotypic and phenotypic characteristics of the disease, the progression or the stage of the disease, prognosis, medical history of the patient, and so on, as well as secondary complication(s) the patient may experience.

It is difficult to predict from standard clinical and pathologic features the clinical course of cancer. However, it is very important in the treatment of cancer to select and implement an appropriate combination of therapeutic approaches. The available methods for designing strategies for treating cancer patients are complex and time consuming. The wide range of cancer subgroups and variations in disease progression limit the predictive ability of the healthcare professional. In addition, continuing development of novel treatment strategies and therapeutics will result in the addition of more variables to the already complex decision-making process involving matching the cancer patient with a treatment regimen that is appropriate and optimized for the cancer stage, tumor growth rate, and other factors central to the individual patient's prognosis. Because of the critical importance of selecting appropriate treatment regimens for cancer patients, the development of guidelines for treatment selection is of key interest to those in the medical community and their patients. Thus, there presently is a need for objective, reproducible, and sensitive methods for diagnosing cancer, predicting cancer patient prognosis and outcome, and selecting and monitoring optimal treatment regimens.

To this end, the present invention is particularly useful in screening for a candidate (e.g., subject) who can benefit from a Chk1 inhibitor-based cancer treatment. A "Chk1-based cancer treatment" refers to a cancer treatment that incorporates a Chk1 inhibitor as part of cancer therapy. As such, the ability to screen a candidate subject for a particular treatment for cancer provides a means of personalizing a cancer treatment regimen.

According to the invention described herein, screening is performed based upon one or more biomarkers that indicate the sensitivity of cancer cells to Chk1 inhibitor-based cancer treatment. The term "biomarker" refers to a biological indicator (e.g., genotypic and phenotypic). As described in further detail elsewhere herein, biomarkers that indicate whether a particular cancer or cancer cells from a subject are likely to respond to a Chk1 inhibitor-based cancer treatment include p53 mutation and caspase-2 activation. For example, an abnormal p53 genotype is indicative of responsiveness of cancer cells to a Chk1 inhibitor when used in conjunction with a genotoxic stress, which will likely induce apoptosis in the cancer cells. In addition, it has been surprisingly found, as disclosed herein, that caspase-2 activation in response to a Chk1 inhibitor in conjunction with a genotoxic stress serves as a useful biomarker for purposes of determining whether a cancer cell (or subject with a cancer) will be sensitive to a Chk1 inhibitor in conjunction with a genotoxic stress. The presence of an abnormal p53 genotype and an increased activity of caspase-2 in response to Chk1 inhibitor in conjunction with a genotoxic stress may be used independently or in combination to assess whether a particular individual may benefit from a Chk1 inhibitor-based cancer treatment.

Approximately 50% of human cancers are reported to involve one or more mutations in the p53 allele. There are numerous potential loci implicated in cancer, a mutation of which may result in malignancy. In some circumstances, the presence of a specific p53 mutation may already been known or suspected based on family history, for example. However, in other situations, it may require sequencing of the complete p53 allele to determine the presence or the exact locus of mutation(s) in a cancer cell, which may be both time consuming and costly.

As noted above, a candidate may be screened, as an alternative biomarker, on the basis of caspase-2 activation in response to a Chk1 inhibitor in conjunction with a genotoxic stress. Like many other members of the caspase family of proteases, caspase-2 is synthesized as a precursor of approximately 48-49 kDa. Activation of caspase-2 involves proteolytic cleavage of the pro-caspase-2 into at least two smaller fragments, including a fragment of approximately 19 kDa. This processing (e.g., cleavage) of pro-caspase-2 into smaller caspase-2 fragments correlates with caspase-2 activity, indicating that the processed form of caspase-2 represents the enzymatically active form of caspase-2 (See, for example, Li et al., 1997, J. Biol. Chem. 272: 21010-17). In HeLa cells grown in culture, for example, pro-caspase-2 (unprocessed, inactive form) is detectable by Western blotting, but active caspase-2 (processed or cleaved form) is not easily detectable when cells are proliferating. However, when apoptosis is induced in these cells by TNFα, for instance, the pro-caspase-2 gradually decreases in levels as cleaved fragments of caspase-2 concurrently increase. The latter fragments are easily detectable by Western blotting when about 10% of the total cells undergo apoptosis, as determined by trypan blue exclusion. Thus, relative levels of apoptosis correlate with increased levels of cleaved (e.g., processed) caspase-2, and concomitantly a decrease in pro-caspase-2. As shown in more detail in Example herein, in HeLa cells, caspase-2 cleavage is readily detectable at 24 hours following genotoxic stress (e.g., irradiation) in the presence of a Chk1 inhibitor. According to the invention, caspase-2 activation in response to a Chk1 inhibitor treatment in conjunction with a genotoxic stress predicts whether the cancer will respond to such a treatment. As used herein, caspase-2 activation means that higher levels of cleaved (e.g., processed) caspase-2 are present as compared to the level in control cells. For determining caspase-2 activation, relative activities of caspase-2 are assayed. What may serve as a suitable control will depend on the type of experimental setting and availability of suitable control sample(s). However, preferred control cells are cells of the same origin as a test sample. If grown in culture (e.g., in vitro), test cells and control cells are preferably grown under the same culture conditions. If a sample is a biopsy sample (e.g., ex vivo), a test sample and a control sample are preferably collected at the same time and maintained under the same conditions until use. In some cases, this may be determined by comparing the level of caspase-2 activity in a cancer cell to a value expected for normal cells or expected for Chk1 sensitive cancer cells. This also may be determined by comparing the caspase-2 activity of a cancer cell to the caspase-2 activity in control cells. The control cells can be normal cells, cancer cells that are not sensitive to Chk1 inhibitor based treatment, cancer cells that are sensitive to Chk1 inhibitor based treatment, cells that have been treated with a Chk1 inhibitor in conjunction with geotoxic stress, etc. The control cells may be from a cell bank or may be the subjects own cells, including the subjects cancer cells not treated with a Chk1 inhibitor in conjunction with genotoxic stress. The level of caspase-2 activity can be detected in a variety of ways. In some embodiments, for example, it is detected visually, such as in a Western blot or an immunoblot. As shown in the examples, control cells have barely detectable levels of caspase-2 activity and the treated cells show clear bands indicating an increase in activity. The level of activity can also be determined by quantifying the amount of caspase-2 present in a sample by any number of methods well known to those of ordinary skill in the art, including, but not limited to, measuring the amount of caspase-2 in a band from a gel, measuring the amount of radioactivity based on labeled antibodies to caspase-2 and pro-caspase-2, or measuring the amount of cleavage of a caspase-2 substrate cause by a sample containing caspase-2. In such instances, the treated cells can have a level of caspase-2 activity that is 20%, 30%, 40%, 50%, 75%, 100%, 200%, 500% or more than the level in the control.

In some embodiments of the invention, response to a Chk1 inhibitor in conjunction with a genotoxic stress is determined by assaying for detectable caspase-2 activity in a biological sample of a cancer, following in vivo Chk1 inhibitor/genotoxic stress treatment of the subject. In other embodiments, response to a Chk1 inhibitor in conjunction with a genotoxic stress is determined by assaying for detectable caspase-2 activity in a biological sample of a cancer before treating the subject. In this embodiment, a cancer sample is first obtained from the subject and then subjected to a Chk1 inhibitor/genotoxic stress in vitro. Thus, screening of a candidate for a Chk1 inhibitor-based cancer treatment may be performed in vitro, ex vivo or in vivo.

As discussed above, in vitro screening may involve a sample of cells obtained from a subject having or suspected of having a cancer and subsequently grown in culture. In some embodiments of the invention, cell lysates and/or DNA may be prepared from the cultured cells and processed for appropriate assays. For example, a biological sample form a subject believed to have cancer is obtained and grown in culture. Methods of growing and maintaining primary human cells are well known in the art. For determining caspase-2 activation, the cultured cells can be divided into four experimental samples, including the following conditions: with and without exposure to a genotoxic stress, and for each of those samples, divide further for testing with and without contacting with a Chk1 inhibitor. Accordingly, Sample 1 is contacted with both the genotoxic agent and the Chk1 inhibitor; Sample 2 is contacted with the genotoxic agent alone; Sample 3 is contacted with the Chk1 inhibitor alone; and finally, Sample 4 is subjected to neither and serves as a double negative control. For each of the experimental samples, caspase-2 activity is measured by one or more methods with which the art is familiar. Examples of these methods include but are not limited to: in vitro protease assays; protein immunoblot using an antibody that recognizes the full length as well as the truncated (processed) form of caspase-2; dimerization assays; immunoprecipitation using an activation-specific antibody (e.g., conformation-specific antibody) for caspase-2, followed by immunoblotting for detection; immunocytochemical analysis of native cells using activation-specific caspase-2 antibody (e.g., conformation-specific antibody) and so on. An increase in caspase-2 activation as determined by any of the methods listed above, which, for example, is indicated by an increase in the cleaved caspase-2 level and a concurrent decrease in pro-caspase-2 level, in the presence of both a Chk1 inhibitor and a genotoxic stress, but not either one alone, indicates that the cells are responsive to the Chk1-based treatment.

Ex vivo screening involves a tissue sample or a cell sample collected from a subject having or suspected of having a cancer, and the sample is maintained in a suitable physiological condition (e.g., a balanced buffer) as to maintain viability. The sample is divided into at least four experimental conditions as described above. Virtually the same methods listed for the in vitro screening methods can be applied to determine caspase-2 activation using ex vivo samples. Ex vivo screening may be particularly suitable for analyzing a biopsy sample of a structurally defined tumor.

In certain circumstances, a subject already receiving a genotoxic therapy, e.g., a chemotherapy and/or a radiotherapy as part of conventional cancer treatment regime, may be determined to be a good candidate for receiving a Chk1 inhibitor. In these situations, a physician may, notwithstanding the patient has not been screened for responsiveness to a Chk1 inhibitor, nevertheless decide to administer a Chk1 inhibitor and then monitor the effect of the Chk1 inhibitor in conjunction with the genotoxic therapy. In such a case, screening is thus performed essentially in vivo, and the patient's response to the treatment should help determine whether the Chk1 inhibitor-based cancer treatment is beneficial. It should be noted that an amount of a Chk1 inhibitor effective to induce selective killing of cancer cells when treated together with a genotoxic stress, is not toxic to otherwise healthy cells. Therefore, in vivo screening may be a practical strategy in situations where a patient is already receiving or about to undergo a series of a chemotherapy and/or radiotherapy, particularly as part of pre-operative treatment.

More preferably, to examine the effect of the Chk1-based therapy, a biopsy sample is collected from the patient receiving both the Chk1 inhibitor and the genotoxic stress, and caspase-2 activation is determined using one or more of the methods described above. As a reference, cell lysates prepared from control cells may be used. Examples of suitable control cells include but are not limited to: HeLa cells, Jurkat cells, HCT116 colon carcinoma cells, SAOS2 osteosarcoma, the MDA-MB-435 breast cancer line, and LN-428 glioblastoma cells.

As used herein, the term "treat", "treated" or "treating," when used with respect to a cancer refers to a therapeutic measures taken to reduce or eliminate the cancerous cells in the subject or prevent it from becoming worse. Thus, the phrase "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

As used herein, "monitoring effectiveness" refers to determination of biological response of a subject to a treatment. Typically, the monitoring involves assaying or measuring of one or more suitable physiological parameters (e.g., biomarkers) that indicate that the subject has responded to the particular treatment. Preferably, monitoring involves assaying or measuring of one or more suitable physiological parameters before and after such a treatment wherein relative changes in the physiological parameters being assayed or measured indicate whether the treatment is effective to the subject. In some cases, subject may be monitored over a period of time, during the duration of the particular treatment and/or after the completion of the treatment, to determine the effectiveness of the treatment over time. Relative changes in physiological parameters being measured that are indicative of an effective treatment depend on the nature of the parameter being considered. In some cases, a practitioner may also take into account the general sense of wellbeing that is reported by a patient.

Where cells (e.g., cancer cells) are to be contacted with a compound in vivo, it can be achieved by administration of the compound to a subject. The term "administration" and variants thereof (e.g., "administering" a compound) in reference to compounds mentioned herein means introducing the compound into the system of the animal in need of treatment. When a compound is provided in combination with one or more other active agents, "administration" and its variants are each understood to include concurrent and sequential introduction of the compound and other agents.

When administered, the therapeutic compositions described in the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines, and optionally other therapeutic agents.

As used herein, the term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The therapeutics of the invention can be administered by any conventional route, including injection or by gradual infusion over time. The administration may, for example, be oral, intravenous, intratumoral, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in Remington's Pharmaceutical Sciences, 18th edition, 1990, pp 1694-1712). Those of skill in the art can readily determine the various parameters and conditions for producing antibody aerosols without undue experimentation. When using antisense preparations, slow intravenous administration is preferred.

The compositions described in the present invention are administered in effective amounts. An "effective amount" is the amount of a Chk1 inhibitor to be administered in conjunction with a genotoxic therapy, such as a chemotherapy and/or a radiation therapy, that together with further doses, produces the desired response, e.g., an inhibition of tumor growth, metastasis, or killing of cancerous cells. For treating cancer, a desired response can be inhibiting the progression of the disease. This may involve only slowing the progression of the disease temporarily, although more preferably, it involves halting the progression of the disease permanently. This can be monitored by routine methods or can be monitored according to known methods.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

As demonstrated in Examples, a Chk1 inhibitor sensitizes certain cancer cells to genotoxic stress, such as a chemotherapy and/or a radiotherapy. Accordingly, it may be possible to reduce the effective amount or dosage of a conventional chemotherapeutic agent and/or radiation substantially and still achieve the same or even enhanced effectiveness of such treatments when a Chk1 inhibitor is administered in conjunction. Thus, the Chk1 inhibitor-based cancer therapy as described herein may provide a cancer regimen that can reduce side effects stemming from a chemotherapy or a radiotherapy. Such cancer regimen may be particularly beneficial to those with a compromised immune system, who are at heightened risk of infections, since the reduction in the dose or duration of a genotoxic therapy may have a protective effect on healthy immune cells.

The pharmaceutical compositions used in the foregoing methods preferably are sterile and contain an effective amount of one or more Chk1 inhibitors, formulated either alone or together with a chemotherapeutic agent for producing the desired response in a unit of weight or volume suitable for administration to a patient. The response can, for example, be measured by determining caspase-2 activation as described elsewhere herein.

As used herein, a tissue sample is tissue obtained from a tissue biopsy using methods well known to those of ordinary skill in the related medical arts. The phrase "suspected of being cancerous" as used herein means a cancer tissue sample believed by one of ordinary skill in the medical arts to contain cancerous cells. Methods for obtaining the sample from the biopsy include gross apportioning of a mass, microdissection, laser-based microdissection, or other art-known cell-separation methods.

Because of the variability of the cell types in diseased-tissue biopsy material, and the variability in sensitivity of the diagnostic methods used, the sample size required for analysis may range from relatively small numbers of cells to large numbers of cells, e.g., 10, 50, 100, 200, 300, 500, 1000, 5000, 10,000, to 50,000 or more cells. The appropriate sample size may be determined based on the cellular composition and condition of the biopsy and the standard preparative steps for this determination and subsequent isolation of the nucleic acid for use in the invention are well known to one of ordinary skill in the art.

EXAMPLES

Although defects in the p53 response to DNA damage promote malignant transformation and therapeutic resistance, little is known about p53-independent response pathways. We report that otherwise nontoxic levels of Chk1 inhibition, as obtained genetically or pharmacologically, are sufficient to restore γ-radiation-induced cell death in p53 mutant zebrafish embryos. Surprisingly, caspase-3 is not cleaved prior to DNA fragmentation, contrasting with classical intrinsic or extrinsic apoptosis. Rather, a novel apoptotic program is activated that cell-autonomously requires atm, atr and caspase-2, is insensitive to bcl-2/xl overexpression and operates throughout the cell cycle. This Chk1-suppressed pathway defined in zebrafish is conserved in p53-deficient and BCL2-overexpressing human tumor cells radiosensitized by the Chk1 inhibitor Gö6976; the cells hyperactivate ATM, ATR and caspase-2 and trigger an apoptotic program that selectively requires caspase-2, but not caspase-3. While defining a new apoptotic modality in vertebrates, the Chk1-suppressed pathway also provides a selective and readily assessable means to sensitize a wide spectrum of human tumors to genotoxic therapy.

A Morpholino Screen for Suppressors of $p53^{e7/e7}$ Radioresistance Identifies Chk1

Figure 9A:
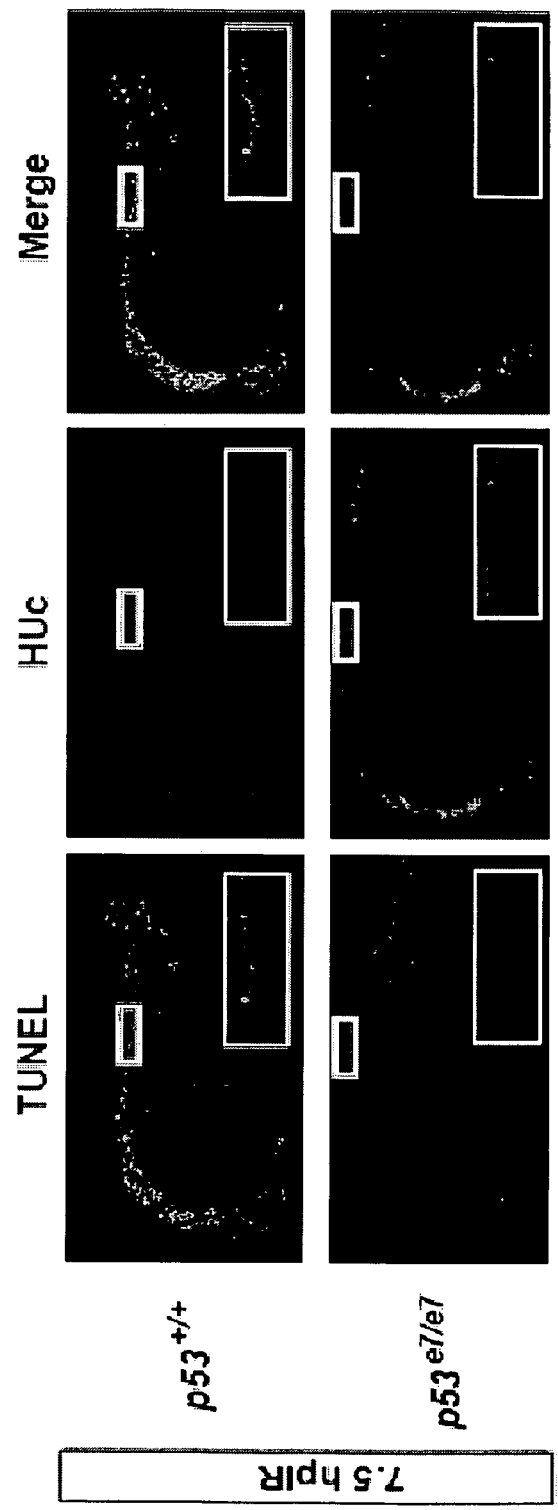
FIG. 9 provides six images of zebrafish embryos, showing that homozygosity for the $p53^{e7}$ mutation blocks IR-induced neuronal cell death in the embryos. Lateral views of whole-mount zebrafish embryos of indicated genotypes at 25.5 hpf, that were irradiated (12.5 Gy) at 18 hpf and processed for TUNEL and HUc immunohistochemistry. TUNEL labeling shown in left panels and pan-neural marker, HUc, shown in middle panels. Corresponding magnified views of spinal cord sections are boxed in white. Note high levels of TUNEL labeling and reduced HUc labeling in irradiated WT compared to mutant.

$p53^{e7/e7}$ mutant zebrafish embryos are refractory to DNA damage-induced apoptosis, as demonstrated by a nearly complete lack of TUNEL labeling in embryos examined 7.5 hours after whole-body IR delivered at 18 hours postfertilization (hpf) (FIG. 9; also Berghmans et al., 2005). In irradiated $p53^{+/+}$ embryos, by contrast, TUNEL labeling colocalizes with the pan-neural marker HUc throughout the developing nervous system (FIG. 9). Brain and spinal cord radiosensitivities can also be assessed in live $p53^{+/+}$ embryos treated with the vital dye acridine orange (AO) (FIG. 1A), which stains multiple forms of cell death. As with the TUNEL assay, irradiated $p53^{e7/e7}$ mutants are virtually devoid of AO-labeled cells (FIGS. 1A & 1B).

We used morpholino antisense oligonucleotides (MOs) to knock down the expression levels of 8 zebrafish S- and G2-checkpoint kinases in $p53^{e7/e7}$ mutant embryos and assessed the ability of each knockdown to restore cell death (AO reactivity) at 7.5 hours post-IR (hpIR). We also tested several double-knockdown combinations, as well as knockdowns of non-kinase checkpoint regulators ($p21^{waf1/cip1}$ and smc1). For each knockdown, we scored a minimum of 50 embryos and quantified AO staining in at least 5 embryos. To avoid the isolation of false-positives, we adjusted the concentrations of each MO to the maximal dose compatible with normal embryonic development in the $p53^{e7/e7}$ background.

Figure 1B:
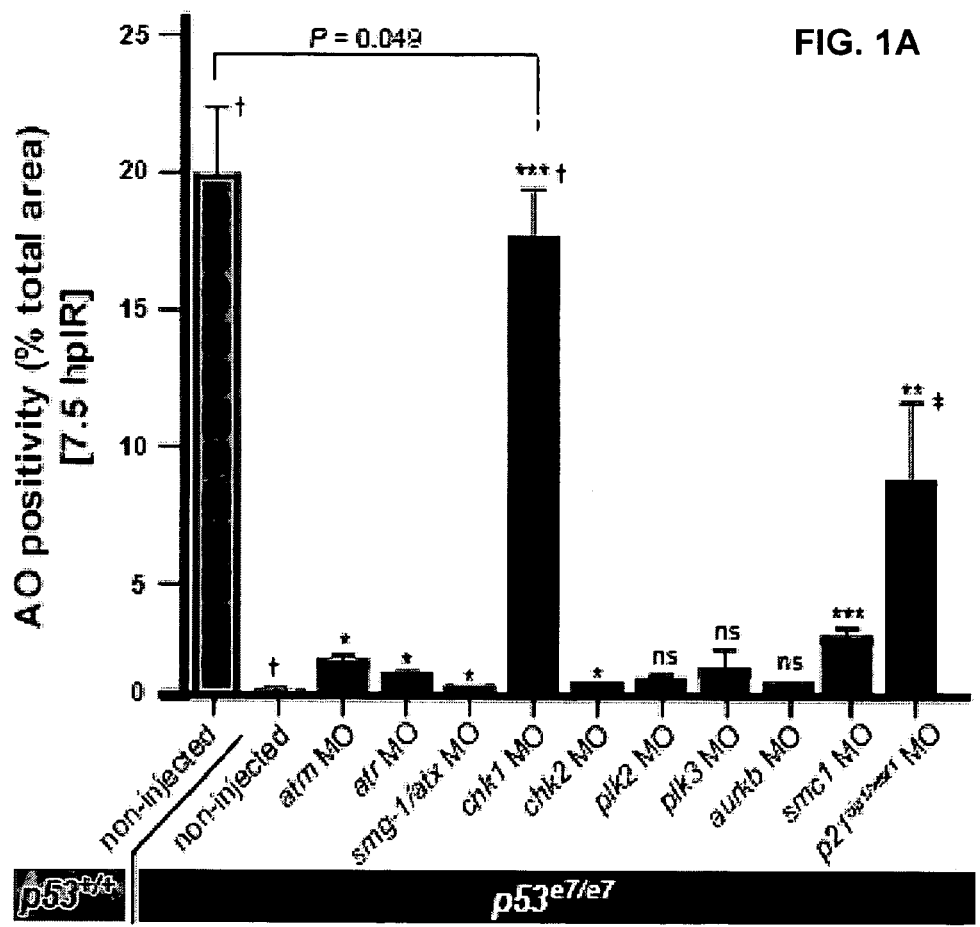
Figure 1C:
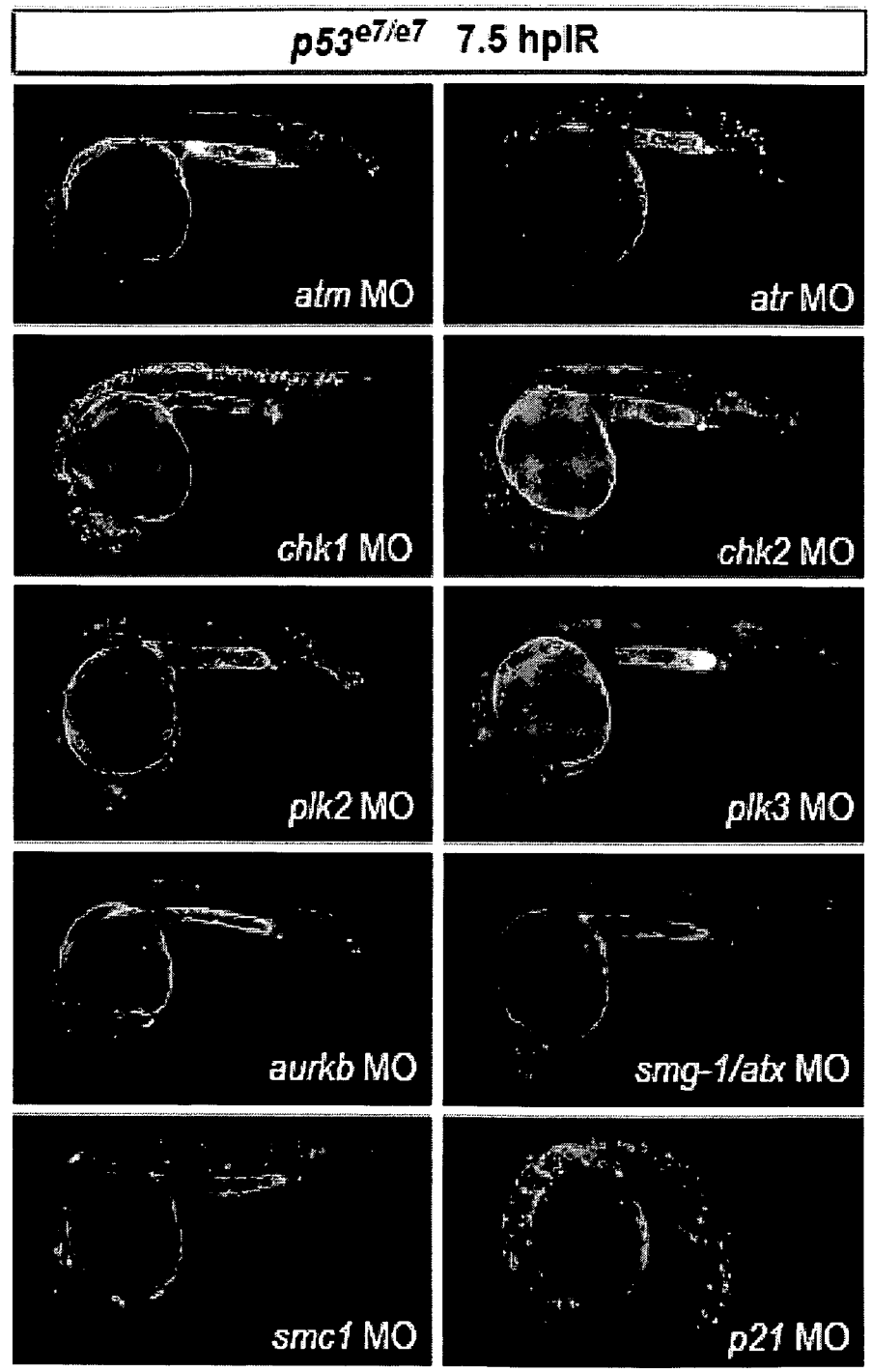
Figure 2A:
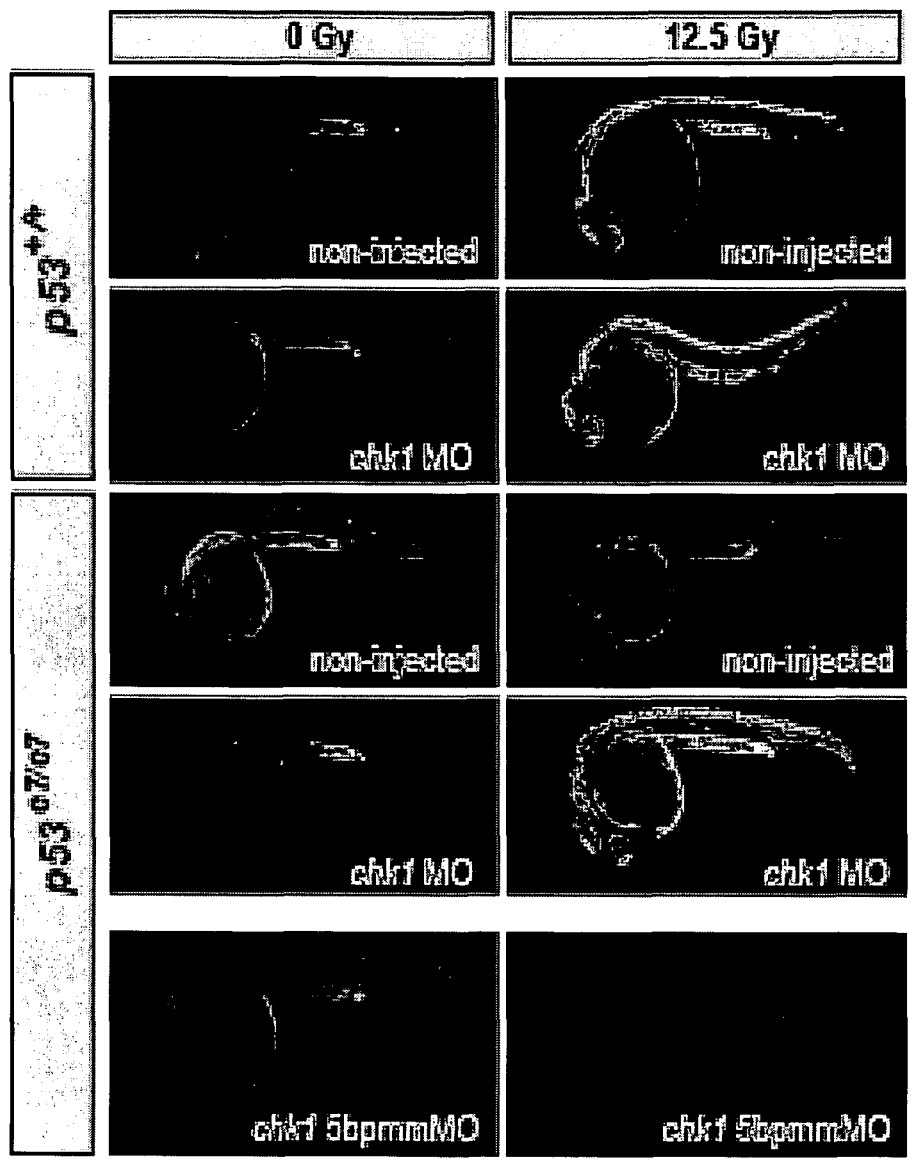
FIG. 2 provides a series of fluorescent images, western blot images, in situ hybridization images and two sets of graphs as outlined below. chk1 knockdown radiosensitizes p53 mutants but is otherwise compatible with normal zebrafish development. (A) Fluorescence images of representative embryos of indicated genotypes+/−chk1 MO after 0- or 12.5-Gy IR. 5 bpmmMO, 5-base-pair mismatch MO. (B) Quantified AO responses of indicated genotypes with or without IR (12.5 Gy) and chk1 MO. Gray bars, $p53^{+/+}$ background; black bars, $p53^{e7/e7}$ background. AO staining was quantified in ≥8 embryos per condition, with ≥1000 embryos scored. All data are reported as means+/−SEM. *P<0.0001 (two-tailed Student's t-test). (C) Western blots comparing the levels of Chk1, Chk2 and phosphorylated Cdc2 (Tyr15) in protein lysates from 25.5-hpf embryos injected with the indicated MOs. (D) Nonirradiated $p53^{+/+}$;chk1MO larva photographed live at 5 dpf shows no apparent developmental defects but are slightly delayed (smaller swim bladder). Such larvae survived to adulthood. (E) Fluorescence images of representative embryos of indicated genotypes. $p53^{e6}$ is the N168K mutation, corresponding to human residue 200. p53MO, MO against the p53 5'UTR. (F) Fluorescence images of live transgenic embryos injected with the indicated MOs at the 1-cell stage and expressing EGFP in the notochord (top, embryos photographed at 24 hpf) or in myeloid progenitors (bottom, embryos photographed at 16.5 hpf). Tg(myoD:EGFP) and Tg(pu.1:EGFP) embryos were treated with or without IR (12.5 Gy) at 18 hpf and 10 hpf, respectively. Insets: higher magnification views of GFP-expressing cells. Top row, lateral views, anterior to the left. Bottom row, dorsal views, anterior facing down. (G) Quantification of myeloid cells in 28 hpf embryos generated as indicated (x-axis) and processed as in panel H. Gray bars, $p53^{+/+}$ background; black bars, $p53^{e7/e7}$ background. mpo/lplastin staining was quantified in 15 embryos per condition. Data are reported as means+/−SD. P<0.001, ***P<0.0001 (two-tailed Student's t-test). Note that while the numbers of mpo/l-plastin-positive cells are reduced ~3-fold in IR-treated versus untreated $p53^{+/+}$ embryos, they are unchanged in treated versus untreated $p53^{e7/e7}$ embryos. Also note that chk1 knockdown induces an average 2-fold reduction in myeloid cell numbers in the $p53^{e7/e7}$ background. (H) Images of representative 28 hpf embryos of indicated genotypes processed for in situ hybridization of mpo and l-plastin riboprobes (differentiated granulocytes and monocytes; indicated with white arrows) and band3 (erythrocytes; indicated with gray arrowheads). Note the specific reduction in number of granulocytes/monocytes.
Figure 2B:
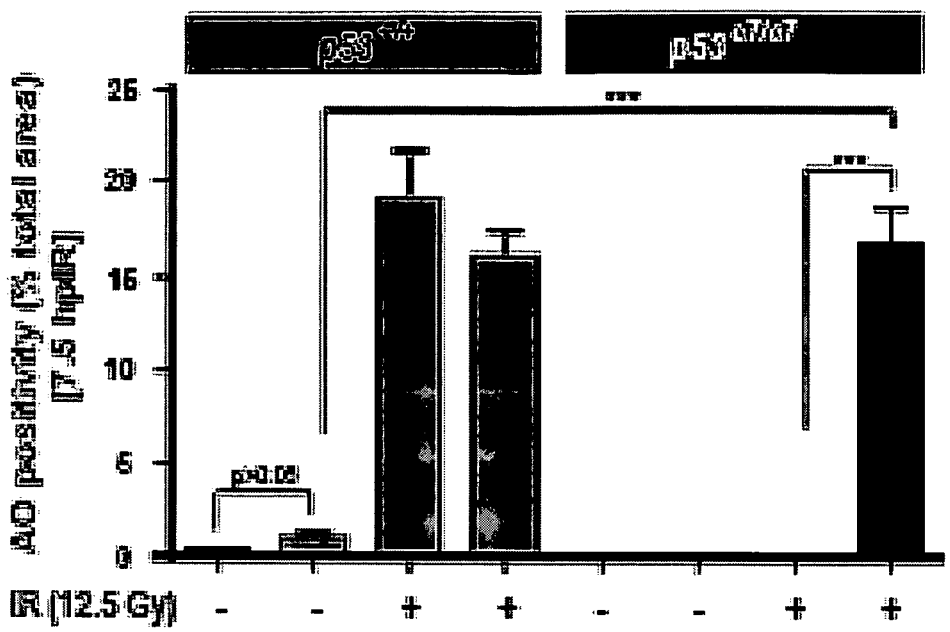
Figure 2C:
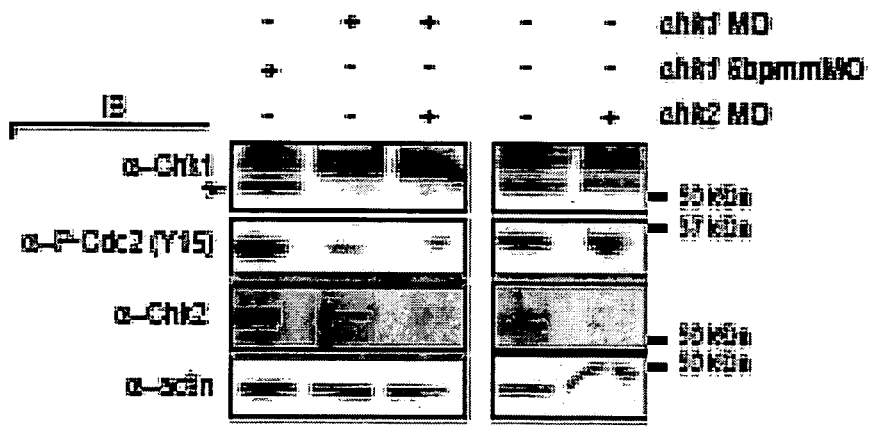
Figure 2D:
Figure 2E:
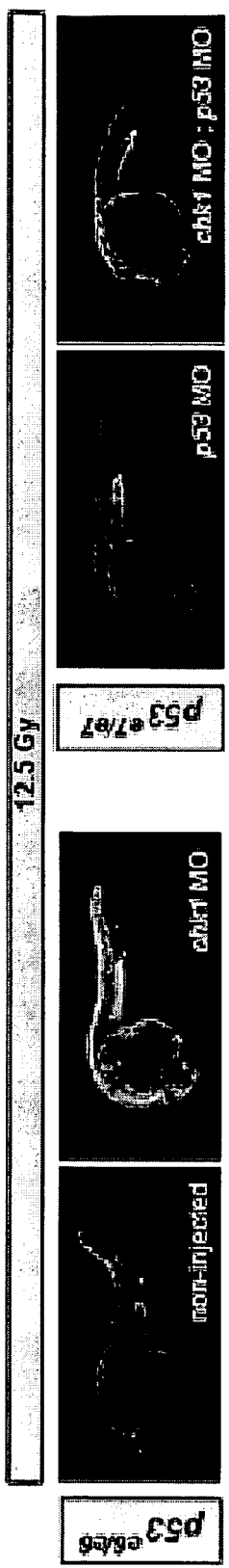
Figure 10A:
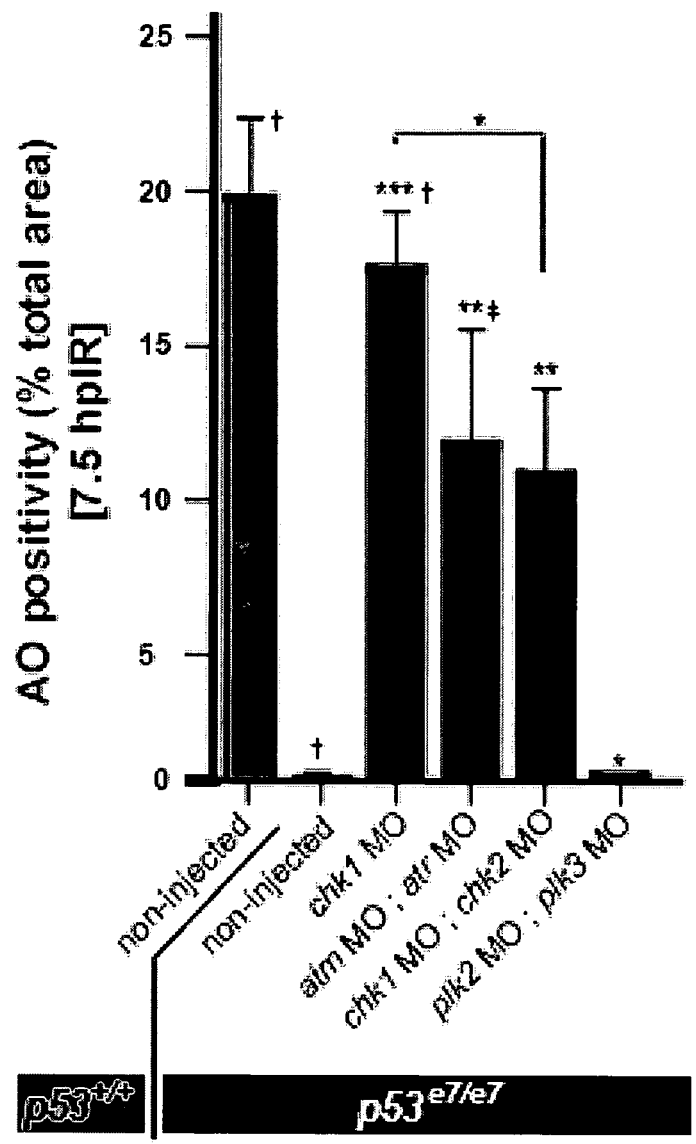
FIG. 10 provides a graph and a set of images of mutant embryos, demonstrating the radiosensitizing effects of selected kinase double-knockdowns in p53 mutants, as described below. (A) MO screen for loss-of-function suppressors of $p53^{e7/e7}$-associated radioresistance (continued from FIG. 1B). Noninjected and 1 cell-stage MO-injected embryos were irradiated at 18 hpf (12.5 Gy). AO uptake by cells was quantified by analyzing images of whole embryos photographed live at 7.5 hpIR (y-axis) (images as shown in FIG. 10B). Injected MOs are indicated along the x-axis. Bars also indicate the genetic background used for injections (light gray, $p53^{+/+}$; dark gray, $p53^{e7/e7}$). AO staining was quantified in ≥8 embryos per knockdown, with 50 or more embryos scored per knockdown (except †, ≥1000); ‡, embryos showed developmental defects. All data are reported as means+/−SEM. Statistical significance versus the noninjected $p53^{e7/e7}$ response: *P<0.05; P<0.005; *P<0.0005 (two-tailed Student's t-test). (B) Live p53 mutant embryos injected with the indicated MO combinations, stained with AO at 7.5 hpIR (12.5 Gy) and representative of the phenotypes quantified in FIG. 10A. Anterior, left.
Figure 10B:
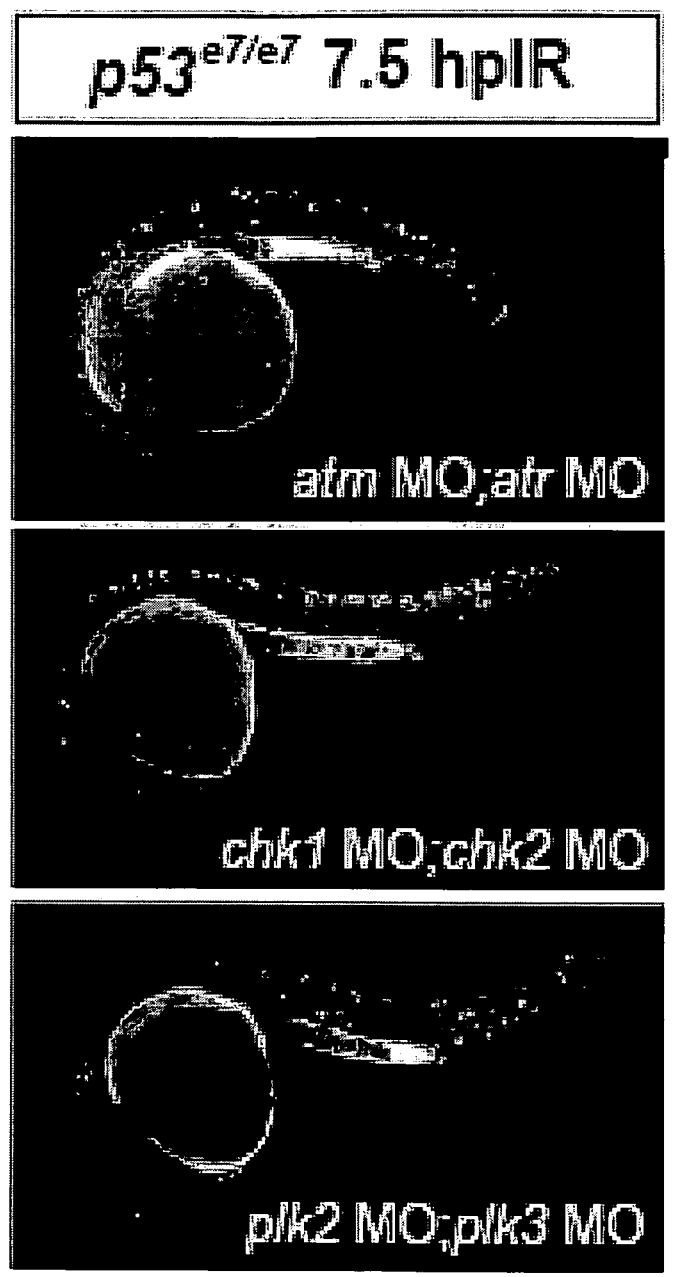

Single knockdowns of all genes tested, excluding plk2, plk3 and aurkb, radiosensitized p53 mutants with variable efficiency (FIGS. 1B & 1C). Whereas atm, atr, smg-1/atx, and chk2 deficiencies restored only minor AO reactivity averaging 1-5% of the $p53^{+/+}$ response, chk1 knockdown resulted in a staining pattern that closely resembled wild-type (87.7% of the $p53^{+/+}$ response, P<0.0001; see also FIGS. 2A & 2B). This suppressor effect resulted specifically from chk1 knockdown because (i) injections of a chk1 mismatch MO failed to radiosensitize p53 mutants (FIG. 2A, bottom panels), (ii) the chk1 MO resulted in a robust reduction of the endogenous Chk1 protein pool, correlating with impaired Chk1 activity (FIG. 2C) and (iii) a specific inhibitor of human Chk1, but not inhibitors of ATM or Chk2, phenocopied the effects of chk1 MO (see FIG. 8 below). chk1 MO also fully radiosensitized $p53^{e6}$ ($p53^{N168K}$) homozygotes (Berghmans et al., 2005) and p53 morphants (Langheinrich et al., 2002) lacking p53 protein (FIG. 2E). The radiosensitizing effect of chk1 knockdown was modestly attenuated by chk2 depletion (FIG. 10; compare bars 3 and 5 in 10A). This observation may reflect a weak contribution of Chk2-mediated p53-independent apoptosis (e.g., Urist et al., 2004) to chk1MO-induced radiosensitization of p53 mutants (but see FIGS. 5, 18 and Discussion). Irradiated $p53^{e7/e7}$;atmMO;atrMO embryos showed AO labeling similar to that of $p53^{e7/e7}$;chk1MO embryos (FIG. 2A). While consistent with the notion that ATM and ATR redundantly activate Chk1 following IR (Kastan and Bartek, 2004), the net AO response of $p53^{e7/e7}$;atmMO; atrMO is likely overestimated due to severe developmental defects (FIG. 10B). Together, results of this MO screen provide first in vivo evidence that disruption of a subset of S- or G₂/M-checkpoint regulators is sufficient to restore IR sensitivity to p53 mutant cells. Below we focus our analysis on chk1. For simplicity, we refer to $chk1^{+/+}$ embryos that were injected with the chk1 MO as $chk1^{MO}$ embryos and non-injected control embryos as $chk1^{WT}$ embryos.

Transient Chk1 Depletion is Viable in the Absence of IR chk1 is indispensable during fly and mouse early embryogenesis, with homozygous null mutants succumbing to major cell cycle defects (Fogarty et al., 1997; Liu et al., 2000). This essential function argues that radiosensitization of $p53^{e7/e7}$ zebrafish embryos upon chk1 knockdown might reflect a lethal phenotype rather than a DNA damage-dependent event per se. Unexpectedly, however, knockdown of zebrafish chk1 had no apparent effect on unirradiated zebrafish development and viability, in either the $p53^{+/+}$ or $p53^{e7/e7}$ background (FIGS. 2A & 2D; compare bars 1 and 2 in FIG. 2B). Western blots performed with an anti-zebrafish Chk1 antibody revealed a marked knockdown of the protein in chk1 morphants (FIG. 2C). Thus, as expected from a MO knockdown experiment, chk1 morphants harbor residual levels of Chk1 activity, a notion supported by the weak but persistent levels of phosphorylated Cdc2 in morphant protein extracts (FIG. 2C). These results demonstrate that transient depletion, as opposed to persistent total loss (Liu et al., 2000), of Chk1 function is tolerable by vertebrate cells in vivo and compatible with long-term organismal viability. Crucially, however, as already shown above, such transient depletion is sufficient to radiosensitize p53 mutants (FIGS. 1B & 1C; also FIGS. 2A & 2B). Further analyses using a specific small-molecule inhibitor of Chk1 validated both of these notions (see FIG. 8).

Chk1 Depletion Radiosensitizes p53 Mutant Mesodermal Derivatives In Vivo

The AO assay established chk1 as a loss-of-function radiosensitizer of developing neurons in p53 mutant zebrafish embryos. To test whether this effect applies to embryonic tissues of non-neurectodermal origin, we analyzed mesodermal cell numbers in embryos from transgenic lines expressing GFP under control of various tissue-specific promoters.

Figure 2F:
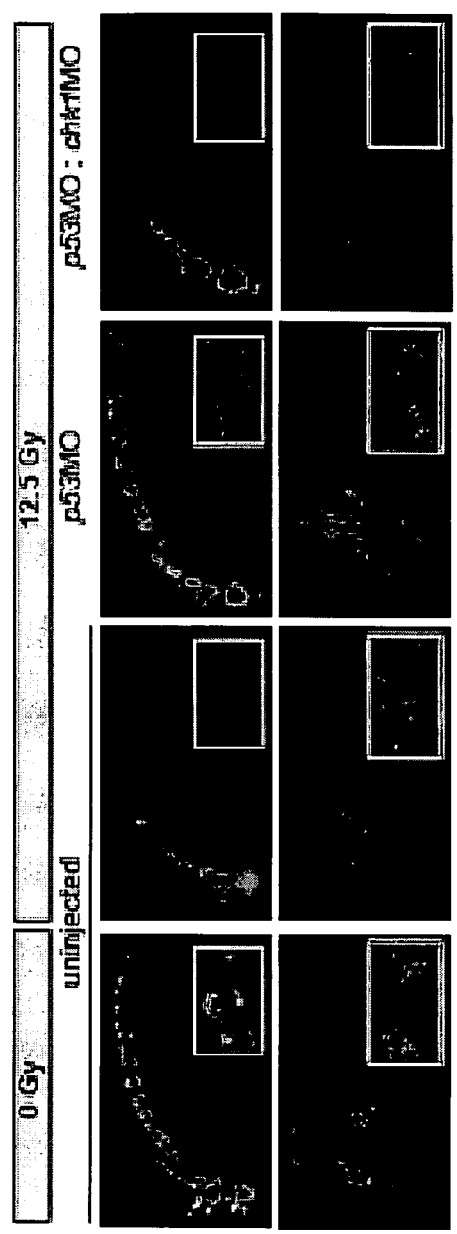
Figure 2G:
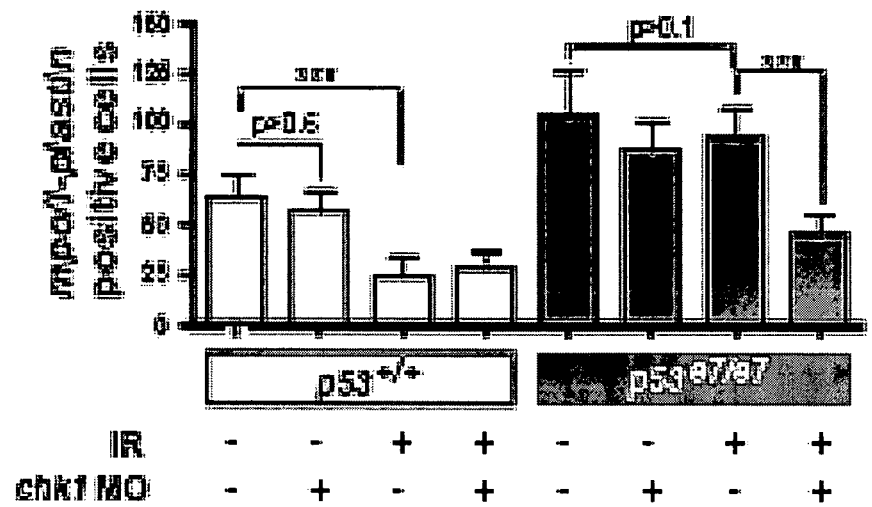
Figure 2H:
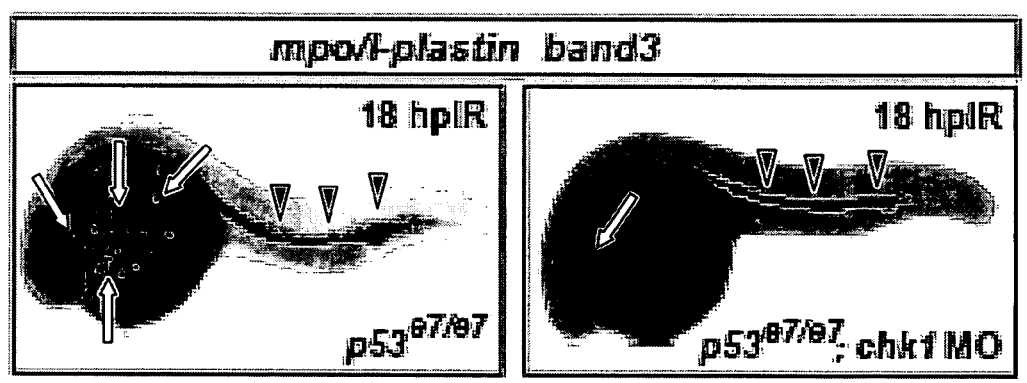

Notochord cells visualized in living Tg(myoD:EGFP) zebrafish (Yang et al., 2004) at 25 hpf were highly radiosensitive, as evidenced by the loss of EGFP-labeled cells in irradiated transgenic embryos (FIG. 2F). This cell death response was abolished through p53 knockdown. Similarly strong p53-dependent radiosensitivity was observed in myeloid progenitor cells visualized in living Tg(pu.1:EGFP) embryos (Hsu et al., 2004) (FIG. 2F), and was quantified in fixed embryos stained with myeloperoxidase (mpo, granulocytic marker) and l-plastin (monocytic marker) (Berman et al., 2005) riboprobes (FIGS. 2G & 2H). p53 knockdown-mediated radioresistance in both notochord and myeloid cells was overcome by chk1 knockdown (FIGS. 2F-2H). Similar to its effects in developing neurons, chk1 knockdown had no effect in the absence of IR (FIG. 2H and data not shown). These results indicate that chk1MO-mediated radiosensitization of p53 mutants is not confined to neuronal cell types, and confirm that cell death induced by Chk1 depletion is strictly IR-dependent.

Figure 3A:
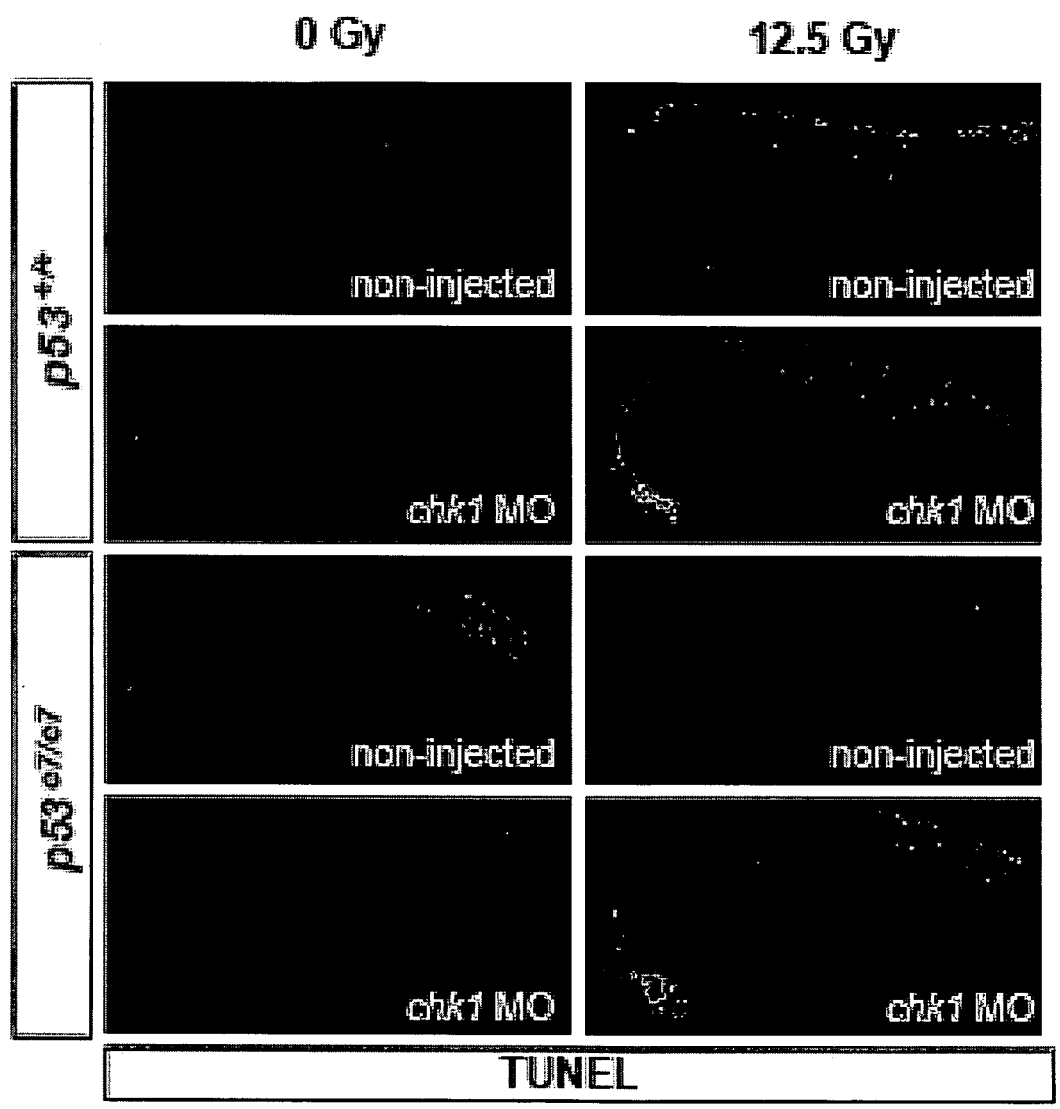
FIG. 3 provides a series of fluorescence images, electron micrographs and a schematic illustration of experimental procedure as outlined below. IR-induced p53-independent apoptosis after Chk1 loss occurs cell-autonomously and independently of caspase-3. (A) Fluorescence images of 25-hpf embryos (anterior, left). TUNEL reactivity after IR (0 or 12.5 Gy) recapitulates live AO labeling (see FIG. 2A). (B) Embryos from the same experiment immunostained with an anti-activated-Casp-3 antibody. Note the absence of immunoreactivity in the $p53^{e7/e7}$;chk1$^{MO}$ embryo. (C) Electron micrographs (sagital sections) of the CNS in embryos of indicated genotypes after 0 or 12.5 Gy IR. Gö6976 is a specific Chk1 inhibitor (see FIGS. 6-8). Upper row, 1900× views. Lower row, 4800× views of the areas boxed in corresponding upper panels. Note the multiple cells with stereotypical chromatin compaction and/or segregation in columns 2 and 4, hallmarks of apoptosis, as opposed to healthy nuclei in columns 1 and 3. Also note that organelles and plasma membrane are intact in the shown Chk1-inhibited irradiated p53 mutant cell, as expected from an apoptotic (as opposed to necrotic) event. See FIG. 13 for more details. Scale bar, 2 µM. (D) Experimental procedure for the generation of the genetic mosaics shown in FIG. 3E. (E) 5-µm thick confocal sections of spinal cords in irradiated mosaics. TMR Dextran (shown in left panels) marks the donor cells. TUNEL shown in middle panels. First row, cells from a $p53^{e7/e7}$ embryo that was injected with the chk1 MO at the 1-cell stage ($p53^{e7/e7}$; chk1$^{MO}$ embryo) transplanted into a $p53^{e7/e7}$ host. Second row, $p53^{e7/e7}$ cells transplanted into a $p53^{+/+}$;chk1$^{MO}$ host.
Figure 13:
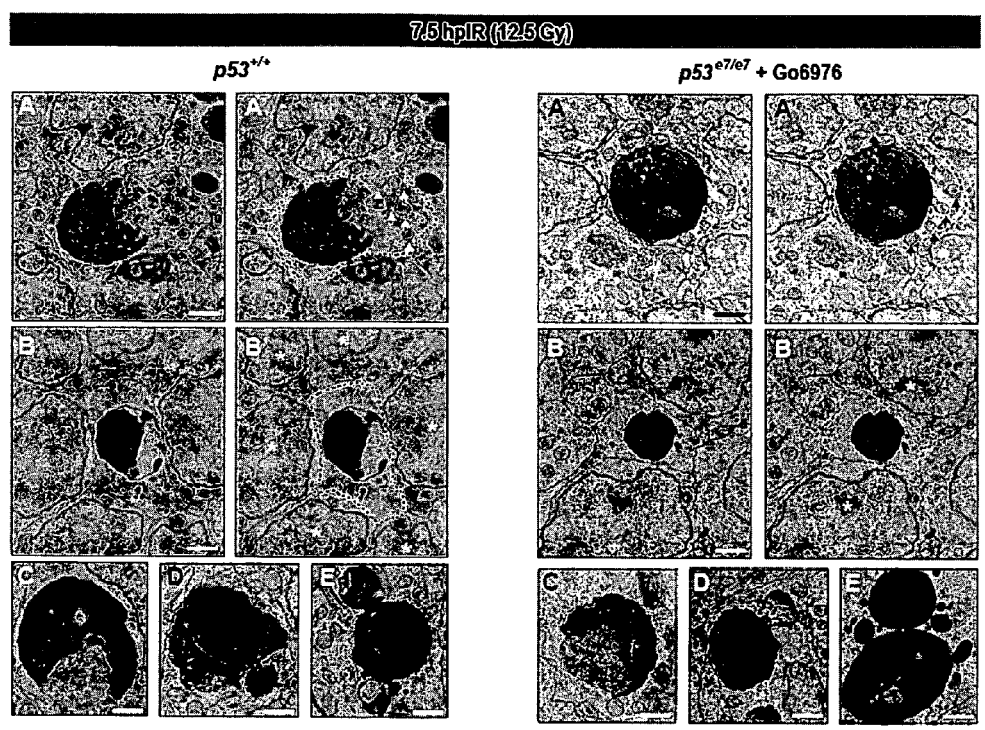
FIG. 13 provides a set of electron micrographs for comparative ultrastructural analysis of the mitochondrial and Chk1-suppressed apoptotic pathways. Electron micrographs (sagital sections, 4800× views) of wild-type versus Chk1-inhibited p53 mutant CNS after 12.5 Gy IR. Gö6976 is a specific Chk1 inhibitor (see FIGS. 6-8). Cytologic hallmarks of apoptosis (as defined in Wyllie et al., 1980) are shown as follows. (A) Nuclear chromatin compaction and segregation alongside retention of intact cytoplasmic organelles and plasma membrane (white arrowheads and dashed outline, respectively, in panel A'). (B) Nuclear chromatin compaction and segregation alongside cytoplasmic condensation. In B', the plasma membrane is outlined and the nuclei of surrounding healthy cells are indicated by white asterisks. Compare the size of the apoptotic cell to the size of healthy nuclei. (C-E) Nuclear morphology of early (shown in FIG. 13C), mid-stage (shown in FIG. 13D) and late stage (shown in FIG. 13E) apoptosis. (C) Nuclear chromatin compaction and segregation. (D) Nuclear budding. (E) Nuclear fragmentation. Scale bar, 1 µm.

Irradiated p53$^{e7/e7}$;chk1$^{MO}$ Embryos Undergo Caspase-3-Independent Cell-Autonomous Apoptosis chk1 knockdown might restore a wild-type response to IR (that is, classical intrinsic apoptosis; (Kratz et al., 2006)) or trigger a different cell death program in p53 mutants. To decide between these possibilities, we first analyzed two hallmark markers of apoptosis, TUNEL-positive DNA fragmentation and cleaved caspase-3, as well as electron micrographs, in embryos fixed at 7.5 hpIR. AO labeling of irradiated p53$^{e7/e7}$;chk1$^{MO}$ embryos (FIGS. 1C & 2A) correlated with high levels of TUNEL labeling throughout the CNS, similar to findings in irradiated p53$^{+/+}$ embryos (FIG. 3A). Consistently, multiple cells showing similar ultrastructural hallmarks of apoptosis were found in the irradiated CNS of p53$^{+/+}$ and Chk1-depleted p53$^{e7/e7}$ embryos (see FIGS. 3C & 13 for details).

Figure 3B:
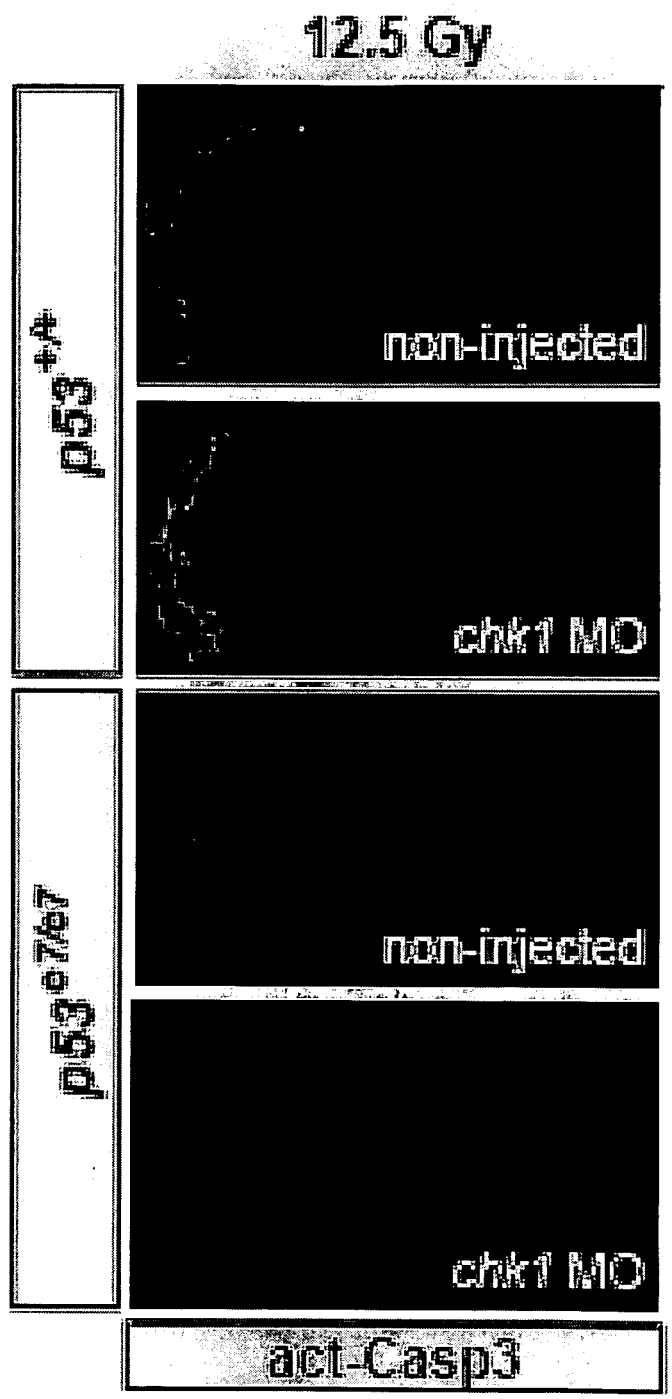
Figure 3C:
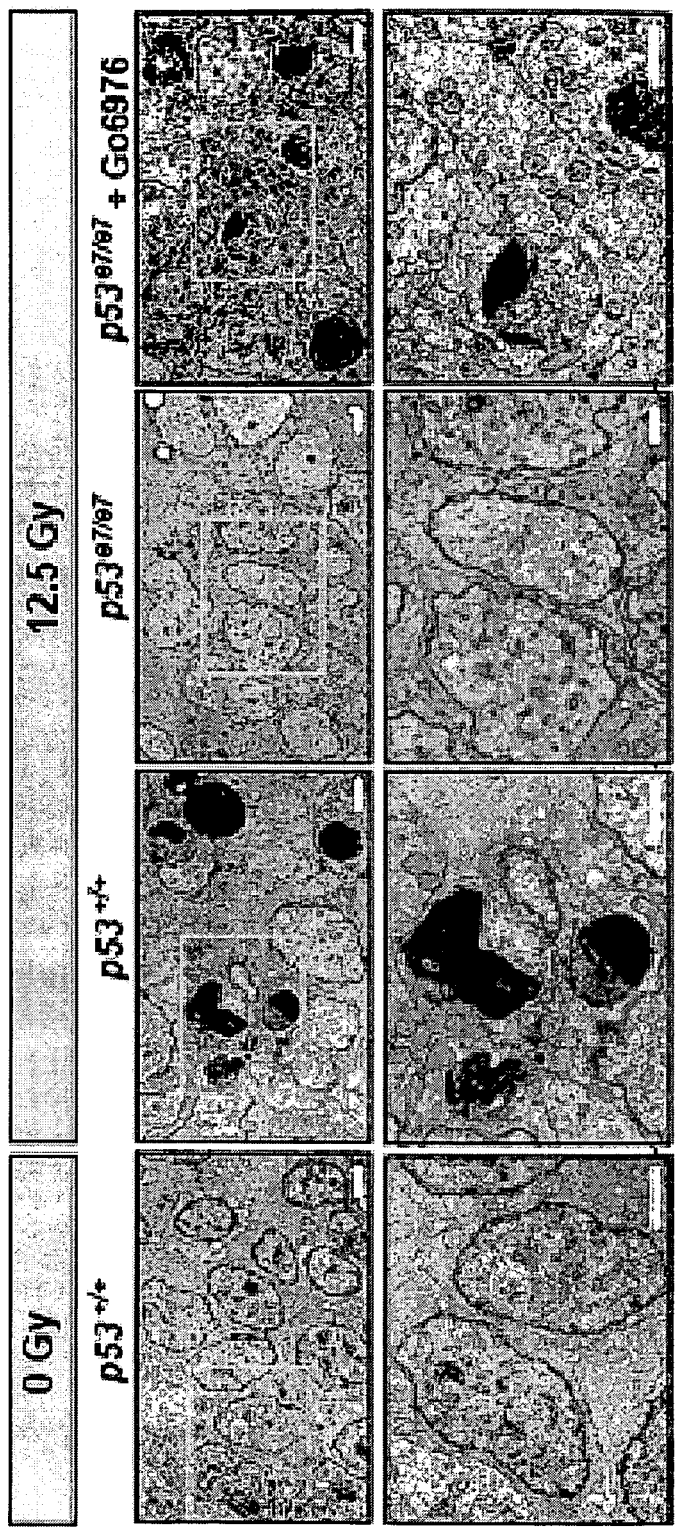
Figure 12:
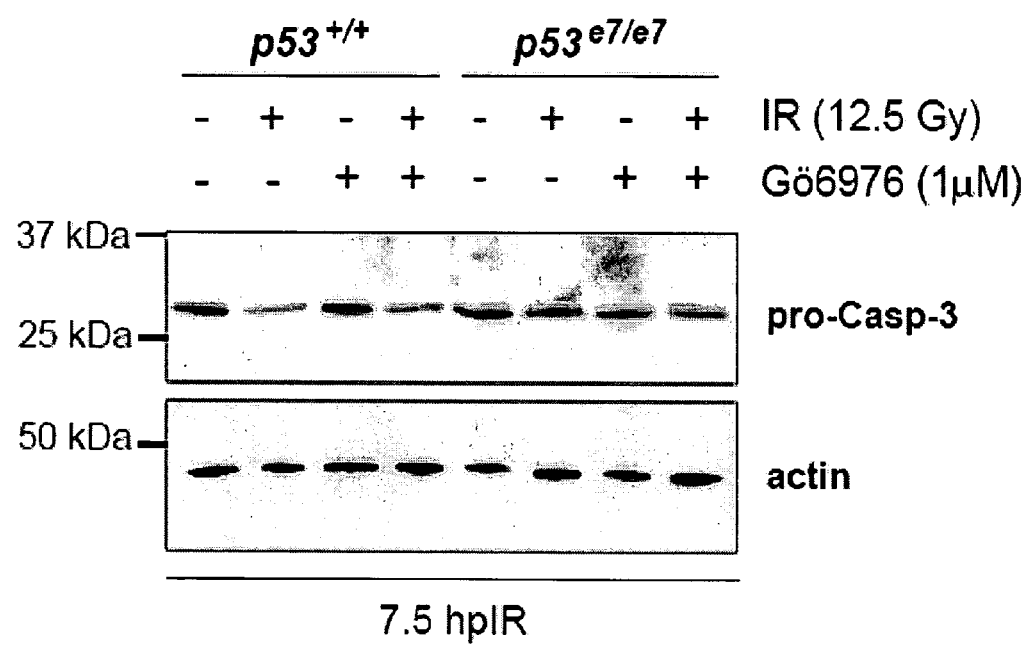
FIG. 12 provides a set of western blot images, showing that IR leads to a decrease in procaspase-3 levels in wild-type embryos but not in $p53^{e7/e7}$ or Chk1-inhibited $p53^{e7/e7}$ embryos. Western blot comparing the levels of procaspase-3 in wild-type versus p53 mutant embryos 7.5 hr after 0 or 12.5 Gy IR in the presence or absence of the specific Chk1 inhibitor Gö6976 at 1 μM (see FIGS. 6-8). Note that IR leads to a significant reduction in procaspase-3 levels in wild-type embryos exposed or not the inhibitor, as expected from cleavage of the pro-form. In contrast, no such decrease in procaspase-3 levels is observed in isogenic irradiated p. 53 mutants even after exposure to the inhibitor (lane 8), even though 1 µM of Gö6976 restored IR-induced cell death with complete penetrance in these mutants (FIG. 8A). The anti-caspase-3 antibody used in this experiment is the rabbit anti-human caspase-3 pAb from Stressgen (AAS-103) that recognizes procaspase-3 in all species thus far tested, including Xenopus. The band showing reduction in irradiated wild-type embryos migrates between the 25 and 37 kDa markers, consistent with the predicted sizes of zebrafish procaspase-3a and procaspase-3b (31 kDa), strongly supporting cross-reactivity.

Surprisingly, however, while irradiated p53$^{+/+}$ embryos stained strongly for activated caspase-3 (act-Casp-3), irradiated p53$^{e7/e7}$;chk1$^{MO}$ embryos did not (FIG. 3B). In fact, despite their strong TUNEL labeling, irradiated p53$^{e7/e7}$; chk1$^{MO}$ embryos showed no increased act-Casp-3 levels compared to p53 single mutants, which were devoid of both TUNEL and act-Casp-3 staining (FIGS. 3A & 3B). Consistent with these findings, immunoblotting for procaspase-3 showed that while wild-type embryos had reduced pro-caspase-3 levels after IR, indicating cleavage, Chk1-depleted p53$^{e7/e7}$ embryos did not, similar to p53$^{e7/e7}$ single mutants (FIG. 12). TUNEL labeling in irradiated p53$^{e7/e7}$;chk1$^{MO}$ embryos did not result from an earlier wave of caspase-3 activation, because such specimens analyzed at 1.5-, 3-, 4.5- and 6-hpIR lacked act-Casp-3 immunoreactivity. Hence, p53-independent cell death at 7.5 hpIR due to Chk1 depletion is caspase-3-independent. Yet, by ultrastructural criteria, reactivity to AO and TUNEL (as well as annexin V; see FIGS. 6 & 7), and reliance on at least one caspase (see FIGS. 5-7), this type of death is clearly apoptotic. Thus, the p53-independent cell death-inducing DDR triggered by Chk1 depletion is a caspase-3-independent apoptotic pathway.

Figure 3D:
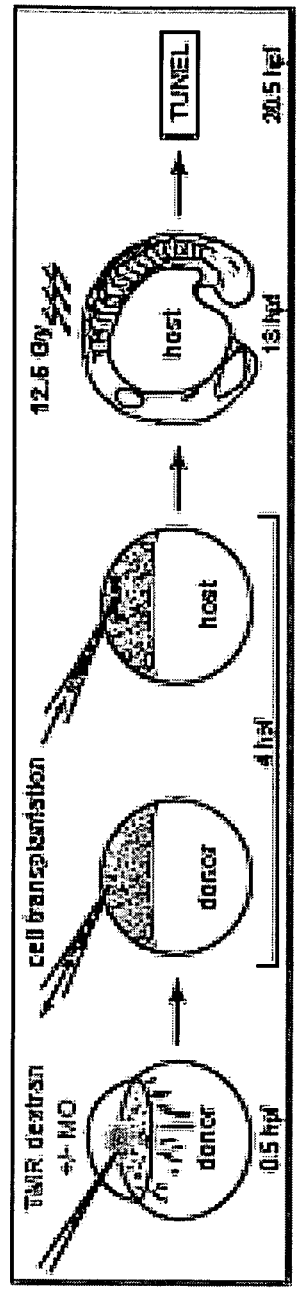
Figure 3E:
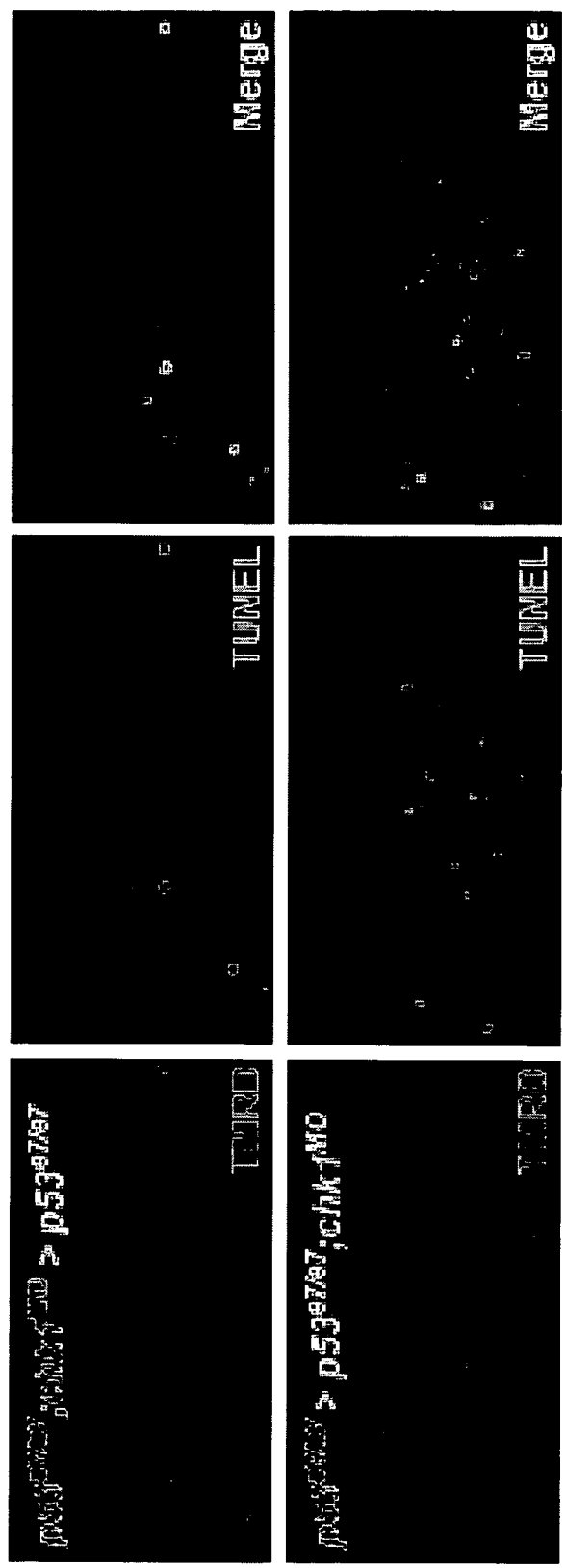
Figure 14:
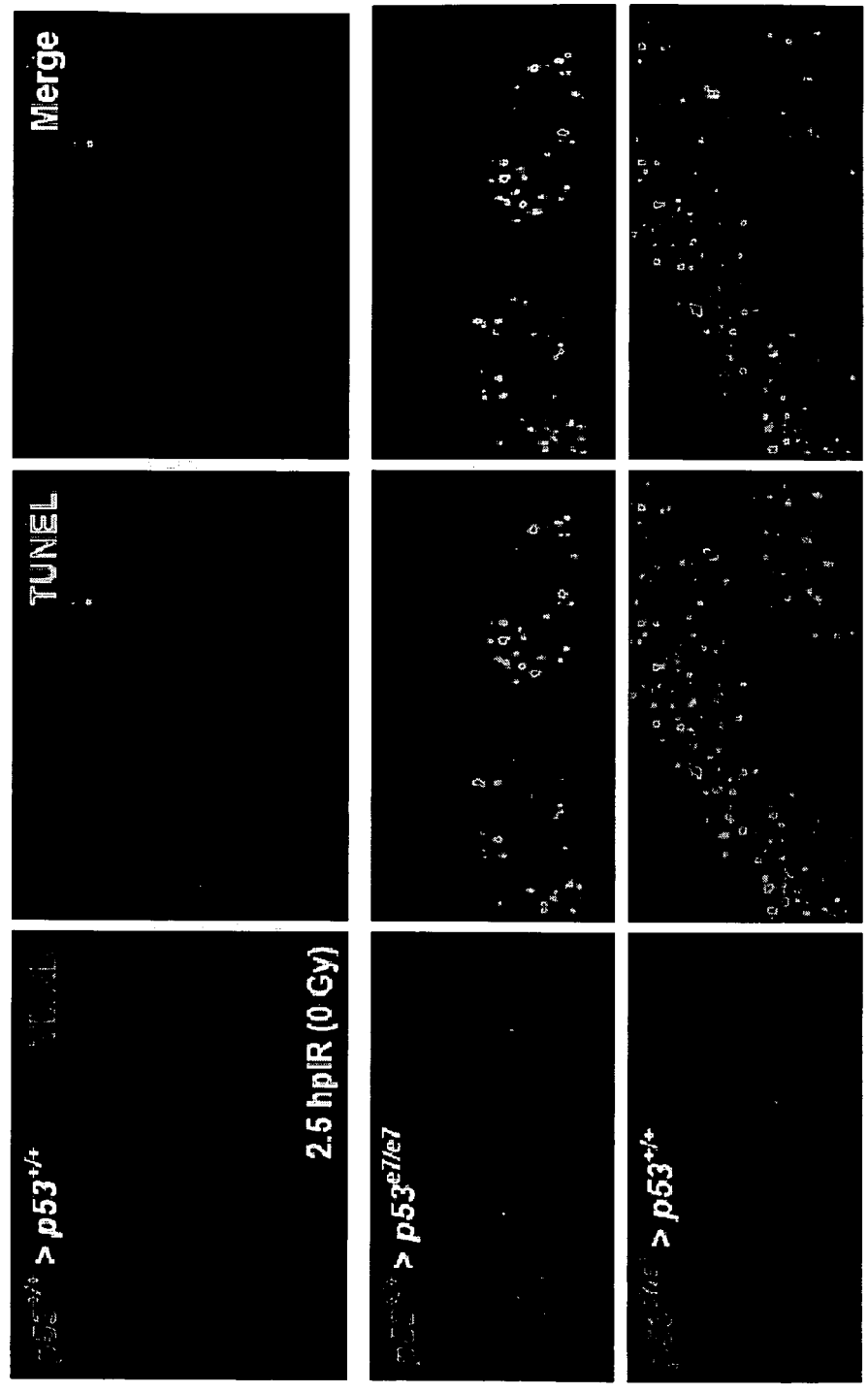
FIG. 14 provides a set of confocal images for validating the cell transplantation assay. (A) Dorsal view of a 5 µm thick confocal section of a $p53^{+/+}$ spinal cord. TMR Dextran (left) marks cells from a $p53^{+/+}$ donor embryo, which were transplanted at the blastula stage. TUNEL shown in middle panels. The genetic chimera was not irradiated. Note that the transplanted $p53^{+/+}$ cells do not stain TUNEL positive, showing that the transplantation technique does not induce apoptosis. (B, C) 5 µm thick confocal sections of spinal cords in irradiated mosaics. TMR Dextran (left) marks the donor cells. TUNEL shown in middle panels. (B) $p53^{+/+}$ cells transplanted into a $p53^{e7/e7}$ host. (C) $p53^{e7/e7}$ cells transplanted into a $p53^{+/+}$ host. Consistent with the fact that wild-type zebrafish embryos respond to IR through the cell autonomously-acting, mitochondrial apoptotic pathway (Berghmans et al., 2005; Kratz et al., 2006), $p53^{+/+}$ cells transplanted into $p53^{e7/e7}$ hosts stained TUNEL-positive after IR (86%, n=108) while neighboring $p53^{e7/e7}$ cells remained largely TUNEL-negative (shown in FIG. 14B). Furthermore, 86% (n=73) of $p53^{e7/e7}$ cells transplanted into $p53^{+/+}$ hosts remained refractory to IR-induced death, as indicated by their TUNEL negativity within an otherwise TUNEL-positive environment (see FIG. 14C). Hence, TUNEL reactivity of transplanted cells after IR strictly depends on the p53 genotype of a cell, occurs irrespective of the cellular environment, and has very little, if any, influence on neighboring cells.

To determine whether the Chk1-antagonized pathway functions cell autonomously or non-cell autonomously, we generated genetic chimeras (see cell transplantation procedure in FIG. 3D and assay validation in FIG. 14). While p53$^{e7/e7}$;chk1$^{MO}$ cells grafted into p53$^{e7/e7}$ hosts often stained TUNEL-positive after IR (39%, n=102), neighboring host cells were virtually never seen that stained TUNEL-positive (FIG. 3E, upper panels). In the reciprocal experiment, p53$^{e7/e7}$ cells transplanted into p53$^{e7/e7}$;chk1$^{MO}$ hosts remained TUNEL-negative within an otherwise TUNEL-positive environment (FIG. 3E, lower panels). Therefore, IR-induced TUNEL reactivity of transplanted cells strictly depends on Chk1 dosage, occurs irrespective of the cellular environment, and has very little, if any, influence on neighboring cells. The Chk1-suppressed apoptotic pathway thus functions in a cell-autonomous manner.

Irradiated p53$^{e7/e7}$;Chk1$^{MO}$ Cells Lack G$_2$/M Checkpoint Function but do not Preferentially Die During Mitosis Loss of Chk1 function in most eukaryotes results in a defective DNA damage-induced G$_2$/M checkpoint, which can lead to mitotic catastrophe (Chen and Sanchez, 2004; Fogarty et al., 1997; Zhou and Bartek, 2004). Because this type of death can be p53-independent and stain TUNEL positive (Castedo et al., 2004a; Okada and Mak, 2004), we examined G$_2$/M checkpoint function and mitotic death levels in irradiated p53$^{e7/e7}$;chk1$^{MO}$ embryos.

Figure 4A:
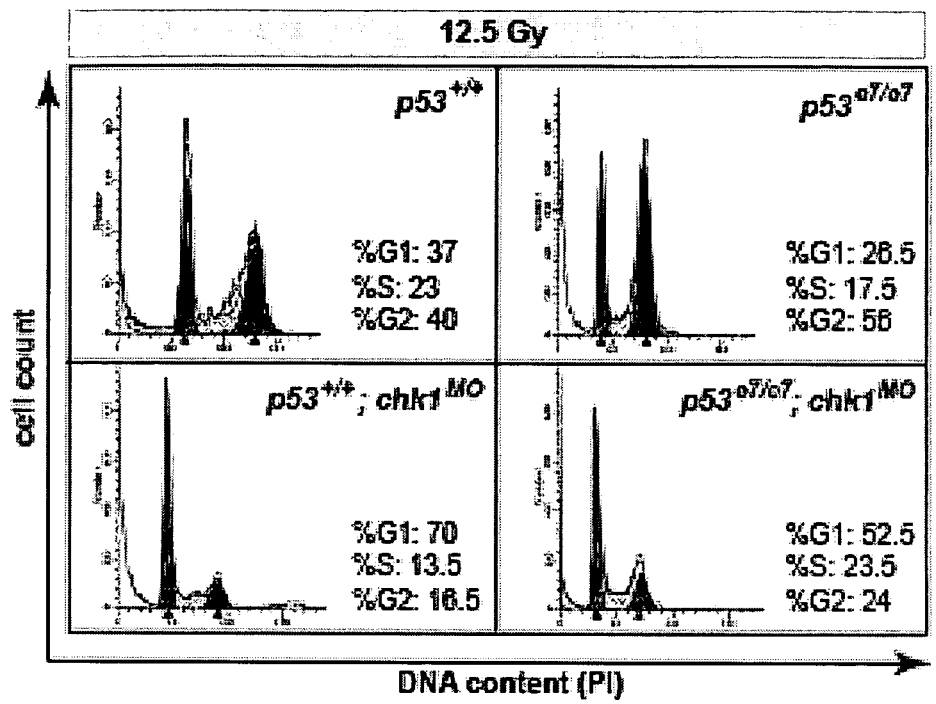
FIG. 4 provides a set of flow cytometry data, two sets of fluorescence images and three graphs as outlined below, showing p53-independent $G_2$/M checkpoint defects and catastrophic mitoses in irradiated chk1 morphants. (A) Cell-cycle profiles of zebrafish embryos of the indicated genotypes (6 hpIR) as determined by flow cytometry. DNA content analyzed by PI staining. (B) 4N DNA ratios (6 hpIR/0 hpIR) as determined by flow cytometry of PI-stained whole embryo homogenates. Embryos were irradiated (12.5 Gy) at 18 hpf. Data collected from 3 independent experiments are reported as means+/−SD. (C) Fluorescence images of representative embryos of indicated genotypes immunostained with an anti-phospho histone H3 antibody. (D) Quantification of the pH3 immunostainings shown in panel C. Data are means+/−SEM. **P<0.01 (two-tailed Student's t-test). (E) Confocal images of the caudal spinal cord in representative embryos of each indicated genotype processed for TUNEL (left)/pH3 (middle) double-labeling. (F) Percentage of double-labeled cells among >200 pH3-positive cells visualized on images as in panel E. Data are means+/−SEM.
Figure 4B:
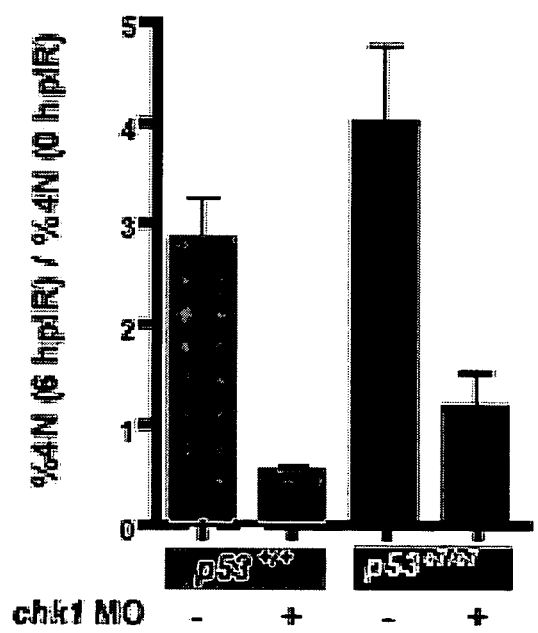
Figure 4C:
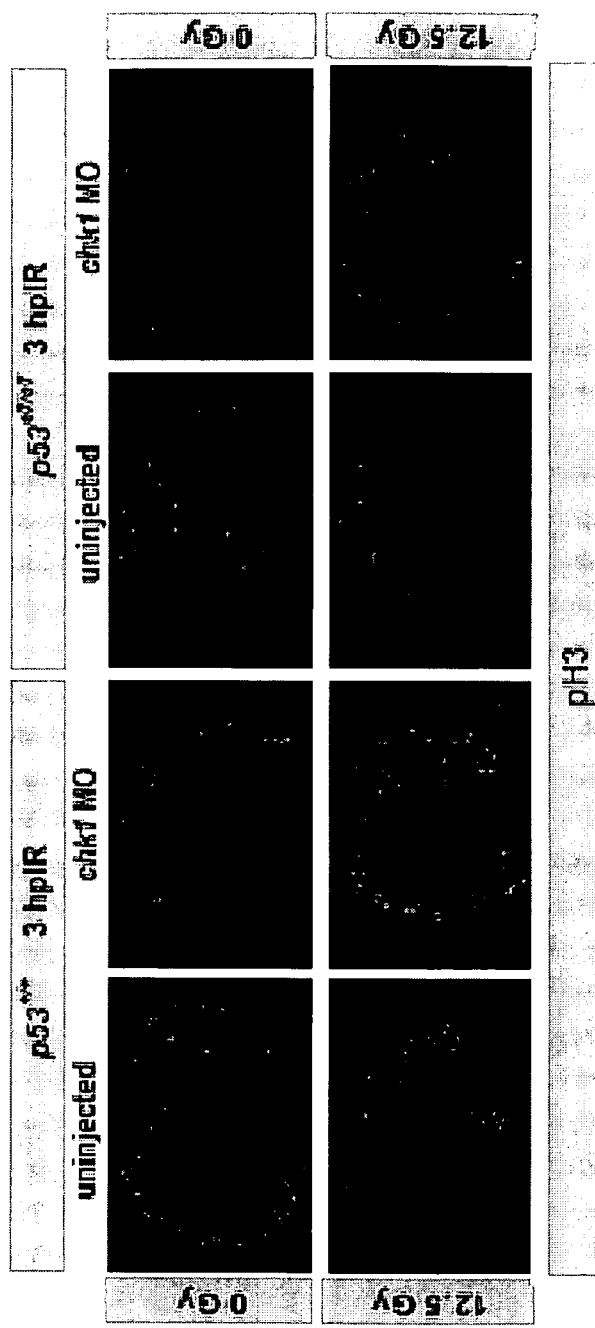
Figure 4D:
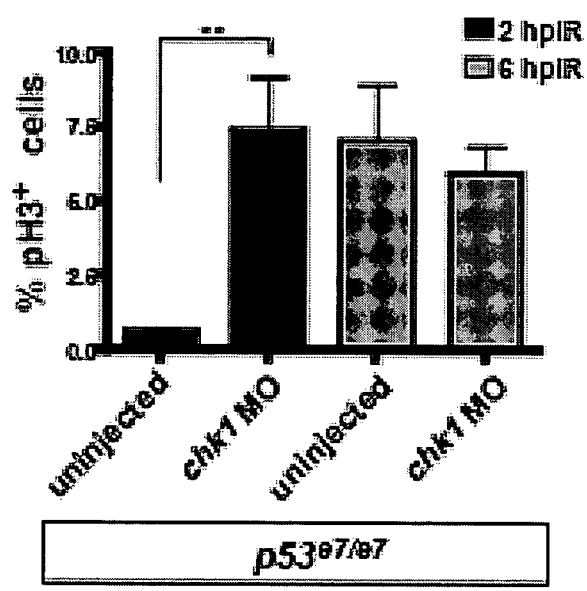

DNA content analysis of whole-embryo homogenates by flow cytometry showed that cells from irradiated chk1 morphants failed to accumulate in G2 at 6 hpIR, regardless of p53 status (FIGS. 4A & 4B). Failure to arrest in G$_2$ upon IR was also evident in toto, as whole-mount chk1$^{MO}$ embryos analyzed at 2 hpIR showed dramatically increased numbers of phospho-histone H3 (pH3)-positive cells (i.e., mitotic cells) compared with chk1$^{WT}$ embryos, again irrespective of their p53 genotype (FIGS. 4C & 4D). Consistent with a checkpoint defect, the mitotic phenotype of chk1$^{MO}$ embryos was only transient (FIG. 4D). These observations demonstrate that chk1 is essential for the IR-induced G$_2$ checkpoint in zebrafish, similar to its requirement in mammals and chick (Liu et al., 2000; Syljuasen et al., 2004; Zachos et al., 2003).

Figure 4E:
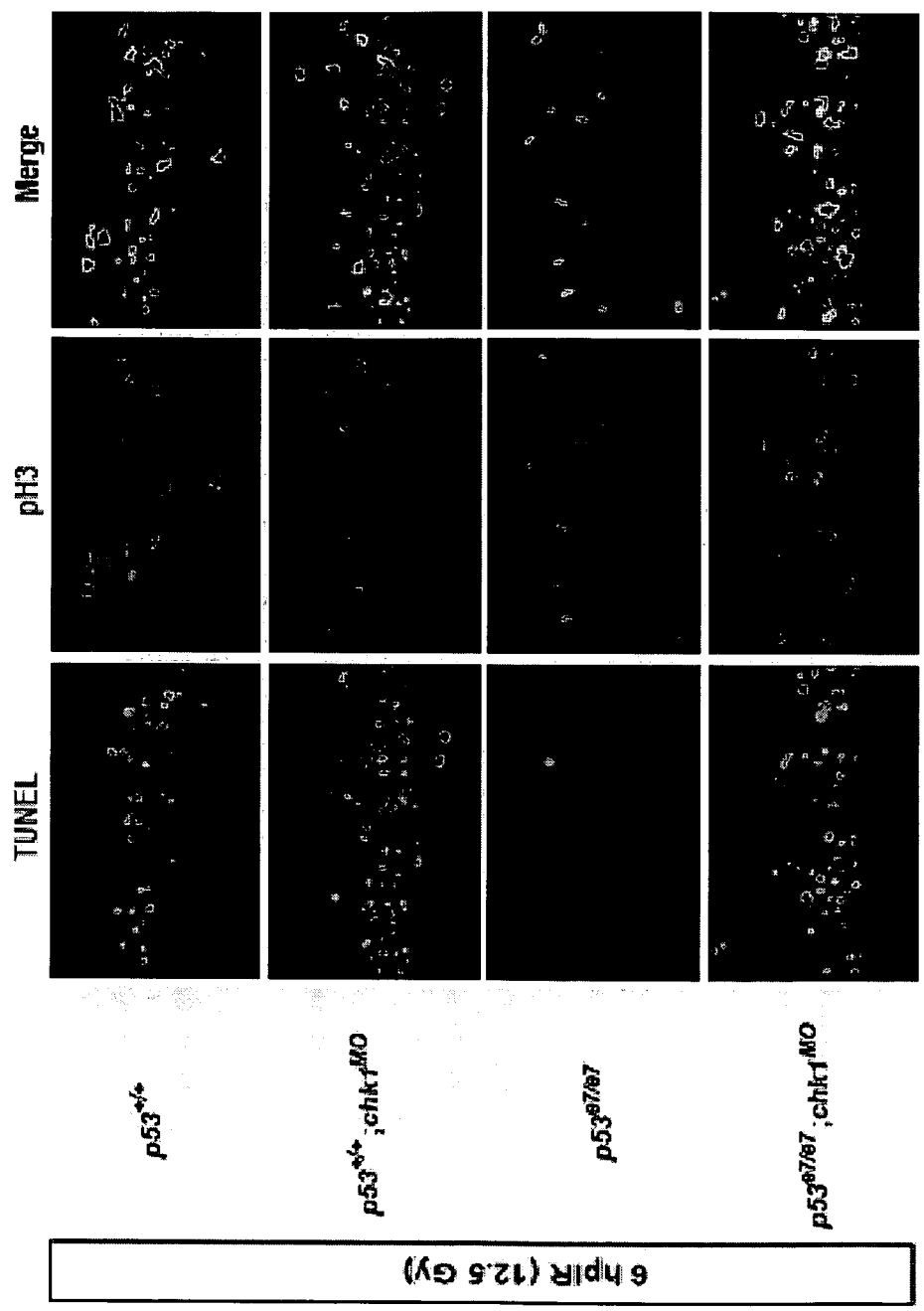
Figure 4F:

To test whether cells in irradiated p53$^{e7/e7}$;chk1$^{MO}$ embryos undergo mitotic catastrophe, we analyzed the spinal cords of TUNEL/pH3 double-labeled embryos by whole-mount confocal microscopy (FIGS. 4E & 4F). While approximately half of the pH3-labeled cells were TUNEL positive, the bulk of TUNEL-stained nuclei were pH3 negative, implying that death mainly occurred in other stages of the cell cycle. As a counter-example, cisplatin- or doxorubicin-induced death of MK-2-depleted Tp53$^{-/-}$ MEFs occurs in mitosis, exclusively (Reinhardt et al., 2007). While these in vivo observations do not formally invalidate the mitotic catastrophe hypothesis for p53-independent cell death following DNA damage in chk1-depleted cells, they strongly support a cryptic apoptotic pathway whose activation upon Chk1 depletion kills p53 mutant cells regardless of their cell cycle phase.

Chk1 Blocks a Mitochondria- and Death-Receptor-Independent Apoptotic Pathway Involving ATM, ATR and Caspase-2

Figure 5A:
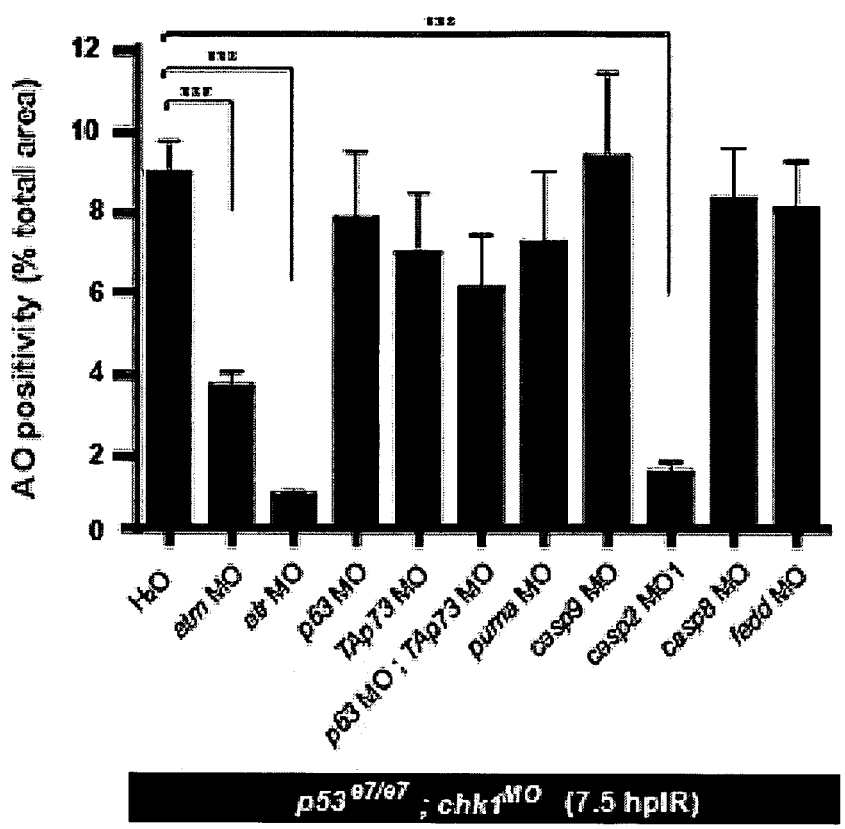
FIG. 5 provides two graphs, two sets of fluorescence images, a western blot image and a schematic diagram of two casp2 variants, which together illustrate genetic dissection of the zebrafish Chk1-suppressed apoptotic pathway. (A) Quantified AO labeling in spinal cords of 12.5 Gy-exposed $p53^{e7/e7}$;chk1$^{MO}$ embryos injected with $H_2O$ (bar on the far left) or the indicated MOs (x-axis). AO staining was quantified in ≥8 embryos per MO with a total of ≥100 embryos scored. All data are means+/−SEM. ***P<0.0001 (two-tailed Student's t-test). (B) Fluorescence images of representative embryos from the experiments shown in panel A. (C) Left, RT-PCR of casp2 transcripts from embryos either injected or not injected with casp2 MO. Right, schematics of caspase-2 protein variants (top, wild-type protein; bottom, predicted protein translated from exon 4-deleted transcripts). (D) Fluorescence images of embryos of the indicated genotypes with or without IR (12.5 Gy at 18 hpf), chk1 MO, or bcl-xl mRNA. Numbers in brackets refer to the corresponding bars in FIG. 5E below. (E) Quantified AO responses (n≥8) for embryos of indicated genotypes+/−bcl-xl mRNA. Light gray bars, $p53^{+/+}$ background; dark gray bars, $p53^{e7/e7}$;$chk1^{MO}$ background. Numbers in brackets refer to the representative-embryo images in FIG. 5D. Data are means+/−SEM.
Figure 5B:
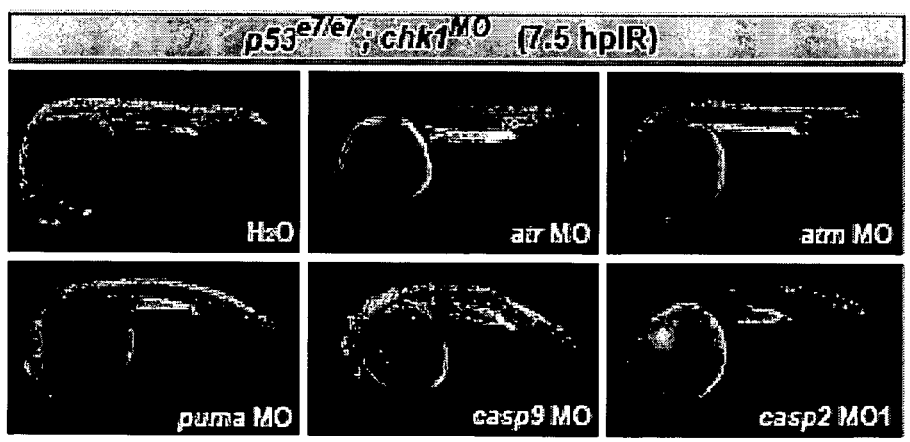

If, as our findings suggest, zebrafish embryos harbor a p53-independent apoptotic pathway whose activity is normally blocked by IR-activated Chk1, what are this pathway's DNA damage sensors, cell-death regulators and downstream effectors? To identify such molecules, we performed in vivo epistasis analyses in zebrafish by knocking down or forcing the expression of candidate pathway contributors in p53$^{e7/e7}$; chk1$^{MO}$ embryos.

atm and atr single knockdowns severely impaired chk1 knockdown-mediated radiosensitization of zebrafish p53 mutants, indicating that ATM and ATR are non-redundantly required to activate the p53-independent pathway after DNA damage (FIGS. 5A & 5B; p53$^{e7/e7}$;chk1$^{MO}$;atm$^{MO}$, ~60% reduction of the mean p53$^{e7/e7}$;Chk1$^{MO}$ response; p53$^{e7/e7}$; chk1$^{MO}$;atr$^{MO}$, ~90% reduction of the mean p53$^{e7/e7}$;chk1$^{MO}$ response). While single knockdowns of p63 and p73 failed to compromise IR-induced cell death in p53$^{e7/e7}$;chk1$^{MO}$ embryos, p53$^{e7/e7}$;chk1$^{MO}$;p63$^{MO}$;p73$^{MO}$ embryos showed a ~30% reduction in AO staining compared to control p53$^{e7/e7}$; Chk1$^{MO}$ embryos (FIG. 5A, bar 6), reminiscent of the reduction observed in p53$^{e7/e7}$;chk1$^{MO}$;chk2$^{MO}$ embryos (FIG. 10A, compare bars 3 and 5). Although borderline significant, the chk2 and p63,p73 knockdown data may reflect activation of p53-independent Chk2̄p63/p73 apoptotic pathways (Urist et al., 2004; Bernassola et al., 2005; Bernassola et al., 2004). Importantly, these modest knockdown effects—compared with atm or atr knockdowns—are unlikely to result from weaker MO efficiencies, as the chk2, p63 and p73 MOs lead to stronger gene knockdowns than the atm and atr MOs (FIGS. 2C & 11A-11C; also see Rentzsch et al., 2003). The inability of Chk2, p63 and p73 to account for the bulk of cell death events in irradiated p53$^{e7/e7}$;chk1$^{MO}$ embryos implies that ATM and ATR operate within a predominantly acting Chk2-independent apoptotic pathway, which, for simplicity, will be designated 'Chk1-suppressed pathway' ('CS' in FIG. 8D).

Figure 11A:
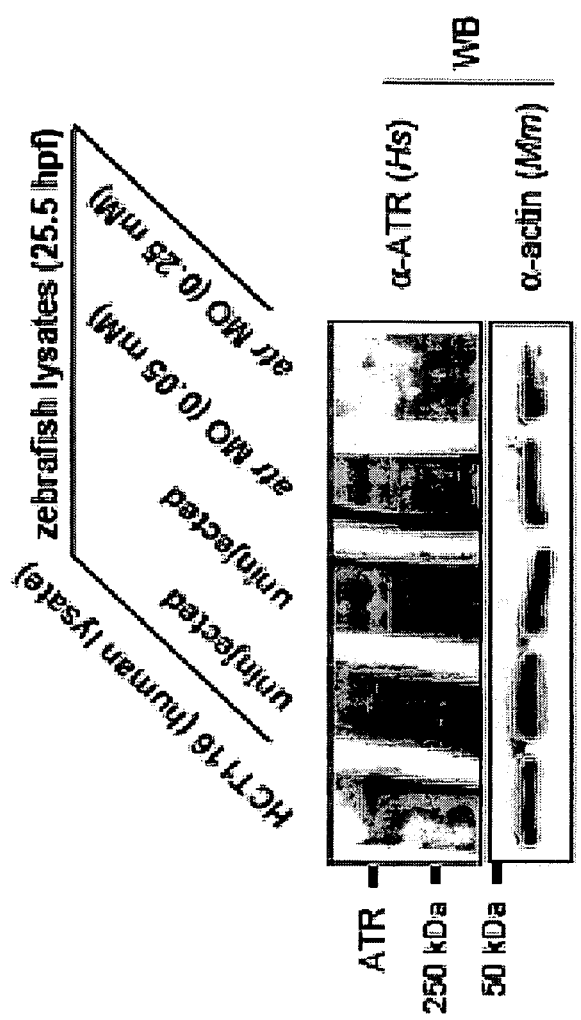
FIG. 11 provides a set of western blot images and four sets of DNA gel images demonstrating the knockdown efficiencies of selected MOs, plus corresponding schematic diagrams of predicted protein products. (A) Western blot of 25.5 hpf zebrafish protein lysates from non-injected and atr MO-injected embryos using an anti-human ATR antibody recognizing an internal peptide that is highly conserved in zebrafish Atr. Detection of a high molecular weight zebrafish band showing the same migration pattern as human ATR (lane 1) strongly supports crossreactivity of the antibody with zebrafish ATR (the predicted molecular weight of zebrafish ATR, 300 kDa, matches that of human ATR). Relative band intensities show that the specific atr MO (Stern et al., 2005) knocks downs zebrafish ATR levels in a dose dependent fashion. The MO concentration used in the MO screen (FIG. 1) and epistasis analyses (FIG. 5), 0.25 mM, leads to a >50% reduction in ATR levels compared to control (compare lanes 5 with 2 and 3). (B-E) Gel migration profiles of RT-PCR products from non-injected and MO-injected embryos using primers in exons flanking the targeted exon (Table 1). All bands were excised and sequenced. Predicted protein products are indicated at the right. All RT-PCRs are semi-quantitative with β-actin amplicon serving as loading control. (B) atm. Left primer is located in exon 54, right primer is located in exon 58 (Imamura and Kishi, 2005). The atm MO interferes with splicing at the intron 55/exon 56 splice junction, resulting in either retention of intron 55, deletion of exon 56, or both. Either aberrant splice product results in the occurrence of an inappropriate early stop codon (as a result of in-frame reading of the intron or of a frameshift caused by exon skipping), which is predicted to result in an early truncation of the ATM protein before the PIKK kinase domain. Numbers below the lanes refer to embryo morphology at 18 hpf. 1-3, 5: normal; 4, grossly affected or dead, incompatible with the IR/AO assay. Note that the atm MO concentration used in our study, which is compatible with the IR/AO assay, leads to an incomplete knockdown of atm. As exemplified in lane 4, this same MO concentration could lead to stronger knockdowns, but in this case the embryos could not be scored in the assay. (C) p63. Left primer is located in exon 2, right primer is located in exon 4. The p63 MO interferes with splicing at the exon3/intron 3 splice junction, resulting in retention of intron 3. This aberrant splice product results in the occurrence of an inappropriate early stop codon (as a result of in-frame reading of the intron), which is predicted to result in an early truncation of any p63 protein expressed from the p63 locus before the DNA binding domain (which is essential for the activities of both pro- and anti-apoptotic isoforms of p63). p63 MO strongly depletes the wild-type p63 mRNA pool, with the majority of transcripts retaining intron 3, leading to an efficient gene knockdown. (D) casp8. Left primer is located in exon 2, right primer is located in exon 4. The casp8 MO interferes with splicing at the exon3/intron 3 splice junction, resulting in retention of intron 3. This aberrant splice product results in the occurrence of an inappropriate early stop codon (as a result of in-frame reading of the intron), which is predicted to result in an early truncation of procaspase-8, thus removing part of the second DED domain and the entirety of the catalytic domain. casp8 MO both strongly depletes the wild-type casp8 mRNA pool and attenuates the levels of both wild-type and aberrant splice forms, resulting in a highly efficient gene knockdown. (E) casp9. Left primer is located in exon 1, right primer is located in exon 3. The casp9 MO interferes with splicing at the exon2/intron 2 splice junction, resulting in retention of intron 2. This aberrant splice product results in the occurrence of an inappropriate early stop codon (as a result of in-frame reading of the intron), which is predicted to result in an early truncation of procaspase-9, thus removing part of the CARD domain and the entirety of the catalytic domain. casp9 MO results in an incomplete, ~50% knockdown, but higher concentrations of the MO were either lethal prior to 18 hpf, or viable but extremely toxic to the embryos, precluding the analysis of epistatic relationships with chk1 and p53.
Figure 11B:
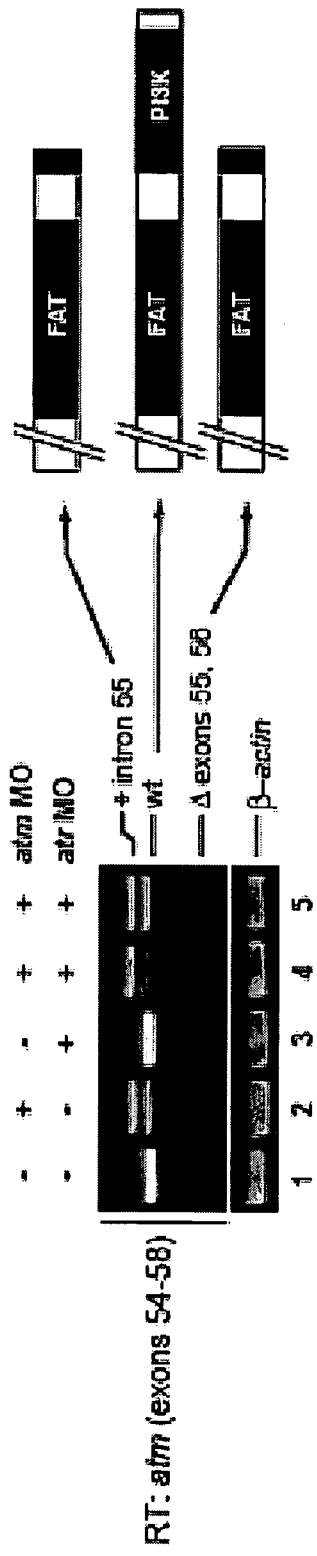
Figure 11C:
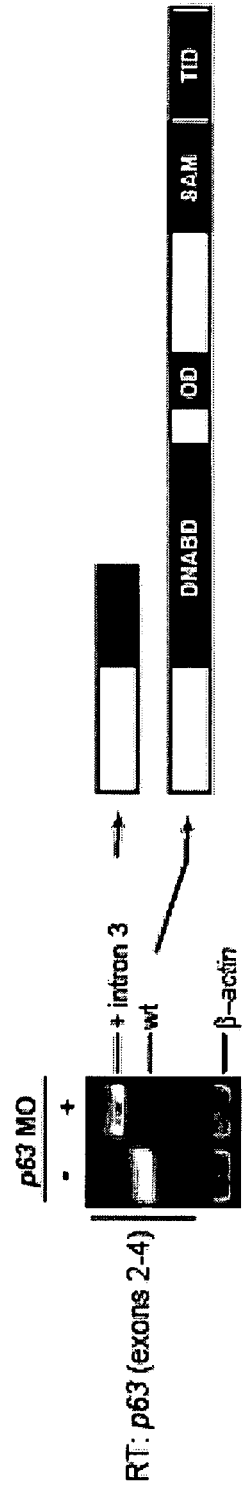
Figure 11D:
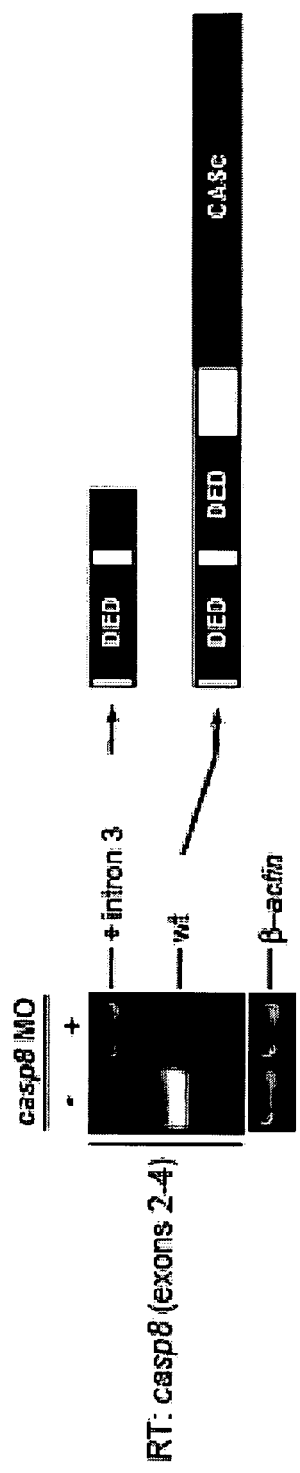
Figure 11E:
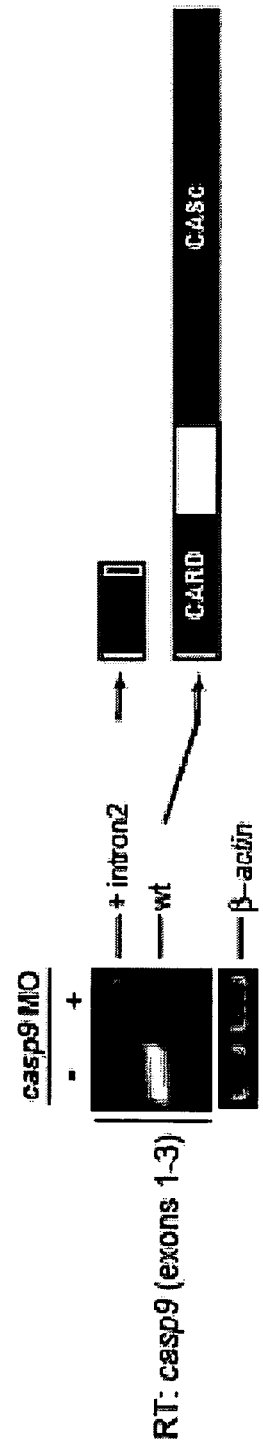
Figure 15:
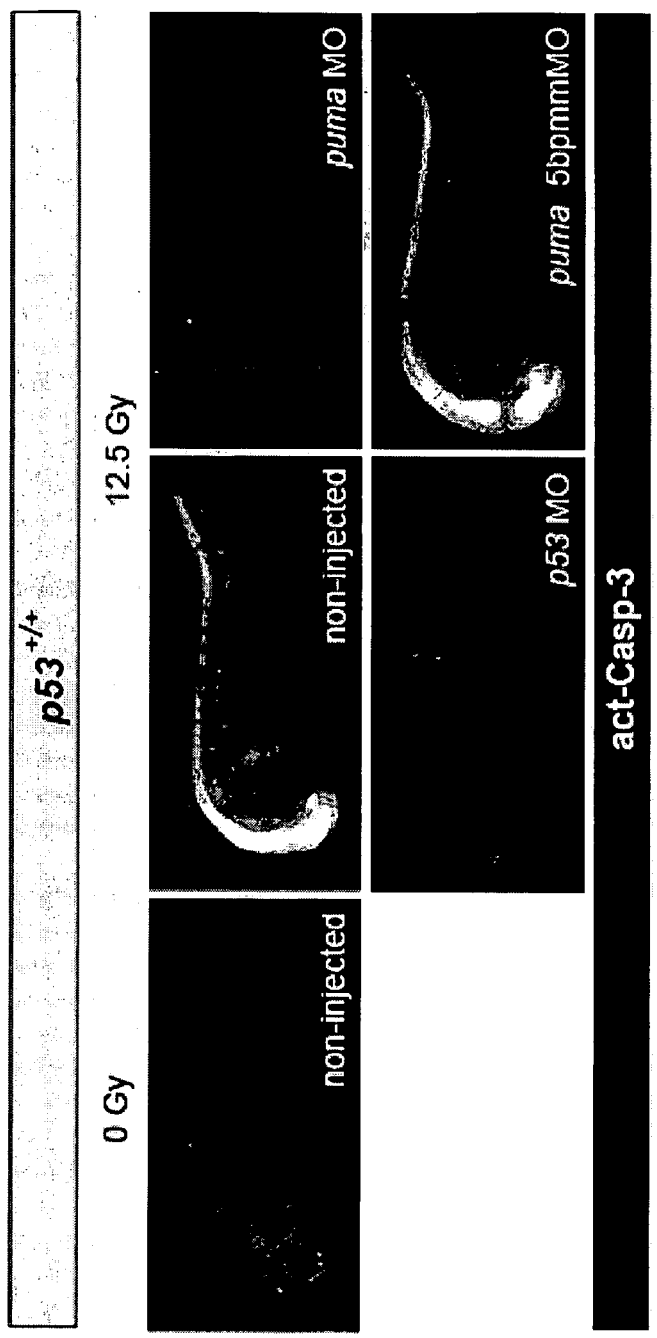
FIG. 15 provides a set of images of embryos, showing that puma depletion abrogates IR-induced apoptosis in wild-type zebrafish embryos. Lateral views of 25.5-hpf wild-type zebrafish embryos that were injected at the one-cell stage with the indicated MOs, irradiated (0- or 12.5-Gy) at 18 hpf, and immunostained with an anti-activated-caspase-3 antibody. The p53 MO-injected embryo serves as an internal control. Note that puma MO, but not puma 5 bpmmMO, produces a complete phenocopy of p53 MO.

To test whether the mitochondrial apoptotic axis contributes to the Chk1-suppressed pathway, we first knocked down the proapoptotic BH3-only family member Puma. puma depletion did not significantly affect AO labeling of irradiated p53$^{e7/e7}$;chk1$^{MO}$ embryos (FIGS. 5A & 5B) at a puma MO concentration that is otherwise sufficient to completely block IR-induced apoptosis in p53$^{+/+}$ zebrafish embryos (FIG. 15) (Kratz et al., 2006). Similarly, a dose of bcl-xl mRNA that completely blocked cell death 7.5 hpIR in wild-type embryos failed to affect the AO reactivity of irradiated p53$^{e7/e7}$;chk1$^{MO}$ embryos (FIGS. 5D & 5E; p53$^{+/+}$+bcl-xl, 0.035% of the mean p53$^{+/+}$ response; p53$^{e7/e7}$;chk1$^{MO}$+bcl-xl, ~95% of the mean p53$^{e7/e7}$;chk1$^{MO}$ response). A complete absence of effects was also evident after casp9 knockdown (FIGS. 5A, 5B & 11E). Thus, two major regulators of mitochondrial membrane permeabilization (Puma and Bcl-$x_L$) and the main initiator and effector caspases acting downstream of mitochondria (caspase-9 and caspase-3) are dispensable for the Chk1-suppressed apoptotic pathway.

The death-receptor axis bypasses the requirement for mitochondria and caspase-9, suggesting that it could contribute to the Chk1-suppressed pathway. In addition, a link between Chk1 loss and caspase-8 activation has recently been observed (Xiao et al., 2005). Even so, the death-receptor pathway converges on caspase-3 activation via caspase-8 initiator caspase activity (Hengartner, 2000; Lowe et al., 2004). This caspase-3 recruitment contrasts with the caspase-3-independence of the pathway we identified, which, together with the established cell-autonomy of the new pathway (FIG. 3E), argues against a role for death-receptor signaling downstream of chk1 depletion. Indeed, the AO reactivity of p53$^{e7/e7}$;chk1$^{MO}$;casp8$^{MO}$ zebrafish embryos did not differ from that of p53$^{e7/e7}$;chk1$^{MO}$ specimens (FIGS. 5A & 11D). Blocking death receptor signaling with a fadd MO (Eimon et al., 2006) also failed to affect AO staining (FIG. 5A). Thus, death-receptor signaling, like mitochondrial signaling, does not appear to play an important role downstream of chk1 knockdown.

Figure 5C:
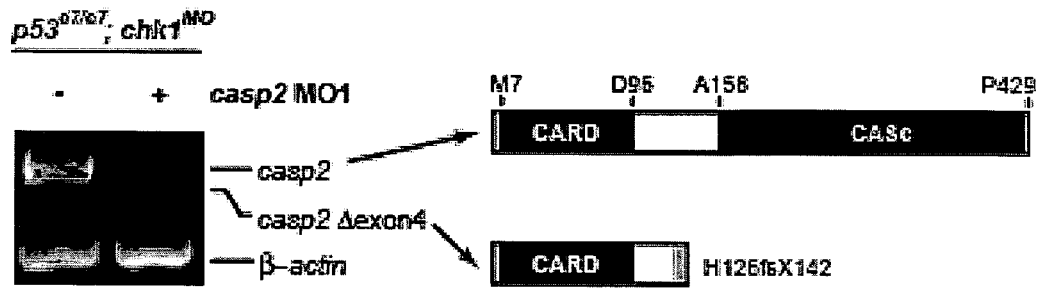
Figure 5D:
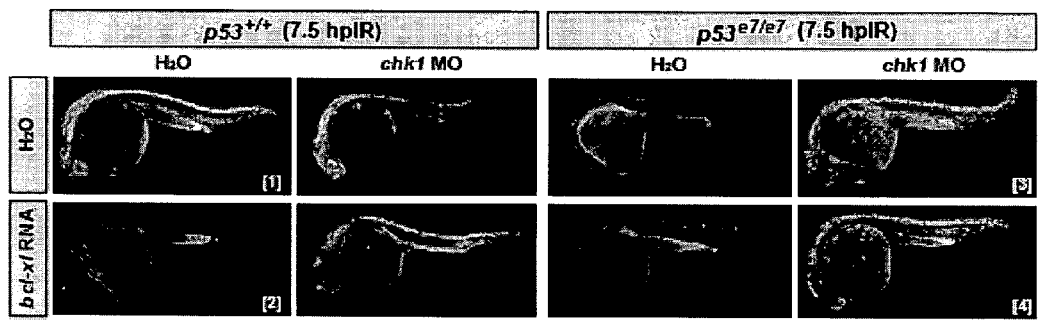
Figure 5E:
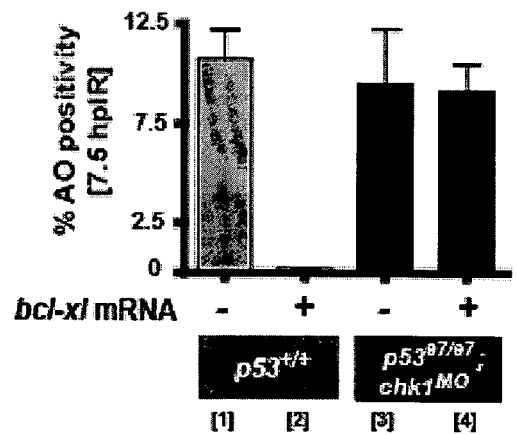
Figure 16A:
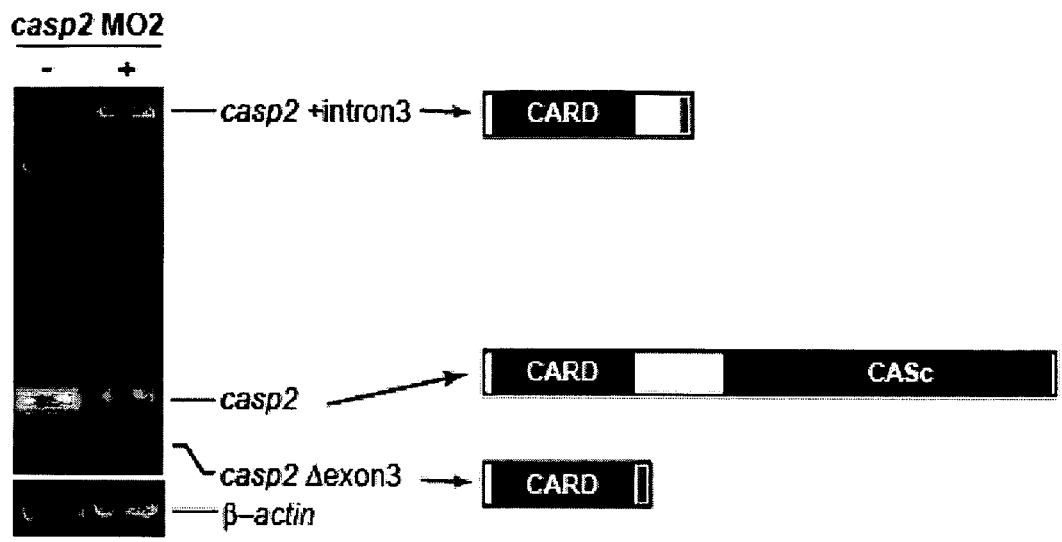
FIG. 16 provides a set of DNA gel images and a schematic illustration of corresponding gene products, and a graph, depicting the knockdown and radioprotective efficiencies of casp2 MO2 in $p53^{e7/e7}$;chk1$^{MO}$ embryos. (A) Gel migration profiles of RT-PCR products from non-injected and casp2 MO2-injected embryos using primers in exons flanking exon 3 (left primer is located in exon 2, right primer is located in exon 4). Predicted protein products are indicated at the right. (B) Quantified AO responses of irradiated (12.5 Gy) $p53^{e7/e7}$;chk1$^{MO}$ embryos that were non-injected (left) or injected with casp2 MO2 (right). AO staining was quantified in the spinal cords of ≥9 embryos per condition, with 50 embryos scored. The data are reported as means+/−SEM. Statistical significance estimated via a two-tailed Student's t-test.
Figure 16B:
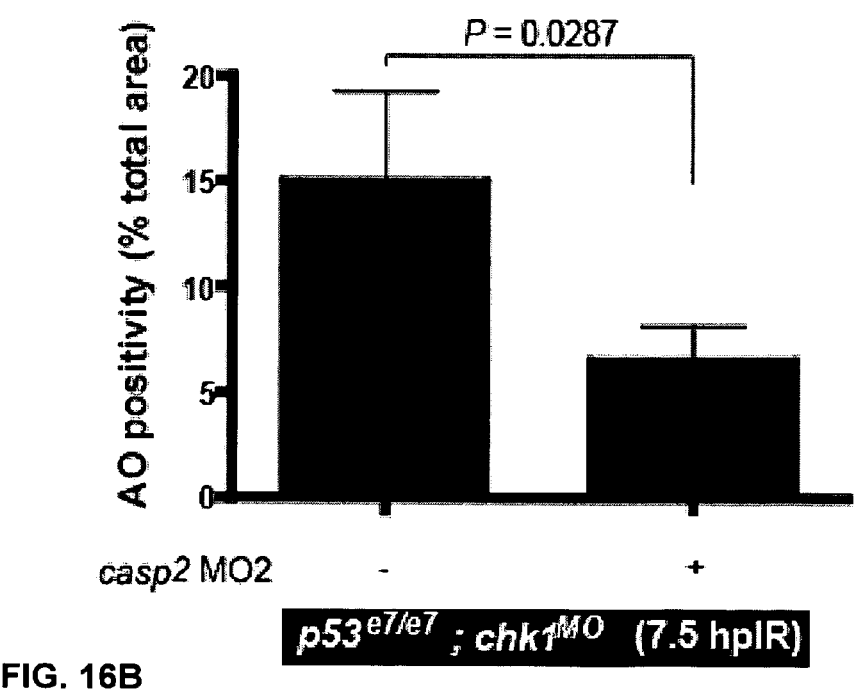

In fact, the sole caspase whose depletion blocked the Chk1-suppressed pathway was caspase-2, a poorly characterized yet highly conserved caspase with features of both initiator and executioner caspases (Troy and Shelanski, 2003; Zhivotovsky and Orrenius, 2005). In three separate experiments, p53$^{e7/e7}$;chk1$^{MO}$;casp2$^{MO1}$ embryos consistently showed a mean 6-fold decrease in AO labeling compared with p53$^{e7/e7}$;chk1$^{MO}$ embryos (—16% of the mean p53$^{e7/e7}$;chk1$^{MO}$ response, P<0.0001; FIGS. 5A & 5B). casp2 MO1, which targets the splice donor site of intron 4, led to marked reductions in casp2 mRNA levels and to aberrant residual transcripts lacking exon 4, predicted to encode an early truncated caspase-2 variant (FIG. 5C). A second casp2 MO significantly reduced IR-induced death in p53$^{e7/e7}$;chk1$^{MO}$ embryos (FIG. 16) and a mismatch version of casp2 MO1 had no effect. Altogether, these epistasis analyses identify an atm/atr-casp2 apoptosis-inducing program as a key mechanism through which Chk1 depletion radiosensitizer p53 mutant zebrafish embryos without recruiting the classical mitochondrial and death-receptor pathways (FIG. 8D).

The Chk1-Suppressed Apoptotic Pathway is Conserved in Human Cancer Cells

Figure 6A:
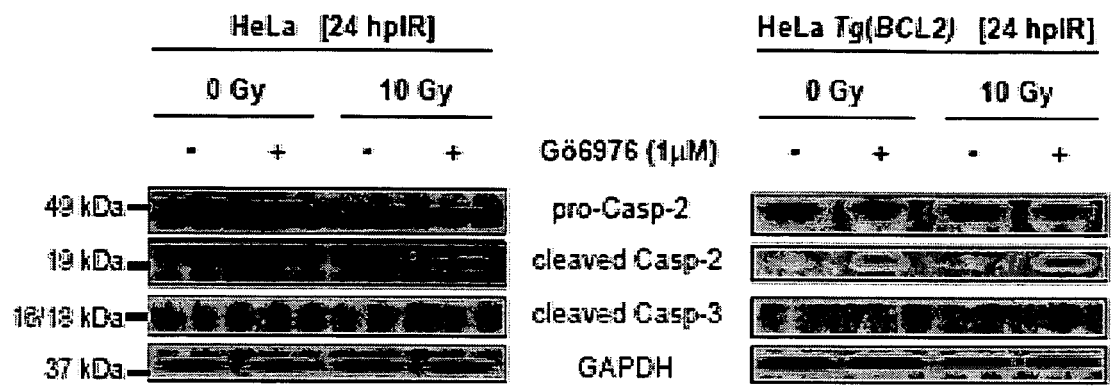
FIG. 6 provides a series of western blot images, three graphs and a set of florescence images as described below, demonstrating that the Chk1-suppressed pathway is conserved in HeLa cells. (A) Western blots comparing the levels of caspase-2 (pro- and cleaved forms) and cleaved caspase-3 at 24 hpIR in lysates from HeLa cells carrying or not carrying a BCL2 transgene (Tg(BCL2)), and treated with or without IR (10 Gy) or Chk1 inhibitor (Gö66976, 1 μM). (B) Analysis of HeLa cell survival at 72 hpIR (0 Gy vs 10 Gy) in the presence or absence of Gö6976 and/or BCL2. Note that Gö6976 radiosensitizes the cells ~2-fold regardless of the presence of the BCL2 transgene (compare bars 5 and 6, and bars 7 and 8). Also note that BCL2 is functional (i.e., confers radioprotection) in these experiments (compare lane 5 with lane 7). Data are means+/−SEM. (C) Fluorescence images of HeLa Tg(Cyt-c-GFP) cells with or without Tg(BCL2) or Gö6976 at 24 or 48 hpIR (10 Gy). Note the punctate GFP patterns in all 24-hpIR samples, and the diffuse GFP pattern in the 48-hpIR sample. (D) Gö6976 inhibits Chk1, but not MK-2, in HeLa cells at 24 hpIR (10 Gy). Western blots comparing the activities of Chk1 (Cdc2 phosphorylation at Tyr15 and CDC25C phosphorylation at Ser216) and MK-2 (Hsp-27 phosphorylation at Ser82) following exposure to increasing concentrations of Gö6976. Blots using antibodies against native Hsp-27 and Gapdh are shown as internal controls. (E) Hsp-27 is a bona fide substrate of MK-2 in HeLa cells. Western blot of lysates from irradiated HeLa cells exposed to increasing concentrations of the p38MAPK specific inhibitor SB203580 (Reinhard et al., 2007), showing a reduction in the abundance of phosphorylated Hsp-27 at Ser82 compared to native Hsp-27, as detected with specific antibodies. (F) Levels of cleaved caspase-2 and caspase-3 at 24 hpIR (10 Gy) in HeLa cells transfected with LACZ or CHK1 siRNAs at 72 hours before IR. (G) Knockdown efficiencies of the indicated shRNAs as measured by western blots with anti-caspase-2 and -3 antibodies. Note that none of the CASP2 shRNAs affect caspase-3 levels, that CASP2 shRNA(3) is less effective than shRNAs 1 and 2, and that the CASP3 shRNA does not affect caspase-2 expression. (H) Effects of GFP, CASP2 and CASP3 shRNAs on apoptotic cell numbers at 48 hpIR as measured by AnnexinV (+)/PI (−) staining of HeLa cells treated with 10 Gy with or without Gö6976 (1 μM). For each shRNA, the average apoptotic cell number (given as % of GFP shRNA control) is shown. All data are means+/−SD. **P<0.01 (two-tailed Student's t-test). Asterisks on top of bars refer to comparisons with GFP shRNA. (I) TUNEL reactivity of HeLa cells harboring a GFP or CASP2 shRNA after 0 or 10 Gy IR with or without Gö6976 (1 μM). The cell cycle distribution of TUNEL positive cells, assessed by PI co-labeling (see FIG. 16 for details), is shown. All data are means+/−SEM. *P<0.05 (two-tailed Student's t-test). (J) Synergistic activation of ATM and ATR by Gö6976 and IR. Western blots comparing the activities of ATM (Chk2 phosphorylation at Thr68) and ATR (Chk1 phosphorylation at Ser317) after 0 or 10 Gy IR with or without Gö6976 (1 μM). Blots using antibodies against native Chk2 and Chk1 are shown as internal controls. Bottom blot, levels of DNA damage as detected by an antibody recognizing phosphorylated H2A.X at Ser139.
Figure 6B:
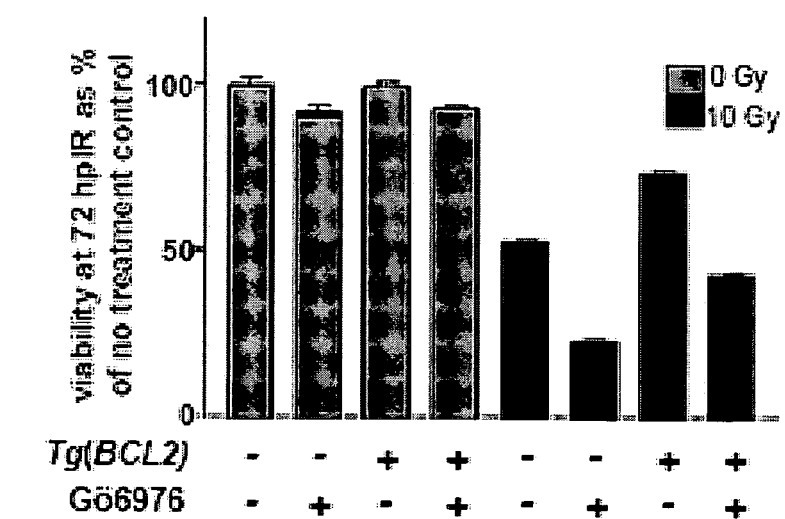
Figure 6C:
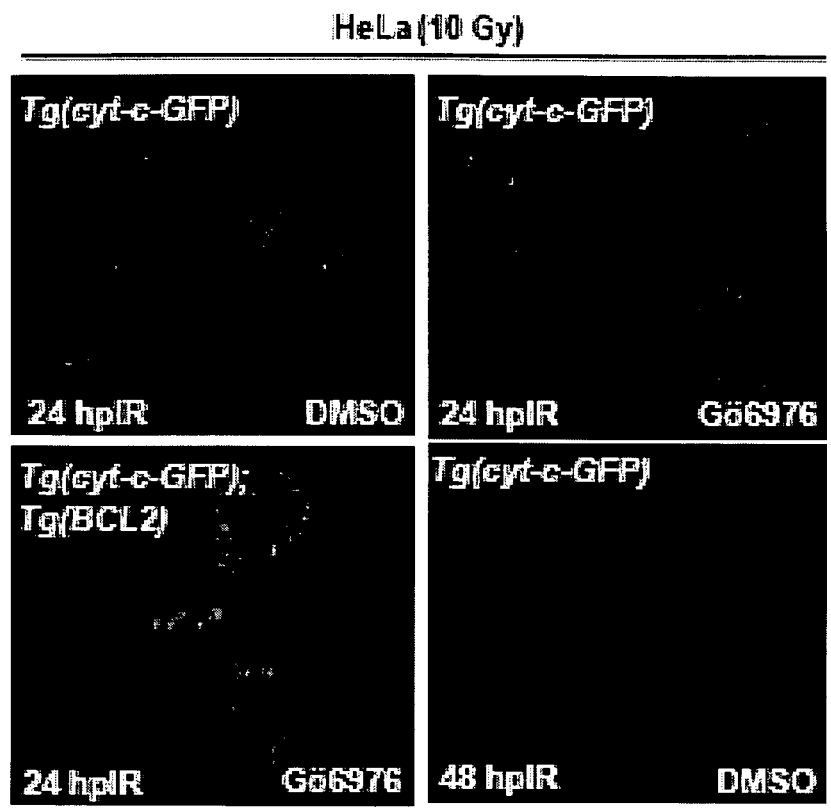

We next investigated whether the zebrafish Chk1-suppressed pathway is conserved in human cancer cells defective in p53 signaling. To inhibit Chk1 in these cells, we used the indolocarbazole Gö6976 (Kohn et al., 2003), which has much greater specificity than the commonly used Chk1 inhibitor UCN-01 (7-hydroxystaurosporine) (reviewed in Kawabe, 2004, and see below). In HeLa cells (in which the p53 protein pool is depleted by HPV-18 E6), caspase-2 cleavage was readily apparent at 24 hpIR in the presence of Gö6976 (FIG. 6A). This effect was synergistic, because neither IR nor Gö6976 alone caused substantial increases in cleaved caspase-2 levels compared to basal levels seen in control cells (FIG. 6A). In addition, caspase-2 cleavage tightly correlated with a strong radiosensitizing effect (~50% cell killing; FIG. 6B, compare bars 5 and 6; see also FIGS. 6I & 7C). By contrast, the levels of cleaved caspase-3 in Gö6976-treated cells at 24 hpIR were negligible and did not differ from those observed in irradiated cells not exposed to the inhibitor (FIG. 6A). Furthermore, both caspase-2 cleavage and concomitant cellular radiosensitization were insensitive to overexpression of human BCL2, whereas caspase-3 cleavage was completely removed in this context (FIGS. 6A & 6B, compare bars 7 and 8). Synergistic activation of caspase-2 by Gö6976 and IR did not elicit or involve cytochrome c (Cyt-c) release from the mitochondria at 24 hpIR, as visualized in HeLa cells expressing a cyt-c-GFP transgene (FIG. 6C) (Goldstein et al., 2000). Together, these first observations showed that Chk1 inhibition and IR synergize to activate caspase-2 and trigger BCL2- and mitochondria-independent cell death in p53-defective human cells.

Figure 6D:
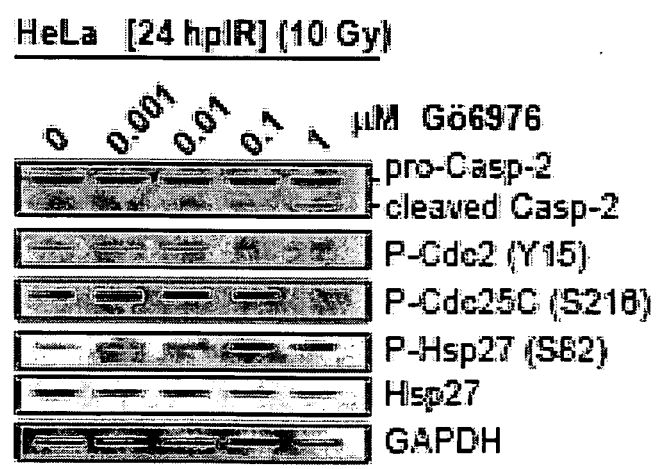
Figure 6E:
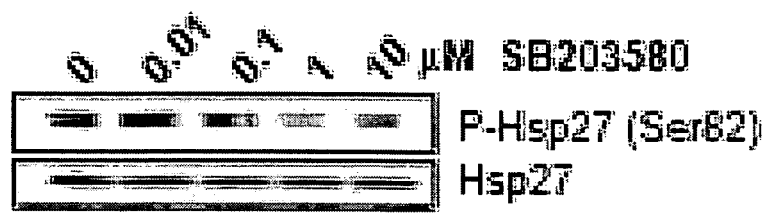
Figure 6F:
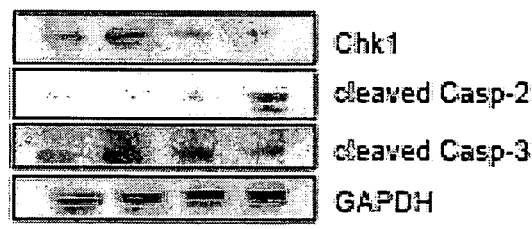

Before testing whether caspase-2 is required for cell death induction, we verified the specificity of Gö6976 as an inhibitor of Chk1. CHK1 siRNA, but not a LACZ control siRNA, induced caspase-2 cleavage in synergy with IR at 24 hr post-treatment but did not stimulate caspase-3 processing at this stage, in accordance with the effects of Gö6976 (FIG. 6F). We next tested the effects of Gö6976 on MK-2 activity. Indeed, it has recently been shown that UCN-01, a structural relative of Gö6976, inhibits both Chk1 and MK-2 at a concentration that was initially thought to specifically inhibit Chk1 (Reinhardt et al., 2007). Given that MK-2 knockdown phenocopies the chemosensitizing effects of CHK1 knockdown in p53-deficient mammalian cells (Reinhardt et al, 2007), the effects of Gö6976 on caspase-2 cleavage might result, at least in part, from MK-2 inhibition. However, while Gö6976 inhibited the phosphorylation of CDC2 and CDC25C (a direct Chk1 substrate) in a dose-dependent fashion, it did not block HSP-27 phosphorylation at serine 82 (the same MK-2 phosphorylation site that was analyzed by Reinhardt et al.) (FIG. 6D). In fact, at the 1 µM concentration of Gö6976 used throughout our studies, we observed an increase in MK-2 activity, alongside potent Chk1 inhibition and caspase-2 activation (FIG. 6D). Combined with the CHK1 siRNA data, these results establish Gö6976 as a specific Chk1 inhibitor in our experimental setting.

Figure 6G:
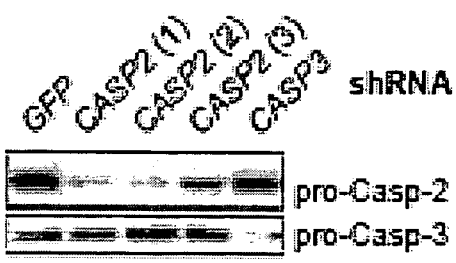
Figure 6H:
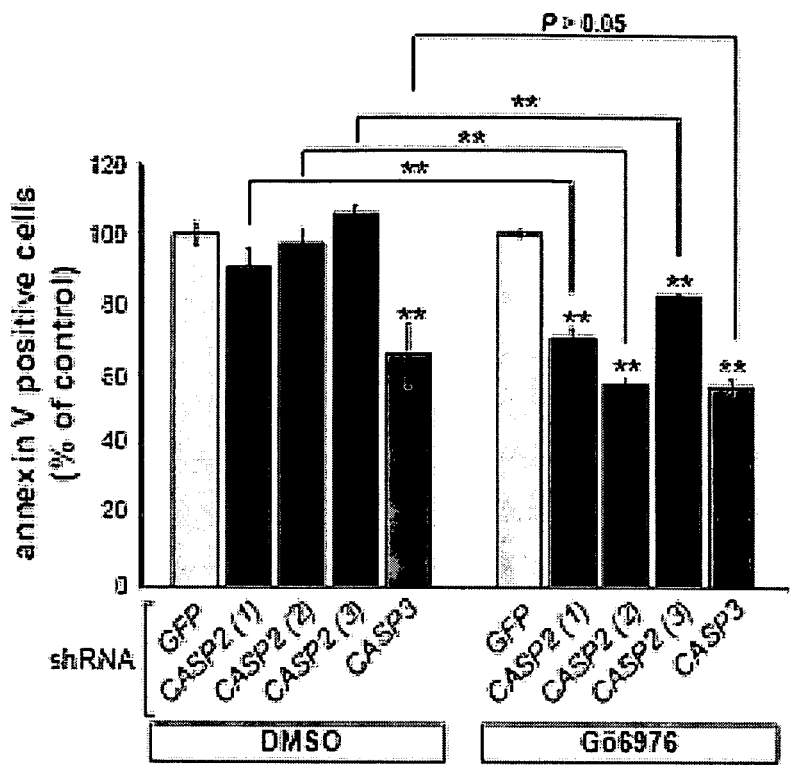
Figure 6I:
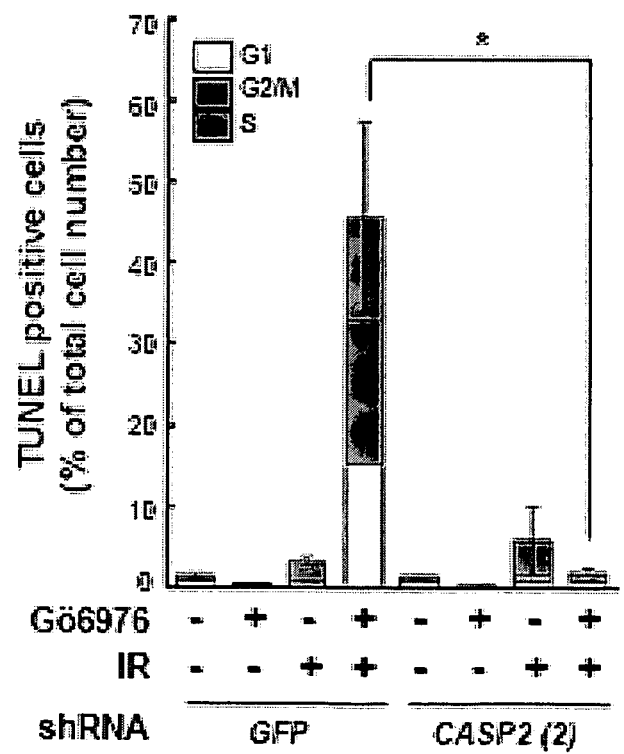

To directly test whether caspase-2 is required for Gö6976-mediated HeLa cell killing after IR, we used three independent CASP2 shRNAs that produced strong and specific knockdowns (FIG. 6G; note that caspase-3 levels are unaffected by the CASP2 shRNAs). All three CASP2 shRNAs significantly impaired apoptosis induction at 48 hours after IR+Gö6976 treatment, but not after IR treatment alone (FIG. 6H; see also FIG. 6I). In contrast, the reduction in apoptosis observed upon CASP3 knockdown at 48 hours (stage at which caspase-3 is eventually cleaved) was independent of Gö6976, as CASP3 shRNA led to a similar attenuation after IR treatment alone (FIG. 6H, compare bars 1 and 5, and 6 and 10, respectively). The severity of the apoptotic blockades caused by the CASP2 shRNAs (20-45% reductions, P<0.01 for each) tightly correlated with their respective knockdown efficiencies (FIGS. 6G & 6H).

Altogether, these results demonstrate that caspase-2, but not caspase-3, is specifically required for apoptosis induction following Chk1 inhibition in irradiated human cancer cells, similar to its requirement in irradiated p53$^{e7/e7}$;chk1$^{MO}$ zebrafish embryos.

Figure 17:
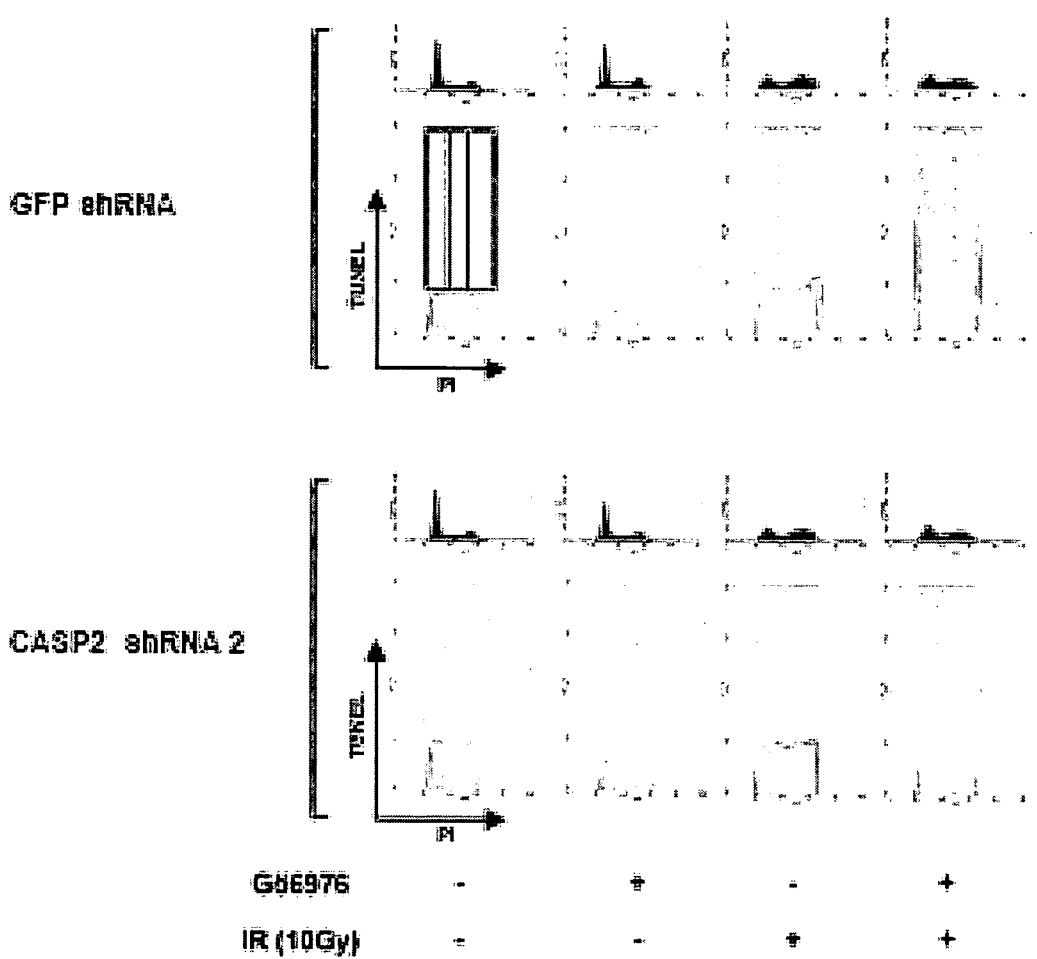
FIG. 17 depicts a series of histograms, showing cell cycle distribution of apoptotic HeLa cells after IR+Gö6976 treatment. HeLa cells stably expressing GFP or CASP2 shRNAs and treated with or without 10 Gy IR with or without Gö6976 (1 µM), as indicated at the bottom, were incubated with DNA labeling buffer containing TdT and BrdU, and stained with FITC-conjugated anti-BrdU antibody and PI. For each shRNA line, upper panels show PI-single histograms and lower panels show PI/TUNEL double-staining images. Cell cycle distribution was determined by DNA content (PI: X-axis), and TUNEL (Y-axis)-positive cells in each fraction were quantified (FIG. 6I). The box in the first double-staining image marks TUNEL positive cells and is included for illustrative purposes. Cells below the rectangle are TUNEL negative. The threshold for TUNEL positivity (lower horizontal line of the box) was determined as the maximal TUNEL signal observed in non-treated cells of the founder HeLa line. Vertical lines of the box demarcate cell cycle phases, according to DNA content (X-axis): cells on the left, 2N (G1); cells inbetween, S phase; cells on the right, 4N (G2/M). Note the dramatic increase in TUNEL positive shGFP cells after IR+Gö6976 treatment compared to single- or no-treatment controls, and the complete absence of TUNEL positive cells in the double-treated shCASP2 cells. Also note that TUNEL positive shGFP cells are evenly distributed throughout the cell cycle.

Our experiments in zebrafish suggested that the Chk1-suppressed pathway does not mediate mitotic catastrophe, and rather fires apoptosis regardless of cell cycle phase (FIG. 4E). Examination of Gö6976+IR-treated HeLa cells by PI/TUNEL double labeling revealed that apoptotic cells were evenly distributed throughout the cell cycle (FIGS. 6I & 17). Strikingly, caspase-2 knockdown eliminated TUNEL reactivity in G1, S and G2/M altogether (FIG. 6I, compare bars 4 and 8; FIG. 17). Thus, cell-cycle phase independence is another feature of the Chk1-suppressed pathway that is evolutionarily conserved.

Figure 6J:
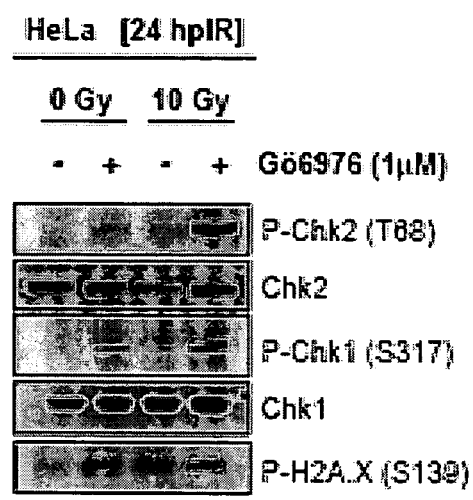
Figure 18A:
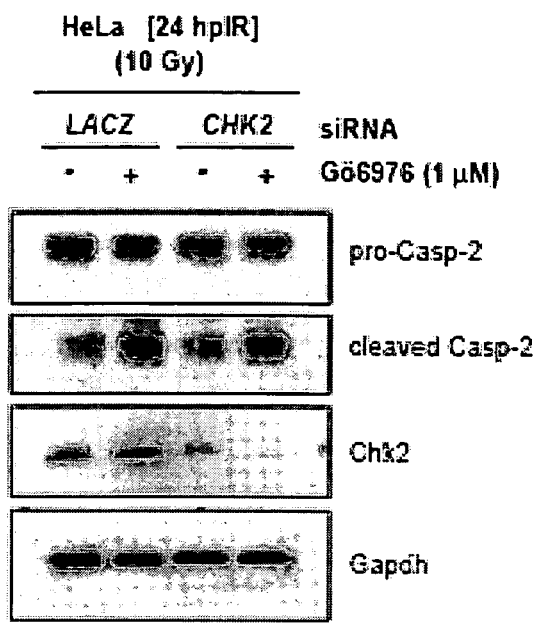
FIG. 18 provides a set of western blot images and a graph, showing that CHK2 siRNA fails to block caspase-2 cleavage and subsequent cell death induced by IR+Go6976 treatment. (A) Western blot showing the levels of pro- and cleaved caspase-2 at 24 hpIR (10 Gy) in HeLa cells that were treated or not treated with Gö6976 for 24 hr, and that were transfected at 72 hr prior to treatment with siRNAs against LACZ or CHK2. Whereas the CHK2 siRNA strongly knocked down Chk2, it failed to block caspase-2 cleavage. (B) Analysis of HeLa cell survival at 72 hpIR (0 Gy vs 10 Gy) in the presence or absence of Gö6976 (1 µM) and in the presence of a LACZ or CHK2 siRNA as indicated. Whereas CHK2 siRNA confers protection to IR alone, it fails to protect cells treated with both IR and Gö6976.
Figure 18B:
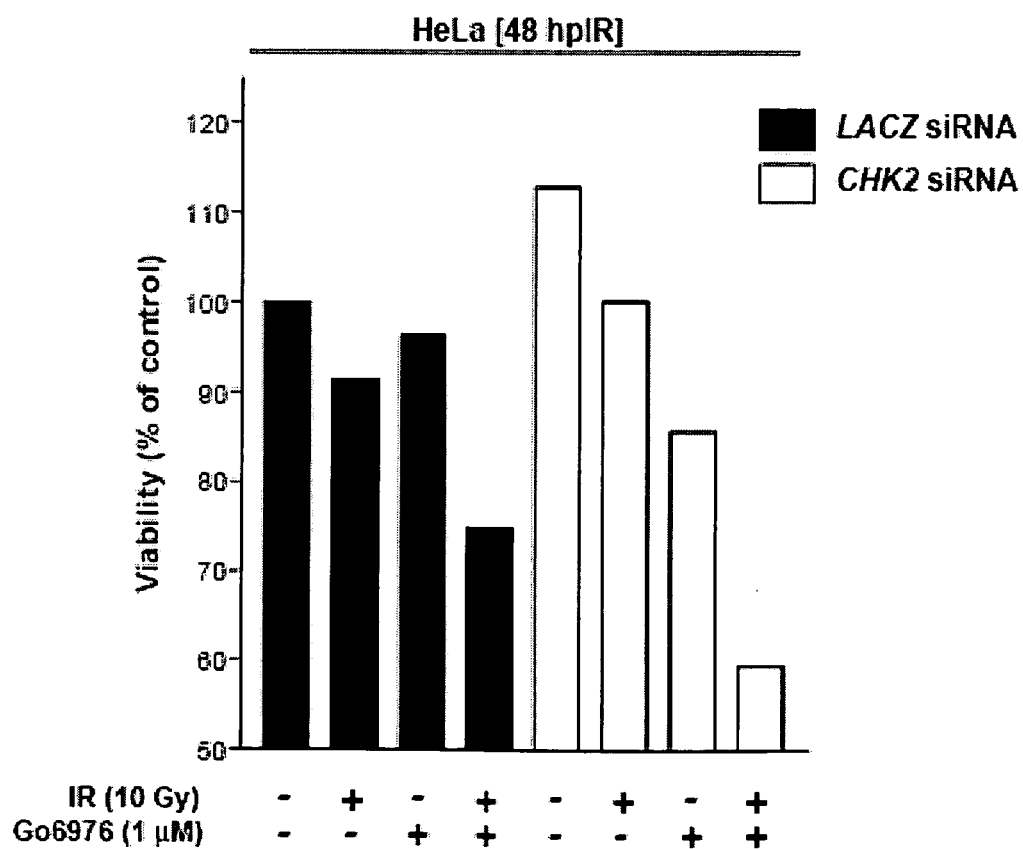
Figure 19A:
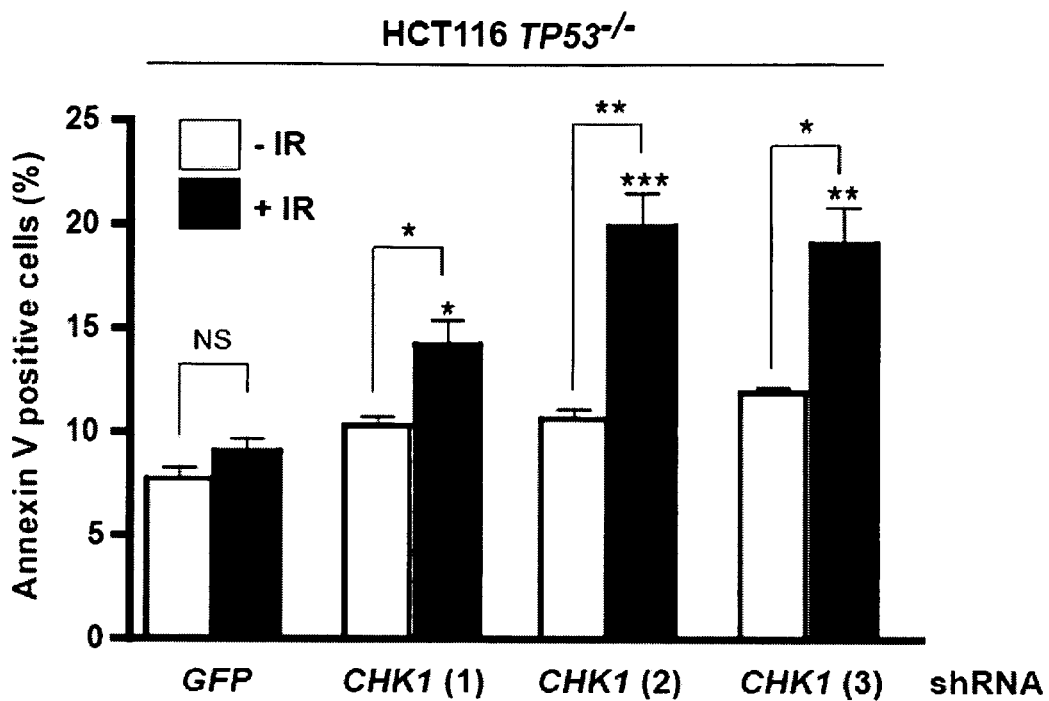
FIG. 19 provides a graph, showing CHK1 shRNAs phenocopy Go6976 in HCT116 cells, and corresponding western blot images as described below. (A) Apoptotic cell numbers at 48 hpIR as measured by Annexin V (+)/PI (−) staining of cell lines expressing the indicated shRNAs. Cells were treated with 0 or 10 Gy IR as indicated. All data are means+/−SEM. (B) Western blot comparing the levels of Chk1 and cleaved caspase-2 in 24-hpIR lysates from the experiment shown in FIG. 19A.
Figure 19B:
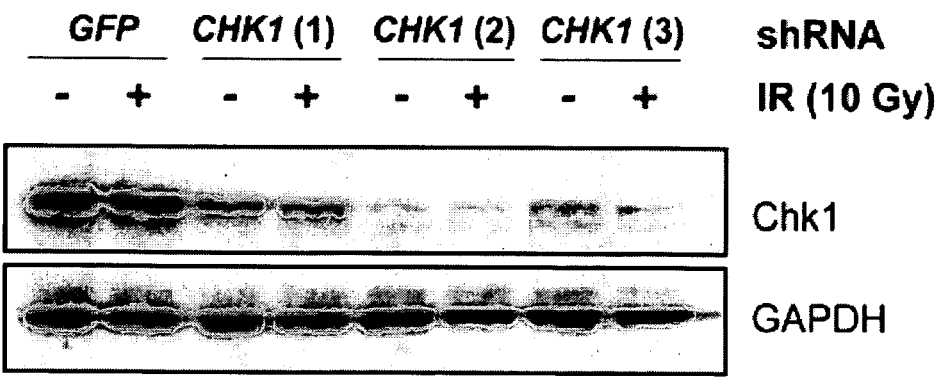

If the ATM/ATR-caspase-2 apoptotic axis we describe in zebrafish were effectively conserved in human cells, ATM and ATR should be activated after Chk1 inhibition in irradiated HeLa cells, similar to caspase-2. Indeed, IR+Gö6976 treatment led to synergistic increases in phosphorylated Chk2 at Thr68 (readout for ATM activity), and phosphorylated Chk1 at Ser317 (readout for ATR activity) (FIG. 6J). Elevated ATM and ATR activities correlated with increased levels of DNA damage in the IR+Gö6976-treated cells, as revealed by an increased abundance of phosphorylated H2A.X (FIG. 6J). Even though Chk2 was strongly activated in this context (FIG. 6J), a specific CHK2 siRNA failed to block caspase-2 activation (FIG. 18). This result confirms our prediction, based on epistasis analyses in zebrafish, that the Chk1-suppressed pathway is Chk2-independent (see FIG. 8D). Taken together, our experiments in HeLa cells show that apoptosis after IR+Gö6976 treatment of human cells involves ATM and ATR activation, is independent of Chk2, Bcl-2, mitochondria and caspase-3, but requires caspase-2 activation and function. Thus, the zebrafish Chk1-suppressed pathway is evolutionarily conserved in human cancer cells.

Figure 7A:
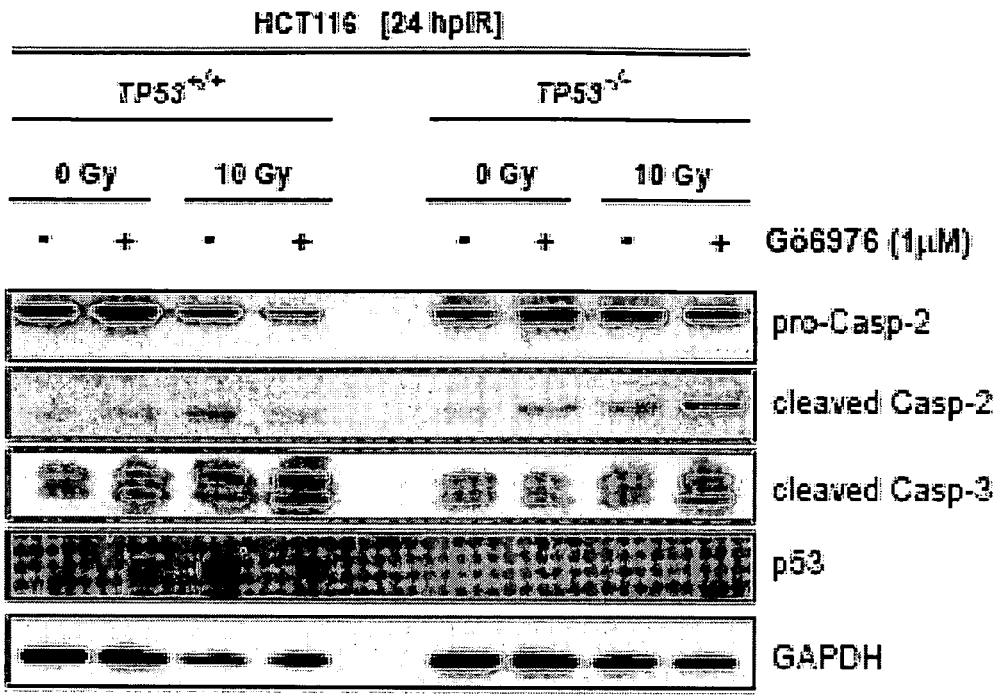
FIG. 7 provides five sets of western blot results and two sets of graphs as outlined below, demonstrating the influence of p53 genotype and IR dose on Gö6976-mediated radiosensitization of human cancer cells. (A) Western blots comparing the levels of caspase-2 (pro- and cleaved forms) and cleaved caspase-3 in 24-hpIR lysates from $TP53^{+/+}$ and $TP53^{-/-}$ HCT116 cells that were treated with or without IR (10 Gy) or Gö6976 (1 μM). (B) Western blots comparing the levels of caspase-2 (pro- and cleaved forms) and cleaved caspase-3 in 24-hpIR lysates from SAOS2 (left), MDA-MB-435 (middle) or LN-428 (right) cells that were treated with or without IR (10 Gy) or Gö6976 (1 μM). (C) Apoptotic cell numbers at 48 hpIR as measured by Annexin V (+)/PI (−) staining of the indicated cell lines treated with 0 or 10 Gy IR with or without Gö6976 (0.5 μM, treatment protocol as outlined in panel F). All data are means+/−SEM. (D) Western blot comparing the levels of cleaved caspase-2 in 24-hpIR lysates from HeLa cells that were irradiated with 0, 2, 3.2 or 10 Gy, and treated with or without Gö6976 (1 μM; standard treatment protocol, as shown above blot). (E) Western blot comparing the levels of cleaved caspase-2 in 24-hpIR lysates from HeLa cells that were treated with 0, 3.2 or 10 Gy, with or without Gö6976 (1 μM; lanes 1 and 2, inhibitor administered 6 hbIR; lanes 3 and 4, standard treatment protocol). (F) Western blot comparing the levels of cleaved caspase-2 in 24-hpIR lysates from HeLa cells that were irradiated with 0, 2, 3.2 or 10 Gy, and treated with or without Gö6976 (500 nM; inhibitor administered 24 hbIR, as outlined above blot). (G) Clonogenic survival of HeLa cells after 0, 2, 3.2 or 10 Gy IR. Colonies were counted 14 dpIR. White bars, DMSO-treated. Black bars, Gö6976-treated (500 nM; inhibitor administered 24 hbIR, as outlined in FIG. 7F). Note that caspase-2 knockdown eliminates the radiosensitizing effect of Gö6976 at 3.2 Gy. All data are means+/−SEM. *P<0.05 (two-tailed Student's t-test).
Figure 7B:
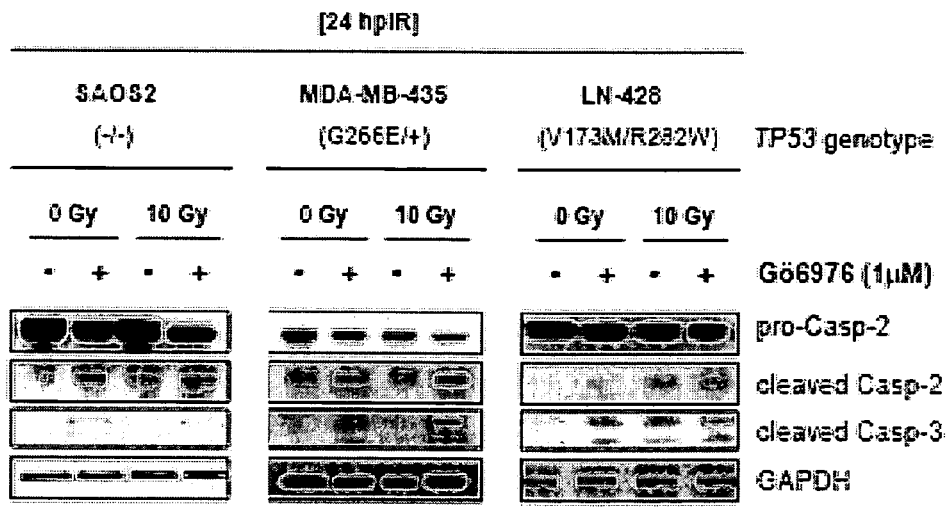
Figure 7C:
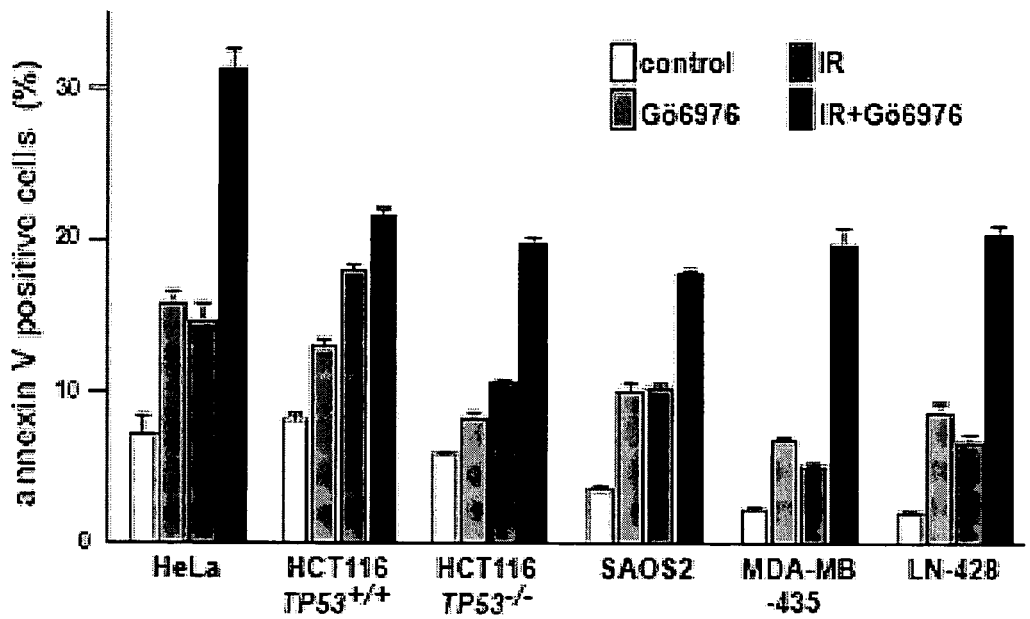

Next, we asked whether the Chk1-suppressed pathway could be triggered in other human cancer cell lines with various p53 genotypes. We tested TP53$^{+/+}$ and TP53$^{-/-}$ $^{HCT}$116 colon carcinoma cells (Bunz et al., 1998), the SAOS2 osteosarcoma line (p53 null), the MDA-MB-435 breast cancer line (heterozygous for the G266E mutation) and LN-428 glioblastoma cells, which are V173M/R282W transheterozygotes (Ishii et al., 1999). All TP53 null or mutant lines tested displayed increases in caspase-2 cleavage and apoptosis after IR+Gö6976 treatment compared to single- or no-treatment controls (FIGS. 7A-7C & 19). While these observations are in accordance with the results in HeLa cells, we noted several differences. First, TP53$^{+/+}$ HCT116 cells failed to engage the Chk1-suppressed pathway, as evidenced by their inability to cleave caspase-2 after IR+Gö6976 treatment (FIG. 7A; see also Discussion). Instead, Gö6976 synergized with IR to activate caspase-3 and induce a moderate, yet significant increase in apoptosis (FIGS. 7A & 7C). caspase-3 activation in these cells was p53-dependent, because only marginal caspase-3 cleavage could be detected in their TP53$^{-/-}$ counterparts (FIG. 7A). Therefore, Gö6976 can communicate with caspase-3 after IR, likely through a classic p53-mitochondria pathway. Intriguingly, MDA-MB-435 and LN-428 cells also engaged caspase-3 cleavage after IR+Gö6976 treatment (FIG. 7B). This caspase-3 cleavage could result from p53-independent apoptotic processes operating in parallel with the newly identified Chk1-suppressed pathway (such as the Chk2-p63/73 axis), or from caspase-2 itself triggering the mitochondrial or extrinsic axes (e.g., Shin et al., 2005; Tinel and Tschopp, 2004). However, it is unlikely that any of these alternative pathways substitute for the Chk1-suppressed pathway in HeLa, SAOS2 or TP53$^{-/-}$ HCT116 lines, in which caspase-3 cleavage is undetectable (or marginal) after IR+Gö6976 treatment (FIGS. 6A, 7A & 7B).

Combining Gö6976 with Therapeutic Doses of IR is Sufficient to Activate the Chk1-Suppressed Pathway As shown in FIG. 6, combining Gö6976 with 10 Gy IR robustly triggers the Chk1-suppressed pathway in HeLa cells. While doses up to 45-60 Gy are common in radiotherapy, the total dose is usually given in 20-30 courses of 2 Gy (conventional therapy), or up to 3.2 Gy in hypofractionated therapies (REFS). We tested whether such therapeutic doses suffice to enable activation of the Chk1-suppressed pathway by Gö6976.

Figure 7D:
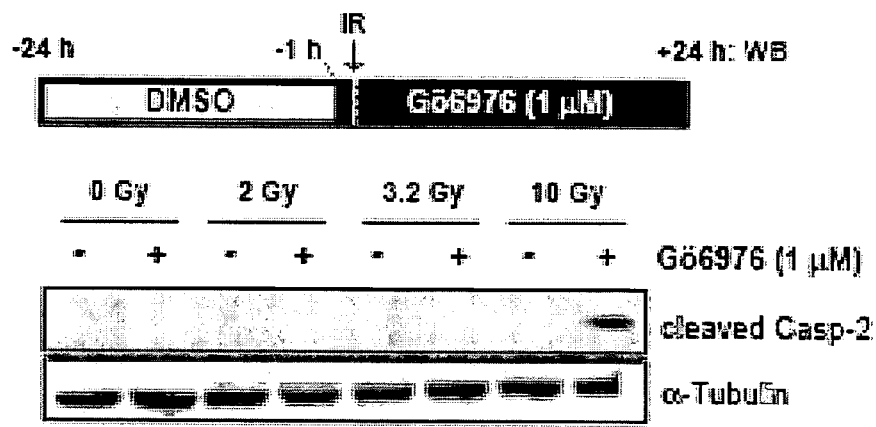

When Gö6976 (1 µM) was applied 1 hour before IR (hbIR), strong caspase-2 cleavage was observed after 10 Gy treatment, as expected, but no detectable cleavage was seen after 2 or 3.2 Gy IR (FIG. 7D). However, when the cells were exposed to Gö6976 for an additional 5 hbIR, 3.2 Gy synergized with the inhibitor to activate caspase-2 as efficiently as the standard 10 Gy protocol (FIG. 7E). When cells were exposed to 500 nM of Gö6976 for 24 hbIR, synergistic activation of caspase-2 was observed with as low as 2 Gy (FIG. 7F). However, the levels of cleaved caspase-2 were relatively weak (they resembled that obtained after 10 Gy IR alone), correlating with an inability of Gö6976 to significantly radiosensitize the cells, as shown in a clonogenic assay (FIG. 7G, compare bars 3 and 4). In contrast, the 3.2 Gy exposure induced a more robust caspase-2 activation, which translated in an average 50% reduction in number of colonies (compare bars 5 and 6). Remarkably, this phenotype was completely rescued by CASP2 knockdown (compare bars 6 and 14), demonstrating that the Chk1-suppressed pathway was responsible for the long-term radio sensitizing effect. Given that such single 3.2 Gy pulses are typically delivered ~15 times over the course of treatment, the Gö6976-induced 50% cell-killing effect obtained after a single IR exposure strongly supports the use of Chk1 inhibitors in hypofractionated radiotherapy.

Gö6976 Selectively Radiosensitizes Zebrafish In Vivo Models of p53 Loss and bcl-2 Gain Chk1 inhibitors hold considerable promise in cancer therapy, as they are expected to synergize with genotoxic agents to kill tumor cells lacking functional p53, without affecting normal cells (Kawabe, 2004; Zhou and Bartek, 2004). Although these assumptions rest almost entirely on in vitro cell culture data (Garber, 2005), UCN-01 has already entered clinical trials. Despite promising antitumor effects, UCN-01 has generated major concerns over its toxic effects in patients, which were attributed to its lack of specificity (Kawabe, 2004; Zhou and Bartek, 2004). Gö6976 has not been tested in vivo in a vertebrate model system. We therefore evaluated it as well as specific Chk2 and ATM inhibitors in the zebrafish system. Drug toxicity was monitored by scoring the AO reactivity of inhibitor-treated, but non-irradiated, p53$^{+/+}$ embryos (left column in FIG. 8A). Unless otherwise indicated, the inhibitors were applied at 18 hpf (that is, immediately before IR) for a total of 6 hours.

Figure 8A:
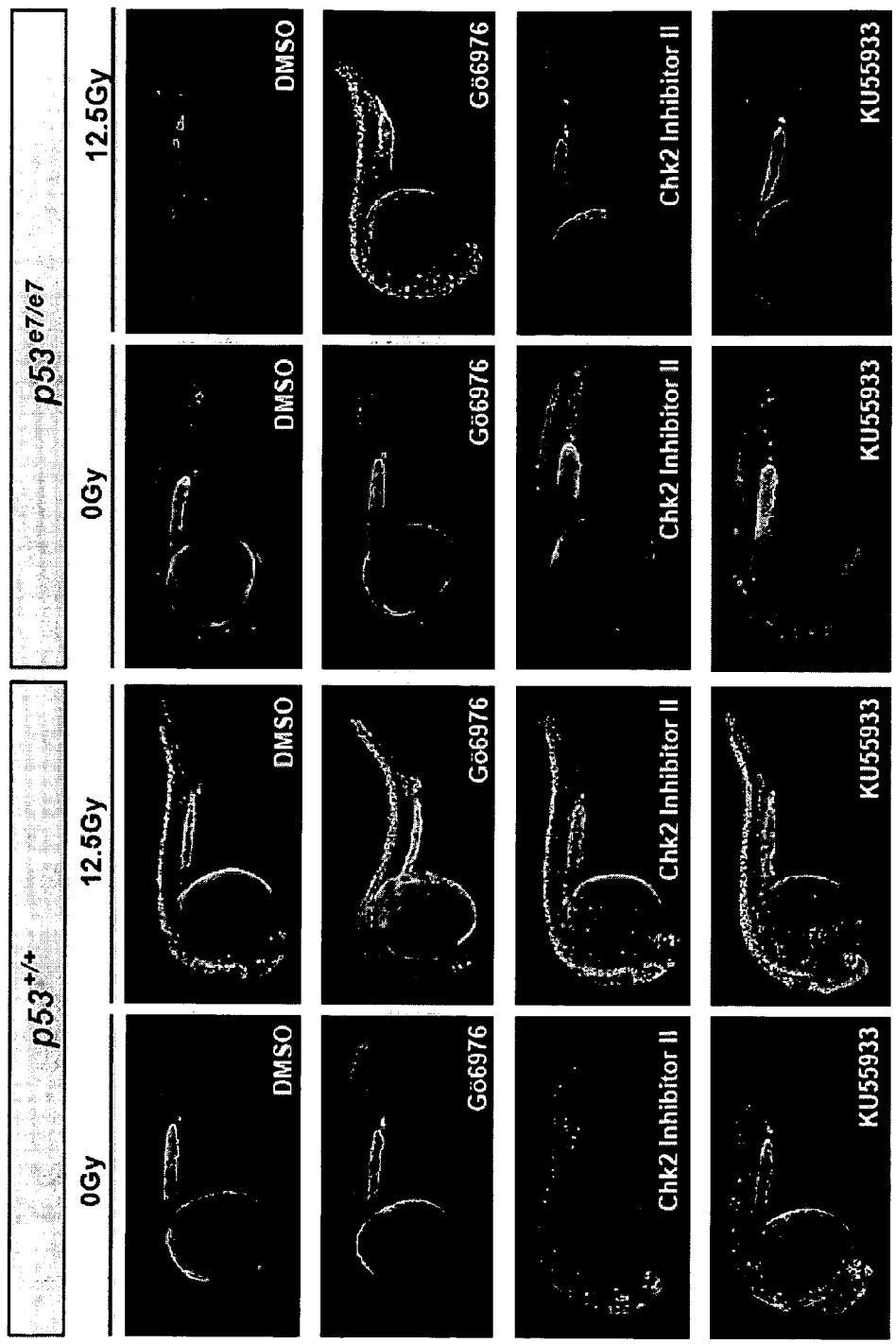
FIG. 8 provides a series of zebrafish images, a diagram of temporal representation, and a schematic of a working model, together showing effects of Gö6976 in zebrafish in vivo models of p53 loss and bcl-2 gain. (A) Fluorescence images of AO-labeled embryos of indicated genotypes photographed at 25.5 hpf. Embryos were exposed to 0 or 12.5 Gy IR and to the indicated drugs at 18 hpf. Gö6976, specific Chk1 inhibitor (1 μM). Chk2 Inhibitor II, specific Chk2 inhibitor (10 μM). KU55933, specific ATM inhibitor (10 μM). Note the range of toxicities in nonirradiated $p53^{+/+}$ embryos treated with KU55933 or Chk2 Inhibitor II, with strong AO labeling preferentially localized in the brain and eyes (first column, $3^{rd}$ and $4^{th}$ rows), as opposed to the Gö6976-treated embryo (first column, $2^{nd}$ row). Reciprocally, note the strong IR-induced AO labeling in the Gö6976-treated p53 mutant (last column, $2^{nd}$ row), but the lack of staining in the mutants treated with KU55933 or Chk2 Inhibitor II (last column, $3^{rd}$ and $4^{th}$ rows). (B) Temporal requirement for Chk1 loss with respect to IR. p53 mutant embryos were exposed to Gö6976 for the indicated times. AO staining was quantified on a scale from − to +++ with − representing the p53 mutant response and +++ the response of sibling mutants treated with Gö6976 for 6 hours (~500-fold greater response). (C) Fluorescence images of 9-dpf zebrafish larvae carrying the indicated transgene. Larvae were treated with 0 Gy or 15 Gy IR at 5 dpf, and exposed to Gö6976 (or DMSO as control) for a total of 5 days starting at 4 dpf. White arrowhead indicates the position of the thymus. Note the absence of detectable GFP in the Gö6976-treated rag2::GFP-bcl-2 irradiated larva. (D) Simplified model for the vertebrate apoptotic response to DNA damage, highlighting the p53-independent pathway normally blocked by IR-activated Chk1 ('CS', for Chk1-suppressed pathway), which is distinct from the classical intrinsic (mitochondrial, 'MIT') and extrinsic (death-receptor, 'DR') pathways. The inhibitory arrow (⊥) on upper right represents the ability of Chk1 to prevent the accumulation of DNA damage following IR (for review see, Zhou and Bartek, 2004). Dashed arrow pointing to Chk2 indicates the likely activation of the Chk2p63/p73 pathway in zebrafish p53 mutants and p53 missense mutant human cell lines. 'X?' suggests the likely involvement of additional factors working in concert or in parallel with caspase-2 to facilitate CDI-DDR signaling downstream of IR and Chk1 inhibition.
Figure 8B:
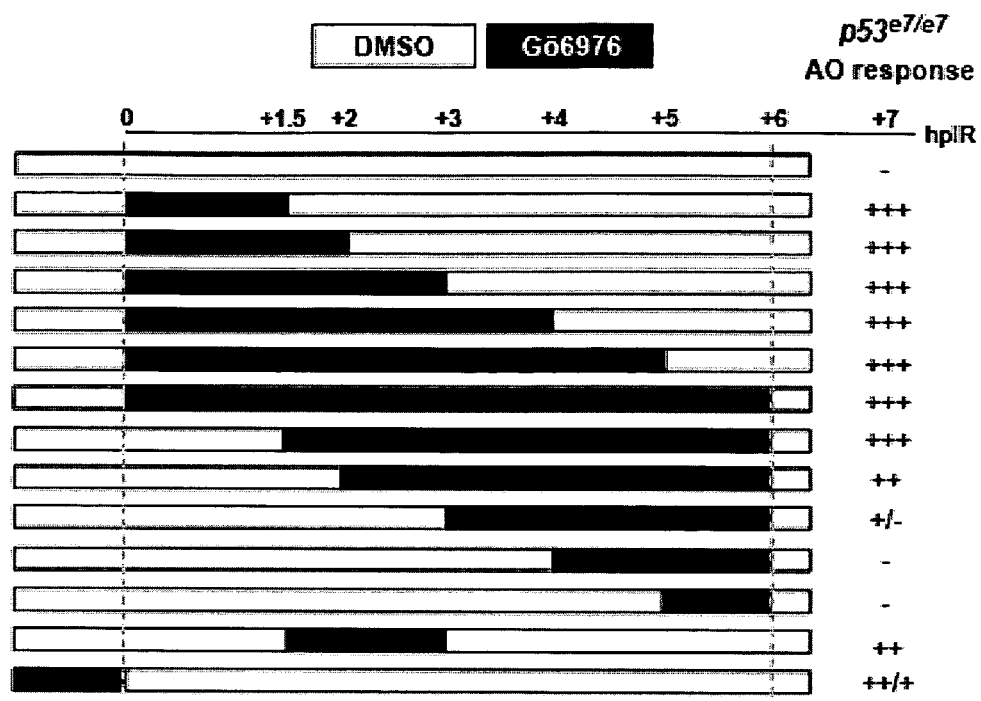

Whereas relatively toxic doses of KU55933 (an ATM inhibitor) (Hickson et al., 2004) and Chk2 Inhibitor II (Arienti et al., 2005) only modestly radiosensitized p53 mutants, a non-toxic dose of Gö6976 (e.g., 1 µM) given to otherwise genetically identical p53 mutant embryos restored a complete response to IR (FIG. 8A). The effects of Gö6976 were almost fully penetrant, with 95% of Gö6976-treated p53 mutants (n=210) showing a marked IR-response recovery. In fact, as short as a 1.5-hour exposure to Gö6976 performed immediately after IR was sufficient to phenocopy the 0-24 hpf chk1 depletion obtained via MO knockdown (FIG. 8B). Similar to chk1 morphants, non-irradiated p53$^{+/+}$ embryos treated with Gö6976 developed into normal adults without overt signs of spontaneous tumorigenesis or other pathologies. These observations provide first in vivo support to recent predictions that specific Chk1 inhibitors could have an elevated therapeutic index (Garber, 2005; Kawabe, 2004).

Figure 8C:
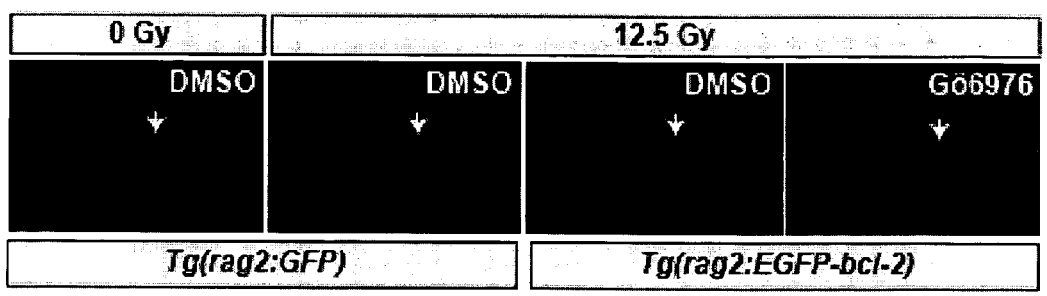
Figure 8D:
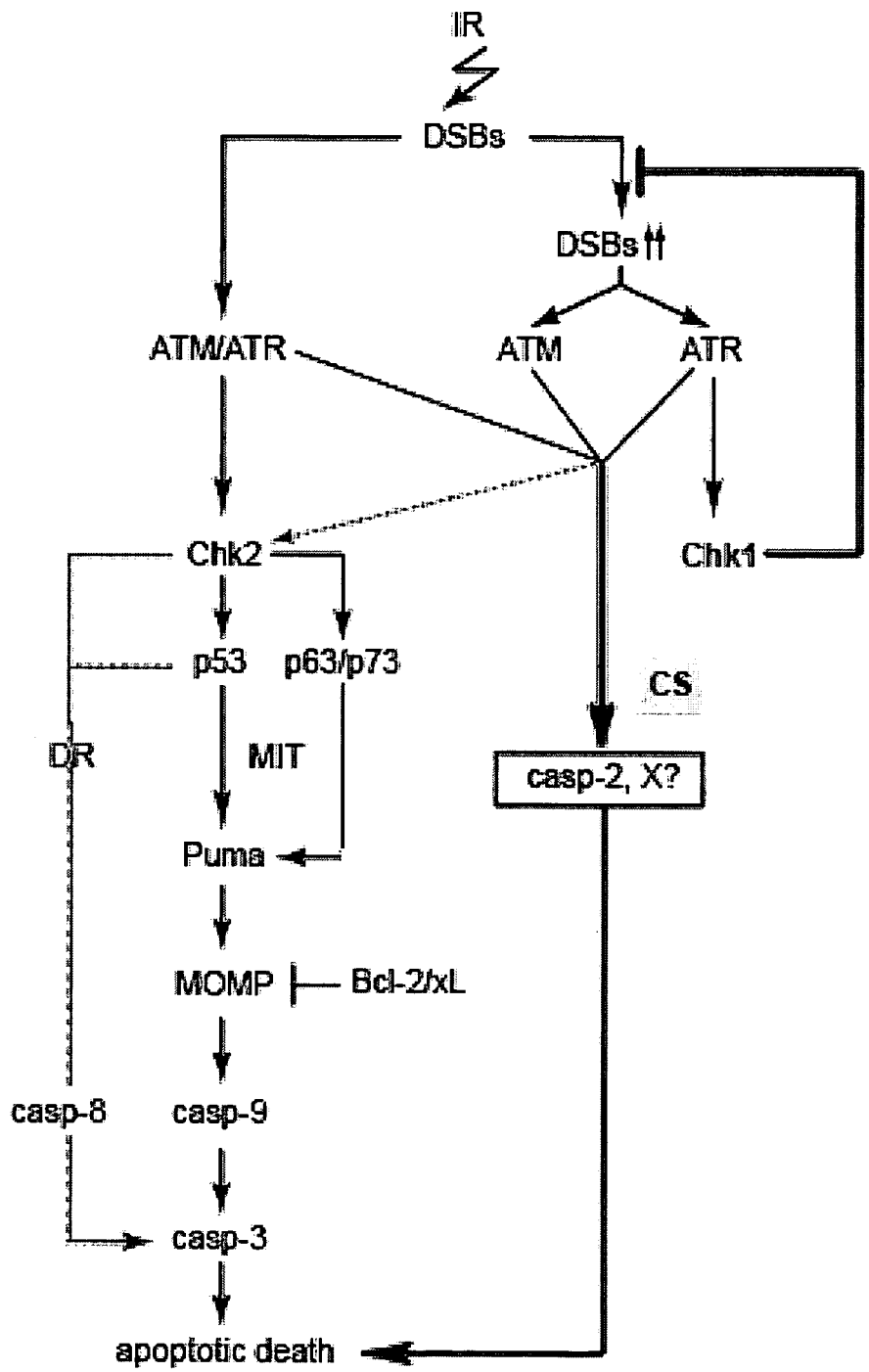

The BCL-2/XL-independence of the Chk1-suppressed pathway (FIGS. 5D & 6B) suggests that Chk1 inhibitors could prove valuable in radio/chemo-sensitizing malignancies overexpressing BCL2 family members, including follicular lymphoma. To test this notion in vivo, we exploited a zebrafish transgenic line expressing a stable EGFP-bcl-2 fusion transgene under control of the rag2 promoter (Langenau et al., 2005). Such Tg(rag2: EGFP-bcl-2) larvae are characterized by highly radioresistant T- and B-cells at 9 dpf. Systemic treatment with Gö6976 suppressed T-cell radioresistance in a mean 58% of these bcl-2-overexpressing larvae (n=26) compared to none of the DMSO-treated larvae (n=28), without any apparent adverse effects (FIG. 8C). Together with our human cell culture studies, our in vivo analysis of Gö6976 in zebrafish raises the remarkable possibility that tumors disrupting p53 or its attendant downstream pathway—in other words, most human cancers—will respond favorably to Chk1 inhibitors.

Discussion

We have identified an evolutionarily conserved apoptotic process distinct from the classical mitochondrial and death receptor axes. This ATM/ATR-caspase-2 pathway is triggered by DNA damage provided that Chk1 activity is simultaneously compromised. The pathway is insensitive to p53 loss and BCL-2/-XL gain, two of the most common genetic alterations in human cancer, and is readily targetable and assessable. Our studies at the interface of living, tumor suppressor-deficient zebrafish embryos and cultured human cancer cells establish a powerful alternative approach to identifying new physiologic pathways relevant to cancer therapy.

An Apoptotic Response to DNA Damage Distinct from Mitochondrial and Death-Receptor Pathways In vertebrates, DNA damage-induced apoptosis classically proceeds through the ATM/ATR-Chk2p53Puma conduit towards Bcl-2/xL inhibition, mitochondrial membrane permeabilization (MOMP), Cyt-c release, and caspase-3 activation (FIG. 8D). Recent in vitro studies have begun to delineate p53-independent apoptotic response pathways, such as the Chk2p73 axis, the majority of which appear to restore MOMP in parallel or downstream of defective p53 (Gong et al., 1999; Kolesnick and Fuks, 2003; Li et al., 2000; Lin et al., 2004; Urist et al., 2004; Yuan et al., 1999). p53-independent response systems might also recruit the death-receptor axis, providing a MOMP-independent means to restore caspase-3 activity after DNA damage (FIG. 7D) (Afshar et al., 2006; Huang et al., 2006; Kasibhatla et al., 1998; Yount et al., 2001).

Surprisingly, the evolutionarily conserved p53-independent axis we have identified in vivo is insensitive to genetic ablation of the mitochondrial or death-receptor pathways, via depletion of Puma, caspase-9, caspase-8, or FADD. As seen in zebrafish embryos and human tumor cells, the pathway is also completely insensitive to BCL-2/XL gain and proceeds independently of caspase-3 (the convergence point of the mitochondrial and death-receptor pathways). Thus, while our genetic analyses indicate that the new pathway initiates through the canonical ATM/ATR DDR channel, it then clearly diverges from classical apoptotic pathways (FIG. 8D). Our Chk2 knockdown analyses in zebrafish and human cells show that the new pathway bifurcates upstream of the Chk2 node, and proceeds directly towards caspase-2 activation.

Caspase-2 is activated following IR+Chk1 inhibition in five p53-deficient human cancer cell lines, and is required for radiosensitization in p53$^{e7/e7}$;chk$^{MO}$ embryos and Chk1-inhibited HeLa cells. caspase-2 therefore is an essential cell-death executioner in the Chk1-suppressed pathway. Precisely how caspase-2 executes cell death cannot be deduced from previous studies of caspase-2-mediated apoptosis following DNA damage or other forms of stress. Indeed, such studies placed caspase-2 either upstream of MOMP (Bergeron et al., 1998; Bonzon et al., 2006; Castedo et al., 2004b; Lassus et al., 2002; Nutt et al., 2005; Tinel and Tschopp, 2004; Tu et al., 2006), or upstream of caspase-8 within the extrinsic pathway (Shin et al., 2005; Wagner et al., 2004). Given that caspase-2 is the most highly conserved caspase throughout metazoans (Troy and Shelanski, 2003), it is surprising that only a handful of caspase-2 substrates have been identified to date (reviewed in, for example, Zhivotovsky and Orrenius, 2005). Hence, while our experiments assign a new, MOMP- and caspase-8-independent role to caspase-2, elucidating the events downstream of this protease awaits better knowledge of its biochemistry. In particular, it will be important to determine whether caspase-2 acts as an initiator or executioner caspase, or whether it could accomplish both functions (Troy and Shelanski, 2003; Zhivotovsky and Orrenius, 2005).

A unifying feature of the ATM/ATR-caspase-2 pathway in zebrafish and human cancer cells is that it is triggered by IR and Chk1 inhibition combined, but not by either stimulus alone. The underlying mechanism may relate to our observation that ATM and ATR—while both necessary—are individually insufficient to activate the pathway (FIG. 5A). We propose two models for this non-redundancy. In the first (quantitative) model, a threshold of ATM+ATR signaling exists below which caspase-2 fails to become activated. At lower levels of damage (such as seen after IR or Gö6976 alone), insufficient amounts of ATM/ATR activity are induced and caspase-2 fails to activate, whereas at higher levels (as seen in the combination treatment), the total level of ATM/ATR activity matches the threshold for caspase-2 activation, resulting in apoptosis. In the second (qualitative) model, ATM and ATR serve different functions in the sensory transduction of DNA damage, with ATM responding primarily to IR-induced double stranded breaks and ATR predominantly sensing damage resulting from lack of Chk1 activity, such as replication stress (Cuadrado et al., 2006; Syljuasen et al., 2005).

Figure 20:
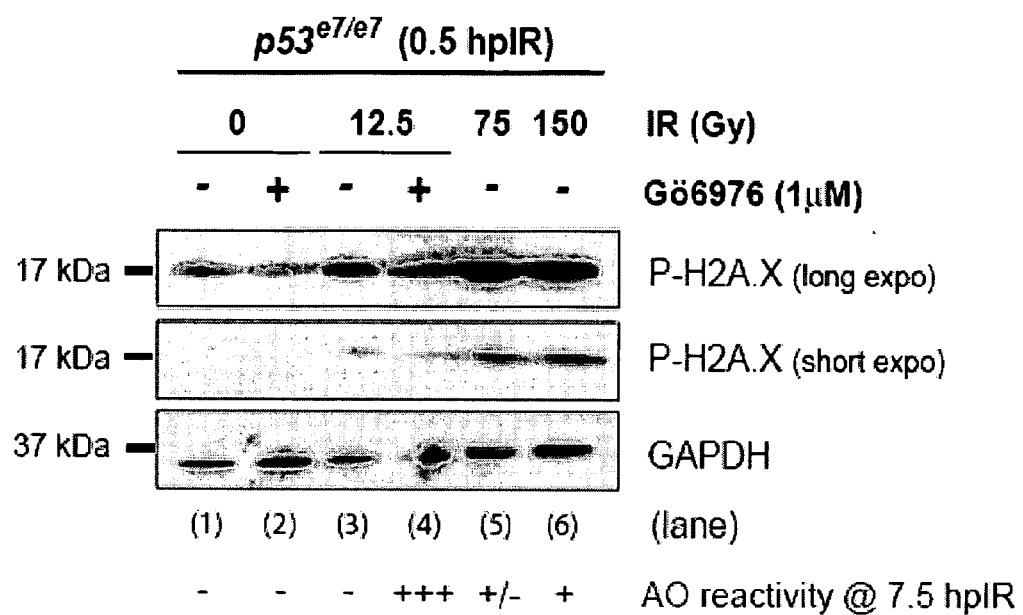
FIG. 20 provides a set of western blot images and a set of fluorescence images, showing that extreme IR-induced DNA damage fails to force apoptosis in zebrafish p53 mutants endowed with wild-type Chk1 activity. (A) Western blot comparing the levels of phosphorylated H2A.X in protein lysates from p53 mutant embryos 0.5 hr after 0, 12.5, 75 or 150 Gy IR in the presence or absence of the specific Chk1 inhibitor Gö6976 (1 μM). Acridine orange (AO) reactivity at 7.5 hpIR of embryos from the same experiment is indicated below the blot (See FIG. 20B for images of representative embryos). Note that AO reactivity does not correlate with levels of DNA damage. Specifically, IR doses up to 150 Gy (which lead to dramatic levels of DNA damage) are insufficient to mimic the combinatory effects of 12.5 Gy+Chk1 inhibitor treatment. (B) Fluorescence images of AO-stained embryos from the experiment described in FIG. 20A. Corresponding western blot lanes are indicated in upper left corners.
Figure 20B:
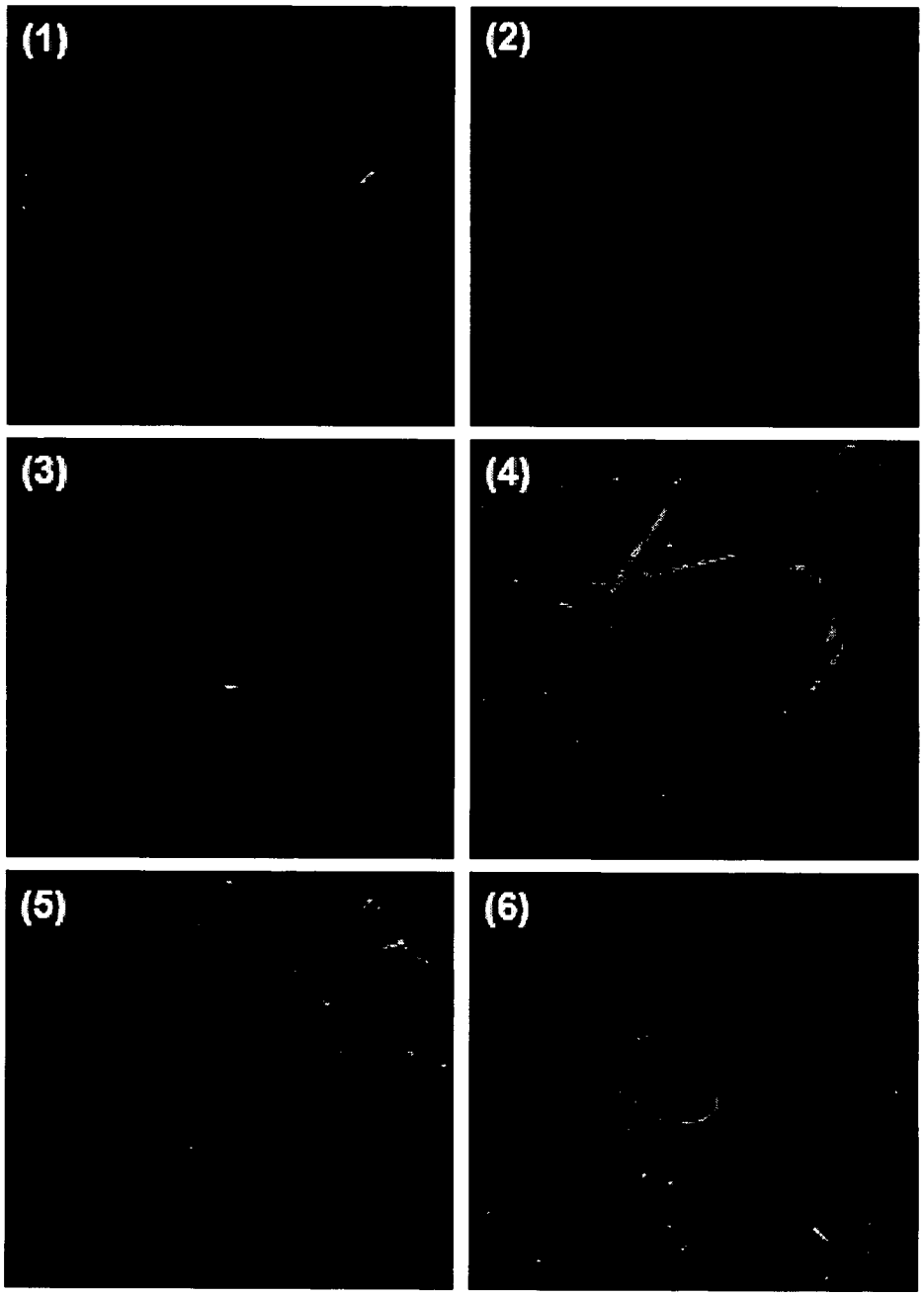
Figure 21:
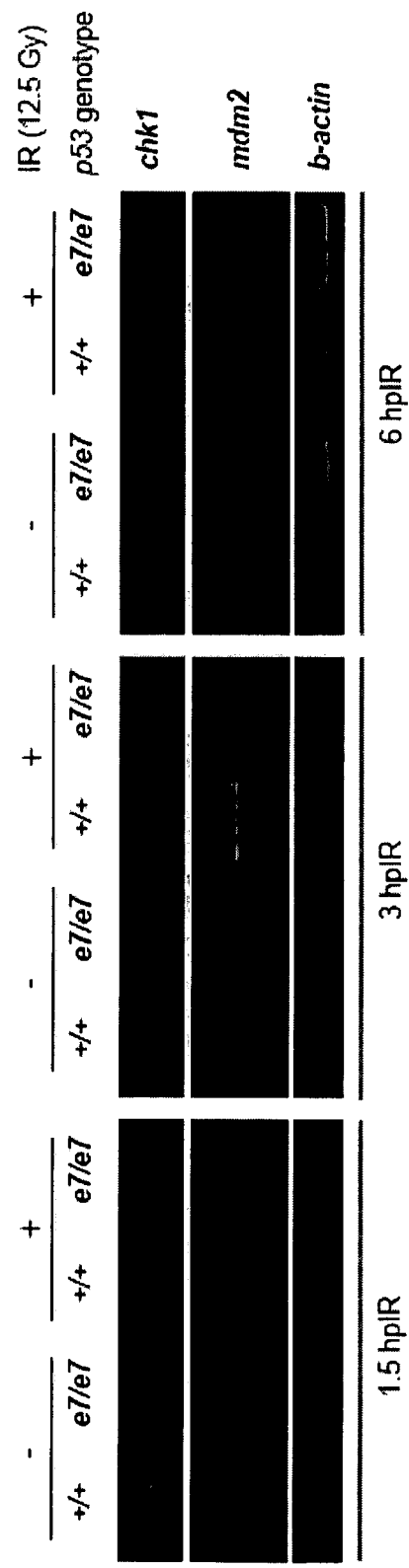
FIG. 21 provides a set of DNA gel images, showing that chk1 expression levels are insensitive to IR and to the p53$^{e7}$ mutation. Semi-quantitative RT-PCR analysis of zebrafish chk1 at the indicated time points after IR (0 or 12.5 Gy) in the p53 wild-type or mutant background. Expression of the p53 target gene mdm2 is shown as an internal positive control, and β-actin levels are shown as loading control.

The first model predicts that increasing IR doses should eventually substitute for Chk1 inhibitor treatment by matching the DNA damage threshold necessary for caspase-2 activation. In other words, the ATM/ATR-caspase-2 pathway would encode a non-discriminatory defense mechanism against high levels of DNA damage. However, an in vivo test of this hypothesis yields unsupportive data (FIG. 20). We thus favor the second model, according to which the ATM/ATR-caspase-2 apoptotic program is obligatorily tied to Chk1 activity. Precisely which of Chk1's multiple cellular functions links the kinase to the pathway remains to be explored, however, a direct involvement of the intra-S or G2/M checkpoints is challenged by the fact that apoptosis does not occur preferentially during DNA replication or mitosis (FIGS. 4D & 6I).

Given the present evidence, we propose that the ATM/ATR-caspase-2 pathway is a tumor suppressive mechanism that ensures the demise of cells carrying potentially harmful DNA lesions in the absence of proper genome-surveillance activity (such as mediated by Chk1; Lam et al., 2004). This function would also likely account for the evolutionary conservation of the pathway. Our observation that the pathway can operate both in the absence and presence of wild-type p53, as revealed in irradiated p53$^{+/+}$;chk1$^{MO}$;bcl-xl embryos and in irradiated p53$^{+/+}$;Tg(rag2:EGFP-bcl-2) larvae treated with Gö6976, disqualifies the pathway as representing a 'backup' program (Roos and Kaina, 2006) operating only in cells that lack p53. Rather, we propose that it constitutes an alternative, perhaps primitive response to DNA injury that evolved independently of the p53 network. Intriguingly, however, TP53$^{+/+}$ and TP53$^{-/-}$ HCT116 cells differed in their response to IR+Go6976 treatment, in that caspase-2 but not caspase-3 cleavage was actively inhibited in the TP53$^{+/+}$ cells, via an apparent downregulation of procaspase-2 levels (FIG. 7A). Thus, a form of cross-talk might have evolved to link these p53-dependent and -independent apoptotic pathways, similar to that described for caspase-dependent and -independent pathways (Colell et al., 2007).

Therapeutic Implications

Based on their in vitro ability to selectively sensitize p53-deficient human tumor cells to IR and a variety of antineoplastic agents, Chk1 inhibitors have entered phase I-II clinical trials for anticancer activity in humans (Kawabe, 2004; Zhou and Bartek, 2004). Because of the lethality of Chk1$^{-/-}$ mice, however, it has remained unclear whether the potency and selectivity of radio/chemo-sensitization observed in vitro will apply equally well to in vivo situations (Garber, 2005; Liu et al., 2000). Our findings in zebrafish using the Chk1 inhibitor Gö6976 and zebrafish chk1 morphants, which retain weak residual levels of Chk1 activity, reveal that otherwise subtoxic levels of Chk1 inhibition are in fact sufficient to strongly and selectively sensitize p. 53 mutant cells to IR-induced apoptosis within the context of a living vertebrate (FIGS. 1-3 & 8). Still, mammalian cells could be more sensitive to partial and transient Chk1 inhibition than are zebrafish cells, especially in regenerative tissues (Lam et al., 2004). Thus, inhibitor dosage and duration of treatment are likely to represent important variables in Chk1-targeting therapies (Garber, 2005). We would emphasize in this regard that acute treatments of zebrafish embryos with Gö6976 (i.e., as short as 1.5 hours) immediately after IR were sufficient to achieve maximal p53 mutant cell killing in vivo (FIG. 7B).

Clinical trials of UCN-01 (the most widely used Chk1 inhibitor) have revealed multiple side effects in patients treated with doses displaying some anticancer activity, although such toxicity may arise from promiscuous inhibition of kinases other than Chk1 (Kawabe, 2004; Zhou and Bartek, 2004). Our results in zebrafish and human cancer cell lines support the view that more specific Chk1 inhibitors, such as Gö6976 or related compounds, administered for limited periods of time, will yield a favorable therapeutic index (Garber, 2005; Kawabe, 2004).

Finally, our study illustrates the benefits of mechanistic knowledge of drug action, both in terms of better defining the spectrum of tumors that can be targeted and improving the drug's evaluability in the clinic. For instance, our results unexpectedly predict that besides tumors with altered p53 activity, those with other types of prosurvival alterations affecting MOMP downstream of p53, such as BCL2-expressing follicular lymphomas, will respond favorably to Chk1 inhibitors. In addition, our results identify caspase-2 (pro- versus cleaved forms) as a candidate biomarker for Chk1-targeting treatments. The identification of such specific biomarkers remains a pressing challenge in targeted cancer therapeutics (Tse et al., 2007).

Experimental Procedures

Zebrafish Stocks

The homozygous viable p53$^{M214K}$ and p53$^{N168K}$ mutant lines (p53$^{e7}$ and p53$^{e6}$, respectively, in this article) (Berghmans et al., 2005), and the Tg(rag2:GFP) (Langenau et al., 2003), Tg(rag2:EGFP-bcl-2) (Langenau et al., 2005), Tg(pu.1:GFP) (Hsu et al., 2004) and Tg(myoD:EGFP) (Yang et al., 2004) transgenic lines were used and maintained at 28.5° C. by standard methods (Westerfield et al., 1997). For experimental purposes (FIG. 2E), irradiated p53$^{e6/e6}$ mutants were incubated for 6 hr at 37° C. (the restrictive temperature for the N168K mutation; Berghmans et al., 2005). The apparent myeloid hyperplasia seen in p53$^{e7/e7}$ embryos compared with p53$^{+/+}$ embryos (FIG. 2G, bars 1 and 5) does not segregate with the M214K mutation, and thus likely represents a background effect. However, myeloid radioresistance segregated with p53 deficiency throughout multiple generations and in all genetic backgrounds tested (AB, TU and WIK).

Morpholino Screen and Epistasis Analyses Using the Live AO Assay

Morpholino oligonucleotides (MOs) were obtained from Gene Tools™ LLC. MO sequences, target sites, working concentrations, knockdown efficiencies, selected references and injection procedure, as well as detailed protocols for AO staining of live embryos and the ImageJ-based quantification method are listed in Table 1, FIGS. 11 & 16 and Experimental Procedures described in more detail below.

Human Cancer Cell Lines

The HeLa, SAOS2, MDA-MB-435 and LN-428 cell lines, the TP53$^{+/+}$ and TP53$^{-/-}$ HCT116 isogenic pair (Bunz et al., 1998), and the Cyt-c-GFP transgenic, 2H18 HeLa-derived lines (Goldstein et al., 2000) carrying or not carrying a BCL2 transgene were cultured in DMEM medium (Gibco) supplemented with 15% fetal bovine serum (FBS).

si- and shRNAs siRNAs directed against LACZ (5'-AACGTACGCG-GAATACTTCGA-3') (SEQ ID NO: 1), CHK1 (5'-AA-GAAGCAGTCGCAGTGAAGA-3') (Wang et al., 2007) (SEQ ID NO: 2) and CHK2 (Santa Cruz, sc-29271) were transfected in HeLa cells using Hiperfect (QIAGEN) according to the manufacturer's instructions. Cells were exposed to IR+/−Gö6976 at 72 hr post-transfection. shRNA knockdown analyses were performed as previously described (Moffat et al., 2006). Briefly, double-stranded DNAs including the 21mer shRNA sequence were cloned into the lentivirus vector pLKO1-puro. After cotransfection into the 293 packaging cell line with packaging plasmid delta 8.9 and envelope plasmid VSV-G, supernatants containing the lentivirus were collected and used to infect HeLa cells for 2 hr. Cells were allowed to recover for 48 hr prior to any treatment. Knockdown levels in each line were verified by immunoblot after incubation with 0.7 μg/mL of puromycin for 72 hr.

```
                                                (SEQ ID NO: 3)
shRNAs were:
GATATGTTGCTCACCACCCTT (CASP2 shRNA1);

(SEQ ID NO: 4)
GGAGATGTCTGAATACTGCAG (CASP2 shRNA2);

(SEQ ID NO: 5)
ACACACTTCCAGCTGGCATAT (CASP2 shRNA3);

(SEQ ID NO: 6)
CCGAAAGGTGGCAACAGAATT (CASP3 shRNA);

(SEQ ID NO: 7)
GCAAGCTGACCCTGAAGTTCA (GFP shRNA);

(SEQ ID NO: 8)
GTGACAGCTGTCAGGAGTATT (CHK1 shRNA1);

(SEQ ID NO: 9)
GCAACAGTATTTCGGTATAAT (CHK1 shRAN2);
and
                                               (SEQ ID NO: 10)
CTAAGCACATTCAATCCAATT (CHK1 shRNA3).
```

TABLE 1

Morpholino Oligonucleotides.

| gene | acc. # or ensembl ID or zfin ID | MO target | reference | sequence | wk. conc. |
|---|---|---|---|---|---|
| chk1 | ENSDARG00000014385 (zgc: 56093) | atg/5'UTR | this work | aggcacagccattatgcaatcttcg (SEQ ID NO: 11) | 0.25-0.75 |
|  |  | 5 bpmm | this work | agCcaGagcGattatCcaatGttcg (SEQ ID NO: 12) | 0.25 mM |
| chk2 | AF265346 (ENSDARG00000025820) | atg/5'UTR | this work | tccagcttcctcagacatgatgctt (SEQ ID NO: 13) | 0.25 mM |
| atm | AB191208 (Imamura and Kishi, 2005) | ag i55/e56 | Imamura and Kishi, 2005 | gaaaacggcaccacctggtaaaaac (SEQ ID NO: 14) | 0.20 mM |
| atr | ENSDARG00000012750 | atg/5'UTR | Stern et al., 2005 | tgacatttctagtccttgctccatc (SEQ ID NO: 15) | 0.20 mM |
| smg-1/atx | UNSDARG00000011625 | gt e6/i6 | this work | gagtaaatccattggagtaggtacc (SEQ ID NO: 16) | 0.25 mM |
| plk2 | ENSDARG00000019130 | gt e4/i4 | this work | tgcatacataccgagtttcaagtca (SEQ ID NO: 17) | 0.20 mM |
| plk3 | ENSDARG00000007520 (cnk) | gt e4/i4 | this work | ggaatcaaaaacgctacctagtttg (SEQ ID NO: 18) | 0.15 mM |
| aurkb | ENSDARG00000037640 (stka) | gt e8/i8 | this work | cgtgattatcagactgaccttagtg (SEQ ID NO: 19) | 0.15 mM |
| smc1 | ENSDARG00000058203 (smc1a) | atg/5'UTR | this work | ctttaagtagcccatgctgaaccac (SEQ ID NO: 20) | 0.15 mM |
| p21$^{waf1/cip1}$ | CN501420 | gt e2/i2 | this work | taataaagaggtctgacctgtgatg (SEQ ID NO: 21) | 0.10 mM |
| casp2 | DQ812119 (Eimon et al., 2006) | gt e4/i4 | this work | cgctgaaaccctgttgtacctgtgg (SEQ ID NO: 22) | 0.25 mM |
|  |  | gt e3/i3 | this work | accatactaaagtaccaaccatgag (SEQ ID NO: 23) | 0.75 mM |
|  |  | 5 bpmm | this work | cgGtgaaaGcctCttCtacctCtgg (SEQ ID NO: 24) | 0.25 mM |
| casp8 | BC081583 (Eimon et al., 2006) | gt e5/i5 | this work | acagggttttaactcacagtagatc (SEQ ID NO: 25) | 0.25 mM |
| casp9 | BC097103 (Eimon et al., 2006) | gt e3/i3 | this work | gatggaaaaacacacttacggactg (SEQ ID NO: 26) | 0.15 mM |
| puma | DQ860151 (Kratz et al., 2006) | gt e2/i2 | this work | aaccaagcatgactcttaccctctg (SEQ ID NO: 27) | 0.25 mM |
| p63 | ENSDARG00000044453 (tp731) | gt e3/i3 | this work | aaagagtggcataccgtcattgaac (SEQ ID NO: 28) | 0.25 mM |
| TAp73 | tp73 | atg/5'UTR | Rentzsch et al., 2003 | ggatgttggacaatccaccgcaggg (SEQ ID NO: 29) | 0.25 mM |
| zFADD | BC114285 (Eimon et al., 2006) | gt e3/i3 | Eimon et al., 2006 | taacgttaccaacctcgctctttcg (SEQ ID NO: 30) | 0.25 mM |
| p53 | tp53 | atg/5'UTR | Langheinrich et al., 2002 | gcgccattgctttgcaagaattg (SEQ ID NO: 31) | 0.20 mM |

ENSDARG entries (ENSEMBL DANIO RERIO GENE) refer to the Ensembl annotations of the indicated zebrafish genes, which are available at the Sanger zebrafish genome project website, http://www.ensembl.org/Danio_rerio/index.html. Zfin IDs are indicated in parentheses. In the 'MO target' column, splice sites targeted by individual MOs are indicated as follows. 'gt', splice donor site; 'ag', splice acceptor site; $e_y/i_y$, exon/intron boundary number y; $i_y/e_y$, intron/exon boundary number y. As an example, 'gt e4/i4' indicates that the MO targets the splice donor site of intron 4. 5 bpmmMO, 5 base-pair mismatch MO (mismatches indicated in uppercase in the 'sequence' column).

Morpholino and mRNA Injections

Morpholino oligonucleotides (MOs) synthesized by Gene Tools™ LLC, were resuspended in sterile water at a concentration of 1 mM and delivered into zebrafish embryos at the one-cell stage by microinjection. The injection apparatus consisted of a heat-pulled, filamentous RNAse free capillary tube positioned by a micromanipulator (Narishige™ M-125), through which the MO was pressure-injected using a nitrogen air supply controlled by a microinjector (Harvard Apparatus™ PLI-100). MOs were delivered into the yolk of embryos at the one cell stage, just below the cytoplasm. For each previously unpublished MO, the working concentration was determined as the highest dose compatible with normal zebrafish development in the p53$^{e7/e7}$ background (maximal subtoxic concentration). In particular, we used concentrations that did not cause necrosis in the brain, a non-specific toxic effect typically associated with high MO doses. 100 ng of bcl-xl mRNA in vitro transcribed from full-length zebrafish bcl-xl cDNA cloned into pCS2 were injected as described above. All embryos were grown at 28.5° C. in egg water (5 mM NaCl, 0.17 mM KCl, 0.4 mM CaCl$_2$ and 0.16 mM MgSO$_4$). MO sequences, target sites, working concentrations, and selected references are listed in Table 1 above. Knockdown efficiencies for the chk1, chk2, atm, atr, p63, casp8 and casp9 MOs at their maximal subtoxic concentrations are shown in FIG. 10. The sequences of the PCR primers used for RT-PCR-based monitoring of MO efficiencies are available upon request.

Detection and Quantification of Cell Death by Acridine Orange Labeling

Live zebrafish embryos were dechorionated in pronase (2.0 mg/mL in egg water) for 3 to 5 min and rinsed five times in egg water at 18 hpf. Embryos were then γ-irradiated (12.5 Gy) using a $^{137}$Cs-irradiator (Gammacell 1000) at 18 hr post-fertilization (hpf). At 24 hpf, embryos were incubated in 10 mg/mL Acridine Orange (AO; Sigma A-6014) in egg water for 30 min at 28.5° C., followed by 3 quick rinses and three 10-min washes in egg water. 5-10 AO-treated embryos were anesthetized in Tricaine (200 mg/mL; 3-amino benzoic acid ethylester from Sigma, A-5040) and mounted laterally on a glass slide in warm 0.5% agarose in egg water by streaking a thin layer of the warm agarose across the surface of the slide, and gently pulling the embryos across the agar with a transfer pipette. Lateral images of each zebrafish were acquired on a Zeiss Axioplan2 fluorescence microscope (5× lens), using OpenLab software and a Hammamatsu C4742-95 digital camera. All images were then converted to 8-bit grayscale in NIH ImageJ using the Image>Type>8-bit command. Next, we cropped the images using the Polyonal Selection tool and the Image>Crop functions to include only the trunk of the animal from the head until the beginning of the yolk tube (MO screen; FIG. 1B) or along the entire spinal cord (epistasis analyses; FIGS. 6A & 6D). The area outside of the selected region of interest was cleared using the Edit>Clear Outside command to create a distinct boundary around the area of interest (this is important as it allows the area of interest to be precisely selected after applying the threshold). Next, we split the acquired images into features of interest and background using the Image>Adjust>Threshold function in NIH ImageJ. We then set the maximum threshold of each image to 255 (the lower slide bar in the Threshold window), and adjusted the minimum threshold to the optimized threshold (see below). The threshold was applied using the Black & White display option, with the following Lut options applied; Thresholded pixels to foreground color; Remaining pixels to background color and Black foreground, white background. This manipulation causes pixels with brightness values greater than or equal to the lower threshold and less than or equal to the upper threshold to be displayed in black. Next, we re-selected the region of interest on the thresholded image, following the bounded image carefully, and analyzed the pixels of the image using the Analyze>Analyze Particles function. The Minimum Size was set to 1px, the Maximum Size was set to the maximum value of 999999 and the Masks option was selected under the Show pull-down menu. The following extended options were also selected: Display Results; Clear Results; Summarize, Size Distribution and Record Starts. If selected by default, the Exclude on Edges option was deselected. The Area Fraction for each image selection was taken from the Summary window, which is the percentage of pixels in the selection that were black. To ensure valid comparisons of the AO labeling results across all experiments, we quantitatively determined a baseline Area Fraction across a large set of simultaneously irradiated and processed p53$^{+/+}$ embryos. This was achieved by determining and applying a threshold on all of the p53$^{+/+}$ embryo images which resulted in threshold masks that clearly matched the punctate and distinguishable labeling in the images. This analysis yielded a mean value for the total labeled surface area of ~20% (see FIG. 1B, light gray bar). We included at least 6 p53$^{+/+}$ non-injected control embryos in all subsequent AO-labeling experiments. In each of these new experiments, we first established a threshold such that the mean response of p53$^{+/+}$ embryos (calculated from the new p53$^{+/+}$ images) would match the 20% value. In turn, this particular threshold was applied to all embryos (mutants, morphants) within the experimental set. The same normalization method was used for the epistasis analyses presented in FIG. 6A, but substituting the p53$^{e7/e7}$; chk1$^{MO}$ genotype for the p53$^{+/+}$ genotype. Statistical analysis of data was performed with GraphPad Prism software (GraphPad Software Inc., San Diego, USA).

Whole-Mount In Situ Hybridization in situ hybridization was performed essentially as described previously (Rhodes et al., 2005).

Detection of Apoptotic Cell Death by Whole-Mount TUNEL Labeling

Apoptotic cell death in zebrafish embryos was detected according to a modification of the protocol suggested by the manufacturer (ApopTag® Fluorescein In Situ Apoptosis Detection Kit). Zebrafish embryos were fixed in 4% paraformaldehyde (PFA) overnight at 4° C. and subsequently stored in methanol at −20° C. for at least 2 hr. After rehydration at room temperature in PBST (1×PBS, 0.1% Tween-20), embryos were treated with proteinase K (10 μg/mL) in PBS for 15 min, followed by a 20-min postfix in 4% PFA at room temperature. After 3 quick rinses and two 10-min rinses in PBST, embryos were transferred to poly-propelene test tubes and incubated in 75 μL of equilibration buffer (ApopTag® Fluorescein In Situ Apoptosis Detection Kit) for one hour. Embryos were then incubated in 55 uL of the kit's working strength terminal deoxynucleotidyl transferase (TdT) enzyme overnight at 37° C. To avoid drying out the embryos, test tubes were sealed with parafilm and placed in closed 50 mL conical tubes with 25 mL of water. The end-labeling reaction was stopped by washing the embryos three times 15-min with 2 mL of the kit's stop/wash buffer. Tagged DNA was detected with sheep anti-digoxigenin-fluorescein or sheep anti-digoxigenin-rhodamine conjugated Fab fragments.

Whole-Mount Immunohistochemistry

Zebrafish embryos were fixed in 4% PFA overnight at 4° C. and subsequently dehydrated in methanol at −20° C. for at least 2 hr. Embryos were then rehydrated three times 5 min in PBST (1×PBS, 0.1% Tween-20), and permeabilized by treatment with PDT (PBST+1% DMSO) supplemented with 0.3% Triton-X for 20 min. Embryos were treated with blocking solution (PDT supplemented with 10% heat inactivated FBS and 2% BMB, Boeringer Mannheim Blocking Solution) for 30 min before the addition of primary antibody (anti-pH3, 1:750; anti-activated-Casp-3, 1:200; anti-HUc, 1:1000). Embryos were incubated in primary antibody overnight at 4° C., rinsed three times 20 min in PDT and then reblocked for 30 min in blocking solution before the addition of Alex-aFluor-conjugated secondary antibody (1:250).

Embryos were analyzed and imaged on a Zeiss Axioplan2 fluorescence microscope using 5×, 10× and 20× lenses, running OpenLab software and a Hammamatsu C4742-95 or Jenoptik Progres C-14 camera. For TUNEL/pH3 double labelings, embryos were first processed for the TUNEL reaction and then treated according to the above immunohistochemistry protocol, minus methanol dehydration. Double-labeled embryos were flat-mounted in Vectashield fluorescence mounting media (Vector Laboratories H1000) and imaged with a Zeiss LSM510 Meta NLO laser scanning confocal microscope.

Electron Microscopy

Zebrafish embryos were fixed in 2.5% GA 1% PFA overnight and then washed several times in 0.1M Cacoldylate buffer. Embryos were osmicated in 1% osmium tetroxide/1.5% potassium ferrocyanide (final solution) for 3 hours, followed by several washes of $dH_2O$. 1% uranyl acetate in maleate buffer was added for one hour then washed several times with maleate buffer (pH 5.2). This was followed by a graded cold ethanol series up to 100%, which was changed 3× over one hour. Propylene oxide followed, again 3 changes over one hour. Embryos were then placed in ½ and ½ propylene oxide with plastic mixture including catalyst overnight, embedded in Taab resin the next day, and incubated at 60° C. for one or two days. Blocks were cut with a Leica ultracut microtome to generate 95 nm thick sagittal sections of whole embryos. Sections were picked up on formvar coated Cu slot grids, stained with 0.2% Lead Citrate, and viewed and imaged under the Philips Technai Spirit Electron Microscope.

Blastula-Cell Transplantations

One cell-stage embryos of $p53^{+/+}$ or $p53^{e7/e7}$ genotypes were injected with Texas Methyl Red Dextran as a lineage tracer with or without chk1 MO. At the blastula stage (4 hpf), 50-100 cells populating the spinal-cord-fated region were back-loaded into a pulled glass needle and transplanted into host blastulae of $p53^{+/+}$ or $p53^{e7/e7}$ genotypes as described (Westerfield, 1995). Grafted hosts were allowed to develop for 14 hr, after which they were screened for the presence of red clones in the spinal cord. Positive chimeras were immediately exposed to 12.5 Gy IR. After fixation (4% PFA, performed at 2.5 hpIR), chimeras were processed for whole-mount TUNEL analysis as described above.

DNA Content Analysis of Zebrafish Embryos

The DNA content of zebrafish embryos was determined by flow cytometric (FCM) analysis of disaggregated embryos treated with propidium iodide (PI) and sodium citrate. Live zebrafish embryos were dechorionated in pronase (2.0 mg/mL in egg water) for 3 to 5 minutes, rinsed 5 times in egg water and then anesthetized in Tricaine (200 µg/mL; 3-amino benzoic acid ethyl ester; Sigma A-5040). Embryos were resuspended in 100 µL of Dubelco's Modified Eagle's Medium (DMEM; Cambrex 12-604F) supplemented with 20% fetal bovine serum (FBS; from Cabmrex 14-502F) in 1.5 mL Eppendorf tubes. Embryos were then disaggregated by rotating and lifting a pestle 20 times with moderate pressure. An additional 900 µL of DMEM/20% FBS was added to each tube. The supernatant was removed after 3 min and passed through a 40 µm mesh (from Small Parts CMN-40-D) into a 15 mL tube. The total volume was raised to 2.5 mL with DMEM, and then to 5 mL with PBS. Tubes were then spun at 2000 rpm for 5 min at room temperature (RT) and the liquid was drained by gently tipping the tube. The pellet was resuspended in 6 mL of PBS and vortexed briefly before recentrifugation at 2000 rpm for 5 min at RT. All liquid was removed by gently tipping the tube and swabbing the walls of the tube with a Q-Tip. The pellet was vortexed gently, and 1 mL of PI solution with Sodium Citrate (0.05 mg/mL PI (Calbiochem 537059) in 0.1% sodium citrate) was added directly onto the pellet. Tubes were stored in the dark at 4° C. for up to 24 hr. 2 µg of RNase Cocktail (Ambion 2286) was added to each tube 30 min before FCM analysis, and incubated at RT in the dark for 30 min. Samples were passed through a 40 µm mesh prior to running the samples.

Drug Treatments of Live Zebrafish Embryos

Immediately before IR, 18-hpf embryos were dechorionated and transferred to fresh egg water containing 1% DMSO, with or without the following inhibitors at indicated final concentrations: KU55933 (10 µM; Sigma) (Hickson et al., 2004); Chk2 Inhibitor II (10 µM; Calbiochem) (Arienti et al., 2005); Gö6976 (1 µM; Calbiochem) (Kohn et al., 2003). Unless stated otherwise, embryos were exposed to the inhibitors for 6 hr, transferred to fresh egg water, rinsed five times for 5 min, and labeled with AO. For experiments with Tg(rag2:EGFP-bcl-2) larvae, larvae were incubated in the inhibitor solution at 4 dpf, irradiated at 5 dpf, rinsed at 6 dpf, incubated in fresh inhibitor for an additional 72 hr, and mounted live at 9 dpf for fluorescence microscopic analysis of EGFP expression.

Antibodies

Figure 22:
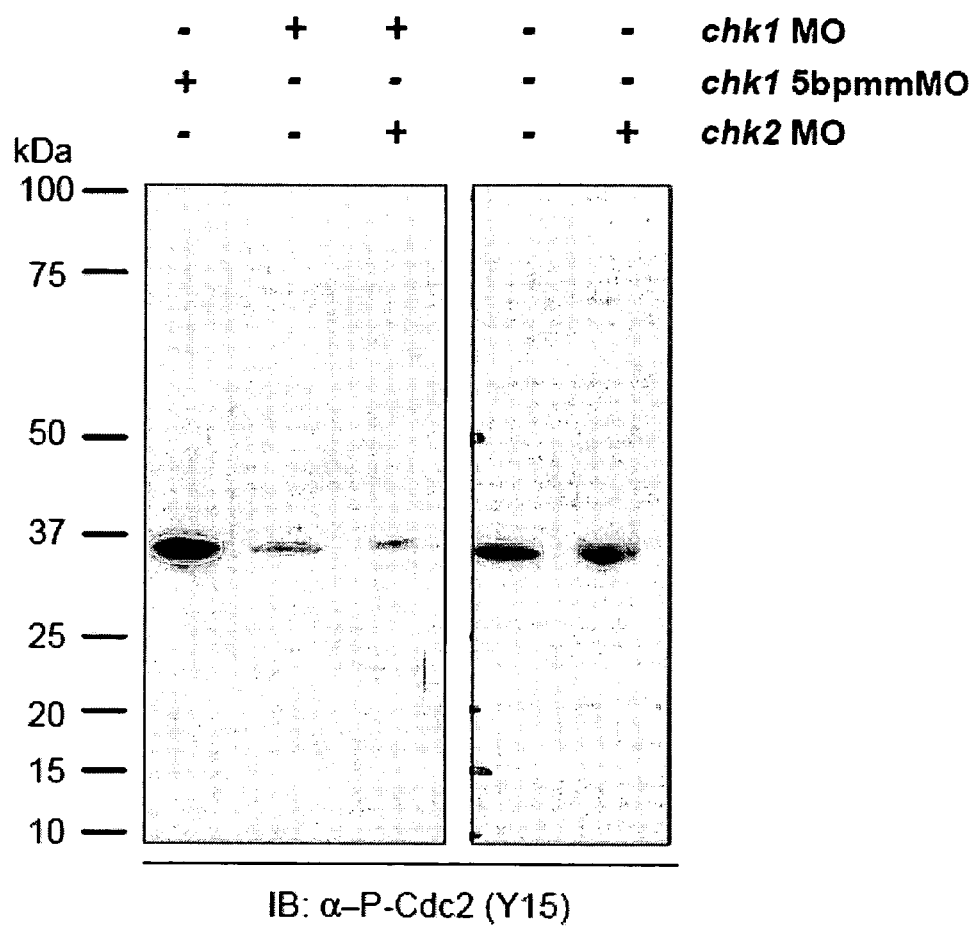
FIG. 22 provides two western blot images, showing phosphorylated Cdc2 levels in zebrafish chk1 morphants. Entire western blots for the anti-P-CDC2 (Y15) immunoblot shown in FIG. 2C. This human antibody detects only one band in zebrafish lysates. This band migrates at the expected molecular weight (37 kDa), demonstrating cross-reactivity.

Antibodies used for immunoblots of zebrafish lysates were rabbit anti-zebrafish Chk1 pAb (Antagene 60B253); rabbit anti-zebrafish protein kinase Chk2 pAb (Antagene 60B318); rabbit anti-human ATR pAb (abcam ab10327); rabbit anti-human caspase-3 pAb (Stressgen AAS-103), used for detecting procaspase-3 on western blots; rabbit anti-phospho-Cdc2 pAb (P-Cdc2, phospho-Tyr15) (abcam ab10533) (see also FIG. 22); and mouse anti-actin mAb (Sigma A5691) (Giraldez et al., 2005). Antibodies used for zebrafish whole mount immunohistochemistry were anti-caspase-3, active form, mAb (rabbit IgG, BD Pharmingen 559565) (Eimon et al., 2006; Kratz et al., 2006); rabbit anti-phospho-Histone-H3 pAb (pH3, P-Ser10) (Santa Cruz SC-8656-R) (Stern et al., 2005); anti-HU mAb (16A11, Molecular Probes) (Giraldez et al., 2005); and AlexaFluor 488 (or 568) conjugated anti-rabbit and anti-mouse IgG. Antibodies used for immunoblots of human cell lysates were rat anti-caspase-2 (ICH-1) mAb (clone 11B4, reactive to both the proform and the p19 subunit, Chemicon MAB3507); mouse anti-caspase-3 mAb, large subunit and proform, clone 4-1-18 (Upstate Cell Signaling Solutions MAB4703); rabbit anti-ATM phospho (ser 1981) and anti-ATM pAbs (Novus Biologicals ab2888 and NB 100-104, respectively); mouse anti-Chk1 (G-4) and anti-Chk2 (A-11) mAbs (Santa Cruz sc-8408 and sc-17747, respectively); rabbit anti-phospho-Chk1 (Ser 317) and anti-phospho-Chk2 (Thr 68) pAbs (Cell Signaling 2344S and 2661S, respectively); rabbit anti-phospho-H2A.X (S139) pAb (Upstate 07-164); rabbit anti-phospho-cdc25C (Ser 216) mAb (63F9, Cell Signaling 4901S); mouse anti-phospho-HSP27 (Ser82) mAb and rabbit anti-HSP27 pAb (Cell Signaling Technology, 2402 and 2401, respectively); anti-P-Cdc2 (see above); mouse anti-p53 (Pab 1801) mAb (Santa-Cruz SC-98); and mouse anti-GAPDH mAb (abcam ab9484).

Preparation of Protein Lysates from Zebrafish Embryos 40 embryos for each experimental condition were chilled on ice for 60 min in egg water and rinsed twice in ice-cold PBST. Embryos were deyolked by mechanical shearing through thin-tip plastic pipettes. All embryos were transferred to a 1.5 mL eppendorf tube, and residual PBST was removed. Lysis buffer (2 µL per embryo) was added to each tube (1% Nonidet P-40, 0.1% SDS, 100 mM NaCl, 50 mM Tris pH 7.4-7.7, 10 mM EDTA, supplemented with complete mini protein inhibitor cocktail (Roche 1836153, 1 tablet/10 mL) and the embryos were homogenized with a pestle. 1 µL of PMSF was then added to each sample before centrifugation at 4° C. and 15,000 rpm for 10 min. The supernatant was transferred to a fresh tube and stored at −80° C. until needed.

Western Blotting

Protein extract (5-60 µg) was added to 4× gel loading buffer and 10× denaturing solution (Invitrogen) in appropriate proportions, and samples were incubated at 70° C. for 10 min. Samples were run at 200V for 1 hr on a 4-12% Bis-tris gradient gel (Invitrogen). After electrophoresis, samples were transferred for 1.5 hr (350 mA) to a Nitrocellulose membrane (Millipore) using a submerged transfer apparatus (Bio-Rad). Membranes were then blocked with 5% milk in Tris-buffered saline with 0.1% tween (TBST) and probed overnight at 4° C. with the following antibodies: anti-zebrafish Chk1 (diluted 1:200), anti-zebrafish Chk2 (1:200), anti-P-Cdc2 (1:1000), anti-actin (1:2000), anti-human ATR (1:500) and Stressgen anti-human-caspase-3 (1:500) for zebrafish immunoblots; and anti-caspase-2 (1:200), Upstate anti-caspase-3 (1:500), anti-P-ATM (1:500), anti-ATM (1:500), Santa Cruz anti-human Chk1 (1:1000), Santa Cruz anti-human Chk2 (1:1000), anti-P-Chk1 (1:500), anti-P-Chk2 (1:500), anti-P-H2A.X (1:2000), anti-P-cdc25C (1:1000), anti-P-HSP27 (1:1000), anti-HSP27 (1:1000), anti-P-Cdc2 (1:1000), anti-p53 (1:1000) and anti-GAPDH (1:5000) for immunoblots of human tumor cell lysates. Detailed references for all primary antibodies can be found in the 'Antibodies' section elsewhere herein.

Membranes were then washed in TBST and probed with anti-rabbit, anti-rat and anti-mouse HRP-linked antibodies (GE Healthcare UK Ltd) at a concentration of 1 in 2000 for 1 hr, washed, and placed in Western Lightening chemiluminescence reagent plus (PerkinElmer Life Science). The band of interest was then identified with photographic film.

Apoptosis and Cell Viability Assays in Cultured Human Cancer Cells

For the Annexin V assay, $2.0\times10^5$ cells treated with IR (0 or 10 Gy) and/or Gö6976 (0 or 1 µM) for 48 h were washed with cold-PBS and resuspended in staining buffer containing propidium iodide (PI) and fluorescein isothiocynate (FITC)-conjugated anti-AnnexinV antibody (MEBCYTO apoptosis kit, MBL international, MA). After 30 min incubation at room temperature, cells were analyzed by flow cytometry (FACScaliber, BD Bioscience, San Jose, Calif.) and CellQuest analysis program (BD Bioscience). The cells in PI-negative and AnnexinV-positive fraction were evaluated as apoptosis. Data were collected from two independent experiments in which each condition (shRNA, presence or absence of Gö6976) was analyzed in triplicate.

TUNEL assays were performed using the APO-BRDU kit (BD Biosciences, Franklin Lakes, N.J., USA) according to the manufacturer's recommendation. Briefly, the cells were fixed with 1% PFA (Sigma-Aldrich) in PBS for 1 h on ice, washed in PBS and incubated with 70% ethanol at −20° C. overnight. The cells were then washed and incubated with DNA labeling solution containing deoxynucleotidyl transferase (TdT) and bromoylated deoxyuridine triphosphates (BrdU) for 4 h at 37° C. The cells were washed, incubated in the staining buffer containing FITC-labeled anti-BrdU antibody for 30 min at room temperature, and a mixture of PI/RNAse was added. After 30 min incubation at room temperature, the cells were analyzed by flow cytometry.

For the cell viability assay, Tg(BCL2)⁻ and Tg(BCL2)⁺ H218 cells were seeded into black 96-well plates (BD Bioscience) at a density of 1000 cells per well on day 1. 24-well sets were treated with DMSO or Gö6976 (1 µM), and plates were exposed to 0 or 10 Gy IR on day 2. After 72 hr, cellular viability was measured with the CellTiter-Glo Luminescent Cell Viability Assay kit (Promega) according to the manufacturer's instructions. Cellular viability for each well was calculated as a percentage of the mean viability of DMSO-treated, non-irradiated cells. The mean cellular viability and SEM were calculated and plotted with GraphPad Prism version 3 (GraphPad Software, San Diego Calif., USA). Each viability experiment was performed twice.

Clonogenic assays were performed as described (Franken et al., 2006). Briefly, the cells were plated in 6-cm dishes, treated with Gö6976 followed by IR and cultured for 2 weeks. The medium was then removed, and the cells were rinsed by PBS and incubated with a mixture of 6.0% glutaraldehyde and 0.5% crystal violet (Sigma-Aldrich, St Louis, Mo., USA) for 30 min at room temperature. The dishes were washed with water, and colonies consisting of at least 50 cells were counted.

REFERENCES

Afshar, G., Jelluma, N., Yang, X., Basila, D., Arvold, N. D., Karlsson, A., Yount, G. L., Damen, T. B., Koller, E., and Haas-Kogan, D. A. (2006). Radiation-induced caspase-8 mediates p53-independent apoptosis in glioma cells. Cancer Res 66, 4223-4232.

Arienti, K. L., Brunmark, A., Axe, F. U., McClure, K., Lee, A., Blevitt, J., Neff, D. K., Huang, L., Crawford, S., Pandit, C. R., et al. (2005). Checkpoint kinase inhibitors: SAR and radioprotective properties of a series of 2-arylbenzimidazoles. J Med Chem 48, 1873-1885.

Bergeron, L., Perez, G. I., Macdonald, G., Shi, L., Sun, Y., Jurisicova, A., Varmuza, S., Latham, K. E., Flaws, J. A., Salter, J. C., et al. (1998). Defects in regulation of apoptosis in caspase-2-deficient mice. Genes Dev 12, 1304-1314.

Berghmans, S., Murphey, R. D., Wienholds, E., Neuberg, D., Kutok, J. L., Fletcher, C. D., Morris, J. P., Liu, T. X., Schulte-Merker, S., Kanki, J. P., et al. (2005). tp53 mutant zebrafish develop malignant peripheral nerve sheath tumors. Proc Natl Acad Sci USA 102, 407-412.

Berman, J. N., Kanki, J. P., and Look, A. T. (2005). Zebrafish as a model for myelopoiesis during embryogenesis. Exp Hematol 33, 997-1006.

Bernassola, F., Oberst, A., Melino, G., and Pandolfi, P. P. (2005). The promyelocytic leukaemia protein tumour suppressor functions as a transcriptional regulator of p63. Oncogene 24, 6982-6986.

Bernassola, F., Salomoni, P., Oberst, A., Di Como, C. J., Pagano, M., Melino, G., and Pandolfi, P. P. (2004). Ubiquitin-dependent degradation of p73 is inhibited by PML. J Exp Med 199, 1545-1557.

Bonzon, C., Bouchier-Hayes, L., Pagliari, L. J., Green, D. R., and Newmeyer, D. D. (2006). Caspase-2-induced apoptosis requires bid cleavage: a physiological role for bid in heat shock-induced death. Mol Biol Cell 17, 2150-2157.

Bunz, F., Dutriaux, A., Lengauer, C., Waldman, T., Zhou, S., Brown, J. P., Sedivy, J. M., Kinzler, K. W., and Vogelstein, B. (1998). Requirement for p53 and p21 to sustain G2 arrest after DNA damage. Science 282, 1497-1501.

Castedo, M., Perfettini, J. L., Roumier, T., Andreau, K., Medema, R., and Kroemer, G. (2004a). Cell death by mitotic catastrophe: a molecular definition. Oncogene 23, 2825-2837.

Castedo, M., Perfettini, J. L., Roumier, T., Yakushijin, K., Horne, D., Medema, R., and Kroemer, G. (2004b). The cell cycle checkpoint kinase Chk2 is a negative regulator of mitotic catastrophe. Oncogene 23, 4353-4361.

Chan, T. A., Hwang, P. M., Hermeking, H., Kinzler, K. W., and Vogelstein, B. (2000). Cooperative effects of genes controlling the G(2)/M checkpoint. Genes Dev 14, 1584-1588.

Chen, Z., Xiao, Z., Chen, J., Ng, S. C., Sowin, T., Sham, H., Rosenberg, S., Fesik, S., and Zhang, H. (2003). Human Chk1 expression is dispensable for somatic cell death and critical for sustaining G2 DNA damage checkpoint. Mol Cancer Ther 2, 543-548.

Chen, Z., Xiao, Z., Gu, W. Z., Xue, J., Bui, M. H., Kovar, P., Li, G., Wang, G., Tao, Z. F., Tong, Y., et al. (2006). Selective Chk1 inhibitors differentially sensitize p53-deficient cancer cells to cancer therapeutics. Int J Cancer 119, 2784-2794.

Colell, A., Ricci, J. E., Tait, S., Milasta, S., Maurer, U., Bouchier-Hayes, L., Fitzgerald, P., Guio-Carrion, A., Waterhouse, N. J., Li, C. W., et al. (2007). GAPDH and autophagy preserve survival after apoptotic cytochrome c release in the absence of caspase activation. Cell 129, 983-997.

Collis, S. J., Swartz, M. J., Nelson, W. G., and DeWeese, T. L. (2003). Enhanced radiation and chemotherapy-mediated cell killing of human cancer cells by small inhibitory RNA silencing of DNA repair factors. Cancer Res 63, 1550-1554.

Eimon, P. M., Kratz, E., Varfolomeev, E., Hymowitz, S. G., Stern, H., Zha, J., and Ashkenazi, A. (2006). Delineation of the cell-extrinsic apoptosis pathway in the zebrafish. Cell Death Differ 13, 1619-1630.

Franken, N. A., Rodermond, H. M., Stap, J., Haveman, J., and van Bree, C. (2006). Clonogenic assay of cells in vitro. Nature protocols 1, 2315-2319.

Frenkel, J., Sherman, D., Fein, A., Schwartz, D., Almog, N., Kapon, A., Goldfinger, N., and Rotter, V. (1999). Accentuated apoptosis in normally developing p53 knockout mouse embryos following genotoxic stress. Oncogene 18, 2901-2907.

Garber, K. (2005). New checkpoint blockers begin human trials. J Natl Cancer Inst 97, 1026-1028.

Giraldez, A. J., Cinalli, R. M., Glasner, M. E., Enright, A. J., Thomson, J. M., Baskerville, S., Hammond, S. M., Bartel, D. P., and Schier, A. F. (2005). MicroRNAs regulate brain morphogenesis in zebrafish. Science 308, 833-838.

Goldstein, J. C., Waterhouse, N. J., Juin, P., Evan, G. I., and Green, D. R. (2000). The coordinate release of cytochrome c during apoptosis is rapid, complete and kinetically invariant. Nat Cell Biol 2, 156-162.

Gong, J. G., Costanzo, A., Yang, H. Q., Melino, G., Kaelin, W. G., Jr., Levrero, M., and Wang, J. Y. (1999). The tyrosine kinase c-Abl regulates p73 in apoptotic response to cisplatin-induced DNA damage. Nature 399, 806-809.

Hengartner, M. O. (2000). The biochemistry of apoptosis. Nature 407, 770-776.

Hickson, I., Zhao, Y., Richardson, C. J., Green, S. J., Martin, N. M., On, A. I., Reaper, P. M., Jackson, S. P., Curtin, N. J., and Smith, G. C. (2004). Identification and characterization of a novel and specific inhibitor of the ataxia-telangiectasia mutated kinase ATM. Cancer Res 64, 9152-9159.

Hsu, K., Traver, D., Kutok, J. L., Hagen, A., Liu, T. X., Paw, B. H., Rhodes, J., Berman, J. N., Zon, L. I., Kanki, J. P., et al. (2004). The pu.1 promoter drives myeloid gene expression in zebrafish. Blood 104, 1291-1297.

Huang, H., Regan, K. M., Lou, Z., Chen, J., and Tindall, D. J. (2006). CDK2-dependent phosphorylation of FOXO1 as an apoptotic response to DNA damage. Science 314, 294-297.

Imamura, S., and Kishi, S. (2005). Molecular cloning and functional characterization of zebrafish ATM. The international journal of biochemistry & cell biology 37, 1105-1116.

Inohara, N., and Nunez, G. (2000). Genes with homology to mammalian apoptosis regulators identified in zebrafish. Cell Death Differ 7, 509-510.

Ishii, N., Maier, D., Merlo, A., Tada, M., Sawamura, Y., Diserens, A. C., and Van Meir, E. G. (1999). Frequent co-alterations of TP53, p16/CDKN2A, p14ARF, PTEN tumor suppressor genes in human glioma cell lines. Brain pathology (Zurich, Switzerland) 9, 469-479.

Kasibhatla, S., Brunner, T., Genestier, L., Echeverri, F., Mahboubi, A., and Green, D. R. (1998). DNA damaging agents induce expression of Fas ligand and subsequent apoptosis in T lymphocytes via the activation of NF-kappa B and AP-1. Mol Cell 1, 543-551.

Kastan, M. B., and Bartek, J. (2004). Cell-cycle checkpoints and cancer. Nature 432, 316-323.

Kawabe, T. (2004). G2 checkpoint abrogators as anticancer drugs. Mol Cancer Ther 3, 513-519.

Kohn, E. A., Yoo, C. J., and Eastman, A. (2003). The protein kinase C inhibitor Go6976 is a potent inhibitor of DNA damage-induced S and G2 cell cycle checkpoints. Cancer Res 63, 31-35.

Kolesnick, R., and Fuks, Z. (2003). Radiation and ceramide-induced apoptosis. Oncogene 22, 5897-5906.

Kratz, E., Eimon, P. M., Mukhyala, K., Stern, H., Zha, J., Strasser, A., Hart, R., and Ashkenazi, A. (2006). Functional characterization of the Bcl-2 gene family in the zebrafish. Cell Death Differ 13, 1631-1640.

Lam, M. H., Liu, Q., Elledge, S. J., and Rosen, J. M. (2004). Chk1 is haploinsufficient for multiple functions critical to tumor suppression. Cancer Cell 6, 45-59.

Langenau, D. M., Jette, C., Berghmans, S., Palomero, T., Kanki, J. P., Kutok, J. L., and Look, A. T. (2005). Suppression of apoptosis by bcl-2 overexpression in lymphoid cells of transgenic zebrafish. Blood 105, 3278-3285.

Langenau, D. M., Traver, D., Ferrando, A. A., Kutok, J. L., Aster, J. C., Kanki, J. P., Lin, S., Prochownik, E., Trede, N. S., Zon, L. I., et al. (2003). Myc-induced T cell leukemia in transgenic zebrafish. Science 299, 887-890.

Langheinrich, U., Hennen, E., Stott, G., and Vacun, G. (2002). Zebrafish as a model organism for the identification and characterization of drugs and genes affecting p53 signaling. Curr Biol 12, 2023-2028.

Lassus, P., Opitz-Araya, X., and Lazebnik, Y. (2002). Requirement for caspase-2 in stress-induced apoptosis before mitochondrial permeabilization. Science 297, 1352-1354.

Li, H., Kolluri, S. K., Gu, J., Dawson, M. I., Cao, X., Hobbs, P. D., Lin, B., Chen, G., Lu, J., Lin, F., et al. (2000). Cytochrome c release and apoptosis induced by mitochondrial targeting of nuclear orphan receptor TR3. Science 289, 1159-1164.

Lin, B., Kolluri, S. K., Lin, F., Liu, W., Han, Y. H., Cao, X., Dawson, M. I., Reed, J. C., and Zhang, X. K. (2004). Conversion of Bcl-2 from protector to killer by interaction with nuclear orphan receptor Nur77/TR3. Cell 116, 527-540.

Liu, Q., Guntuku, S., Cui, X. S., Matsuoka, S., Cortez, D., Tamai, K., Luo, G., Carattini-Rivera, S., DeMayo, F., Bradley, A., et al. (2000). Chk1 is an essential kinase that is regulated by Atr and required for the G(2)/M DNA damage checkpoint. Genes Dev 14, 1448-1459.

Lowe, S. W., Cepero, E., and Evan, G. (2004). Intrinsic tumour suppression. Nature 432, 307-315.

Moffat, J., Grueneberg, D. A., Yang, X., Kim, S. Y., Kloepfer, A. M., Hinkle, G., Piqani, B., Eisenhaure, T. M., Luo, B., Grenier, J. K., et al. (2006). A lentiviral RNAi library for human and mouse genes applied to an arrayed viral high-content screen. Cell 124, 1283-1298.

Mukhopadhyay, U. K., Senderowicz, A. M., and Ferbeyre, G. (2005). RNA silencing of checkpoint regulators sensitizes p53-defective prostate cancer cells to chemotherapy while sparing normal cells. Cancer Res 65, 2872-2881.

Nutt, L. K., Margolis, S. S., Jensen, M., Herman, C. E., Dunphy, W. G., Rathmell, J. C., and Kornbluth, S. (2005). Metabolic regulation of oocyte cell death through the CaMKII-mediated phosphorylation of caspase-2. Cell 123, 89-103.

Okada, H., and Mak, T. W. (2004). Pathways of apoptotic and non-apoptotic death in tumour cells. Nat Rev Cancer 4, 592-603.

Pyati, U. J., Look, A. T., and Hammerschmidt, M. (2006). Zebrafish as a powerful vertebrate model system for in vivo studies of cell death. Semin Cancer Biol.

Reinhardt, H. C., Aslanian, A. S., Lees, J. A., and Yaffe, M. B. (2007). p53-deficient cells rely on ATM- and ATR-mediated checkpoint signaling through the p38MAPK/MK2 pathway for survival after DNA damage. Cancer Cell 11, 175-189.

Rentzsch, F., Kramer, C., and Hammerschmidt, M. (2003). Specific and conserved roles of TAp73 during zebrafish development. Gene 323, 19-30.

Rhodes, J., Hagen, A., Hsu, K., Deng, M., Liu, T. X., Look, A. T., and Kanki, J. P. (2005). Interplay of pu.1 and gata1 determines myelo-erythroid progenitor cell fate in zebrafish. Dev Cell 8, 97-108.

Roninson, I. B., Broude, E. V., and Chang, B. D. (2001). If not apoptosis, then what? Treatment-induced senescence and mitotic catastrophe in tumor cells. Drug Resist Updat 4, 303-313.

Roos, W. P., and Kaina, B. (2006). DNA damage-induced cell death by apoptosis. Trends Mol Med 12, 440-450.

Shin, S., Lee, Y., Kim, W., Ko, H., Choi, H., and Kim, K. (2005). Caspase-2 primes cancer cells for TRAIL-mediated apoptosis by processing procaspase-8. Embo J 24, 3532-3542.

Stern, H. M., Murphey, R. D., Shepard, J. L., Amatruda, J. F., Straub, C. T., Pfaff, K. L., Weber, G., Tallarico, J. A., King, R. W., and Zon, L. I. (2005). Small molecules that delay S phase suppress a zebrafish bmyb mutant. Nat Chem Biol 1, 366-370.

Syljuasen, R. G., Sorensen, C. S., Nylandsted, J., Lukas, C., Lukas, J., and Bartek, J. (2004). Inhibition of Chk1 by CEP-3891 accelerates mitotic nuclear fragmentation in response to ionizing Radiation. Cancer Res 64, 9035-9040.

Tinel, A., and Tschopp, J. (2004). The PIDDosome, a protein complex implicated in activation of caspase-2 in response to genotoxic stress. Science 304, 843-846.

Troy, C. M., and Shelanski, M. L. (2003). Caspase-2 redux. Cell Death Differ 10, 101-107.

Tse, A. N., Carvajal, R., and Schwartz, G. K. (2007). Targeting checkpoint kinase 1 in cancer therapeutics. Clin Cancer Res 13, 1955-1960.

Tu, S., McStay, G. P., Boucher, L. M., Mak, T., Beere, H. M., and Green, D. R. (2006). In situ trapping of activated initiator caspases reveals a role for caspase-2 in heat shock-induced apoptosis. Nat Cell Biol 8, 72-77.

Urist, M., Tanaka, T., Poyurovsky, M. V., and Prives, C. (2004). p73 induction after DNA damage is regulated by checkpoint kinases Chk1 and Chk2. Genes Dev 18, 3041-3054.

Vousden, K. H., and Lu, X. (2002). Live or let die: the cell's response to p53. Nat Rev Cancer 2, 594-604.

Wagner, K. W., Engels, I. H., and Deveraux, Q. L. (2004). Caspase-2 can function upstream of bid cleavage in the TRAIL apoptosis pathway. J Biol Chem 279, 35047-35052.

Wang, X., Kennedy, R. D., Ray, K., Stuckert, P., Ellenberger, T., and D'Andrea, A. D. (2007). Chk1-mediated phosphorylation of FANCE is required for the Fanconi anemia/BRCA pathway. Mol Cell Biol 27, 3098-3108.

Westerfield, M., Doerry, E., Kirkpatrick, A. E., Driever, W., and Douglas, S. A. (1997). An on-line database for zebrafish development and genetics research. Seminars in Cell and Developmental Biology 8, 477-488.

Wichmann, A., Jaklevic, B., and Su, T. T. (2006). Ionizing radiation induces caspase-dependent but Chk2- and p53-independent cell death in *Drosophila melanogaster*. Proc Natl Acad Sci USA 103, 9952-9957.

Wyllie, A. H., Kerr, J. F., and Currie, A. R. (1980). Cell death: the significance of apoptosis. International review of cytology 68, 251-306.

Xiao, Z., Xue, J., Sowin, T. J., Rosenberg, S. H., and Zhang, H. (2005). A novel mechanism of checkpoint abrogation conferred by Chk1 downregulation. Oncogene 24, 1403-1411.

Yang, H. W., Kutok, J. L., Lee, N. H., Piao, H. Y., Fletcher, C. D., Kanki, J. P., and Look, A. T. (2004). Targeted expression of human MYCN selectively causes pancreatic neuroendocrine tumors in transgenic zebrafish. Cancer Res 64, 7256-7262.

Yount, G. L., Afshar, G., Ries, S., Korn, M., Shalev, N., Basila, D., McCormick, F., and Haas-Kogan, D. A. (2001). Transcriptional activation of TRADD mediates p53-independent radiation-induced apoptosis of glioma cells. Oncogene 20, 2826-2835.

Yuan, Z. M., Shioya, H., Ishiko, T., Sun, X., Gu, J., Huang, Y. Y., Lu, H., Kharbanda, S., Weichselbaum, R., and Kufe, D. (1999). p73 is regulated by tyrosine kinase c-Abl in the apoptotic response to DNA damage. Nature 399, 814-817.

Zachos, G., Rainey, M. D., and Gillespie, D. A. (2003). Chk1-deficient tumour cells are viable but exhibit multiple checkpoint and survival defects. Embo J 22, 713-723.

Zhivotovsky, B., and Orrenius, S. (2005). Caspase-2 function in response to DNA damage. Biochem Biophys Res Commun 331, 859-867.

Zhou, B. B., and Bartek, J. (2004). Targeting the checkpoint kinases: chemosensitization versus chemoprotection. Nat Rev Cancer 4, 216-225.

Zhou, B. B., and Elledge, S. J. (2000). The DNA damage response: putting checkpoints in perspective. Nature 408, 433-439.

Other aspects of the invention will be clear to the skilled artisan and need not be repeated here. Each reference cited herein is incorporated by reference in its entirety.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

The invention claimed is:

1. A method for determining whether a subject having a cancer is a candidate for a Chk1 inhibitor-based cancer treatment regimen, comprising:
   contacting cancer cells of the subject with a Chk1 inhibitor, in conjunction with a genotoxic stress, and then determining caspase-2 activation in the cancer cells,
   wherein if there is caspase-2 activation in the cancer cells, then the subject is identified as a candidate for a Chk1 inhibitor-based cancer treatment regimen.

2. The method of claim 1, wherein the cancer cells are contacted with the Chk1 inhibitor, in conjunction with a genotoxic stress, in vivo.

3. The method of claim 2, wherein caspase-2 activation is determined by
   comparing a first level of caspase-2 activity determined in the cancer cells after the cancer cells are contacted with the Chk1 inhibitor, in conjunction with the genotoxic stress to a second level of caspase-2 activity determined in control cells,
   wherein if the first level of caspase-2 activity is greater than the second level of caspase-2 activity, then there is caspase-2 activation.

4. The method of claim 3, wherein the control cells are selected from the group consisting of: Hela cells, Jurkat cells, HCT116 colon carcinoma cells, SAOS2 osteosarcoma, the MDA-MB-435 breast cancer cells, and LN-428 glioblastoma cells.

5. The method of claim 3, wherein the control cells are a sample of cancer cells obtained from the subject before contacting in vivo the cancer cells with the Chk1 inhibitor in conjunction with a genotoxic stress.

6. The method of claim 2, wherein the genotoxic stress is a chemotherapy, a radiotherapy or combination thereof.

7. The method of claim 1, wherein the cancer cells are a first sample of cancer cells obtained from the subject and contacted with the Chk1 inhibitor, in conjunction with a genotoxic stress, ex vivo or in vitro.

8. The method of claim 7, wherein the caspase-2 activation is determined by:
   comparing a first level of caspase-2 activity determined in the first sample of cancer cells after the first sample of cancer cells is contacted with the Chk1 inhibitor, in conjunction with the genotoxic stress to a second level of caspase-2 activity in determined in control cells,
   wherein if the first level of caspase-2 activity is greater than the second level of caspase-2 activity, then there is caspase-2 activation.

9. The method of claim 8, wherein the control cells are selected from the group consisting of: Hela cells, Jurkat cells, HCT116 colon carcinoma cells, SAOS2 osteosarcoma, the MDA-MB-435 breast cancer cells, and LN-428 glioblastoma cells.

10. The method of claim 8, wherein the control cells are a second sample of cancer cells obtained from the subject and not contacted with the Chk1 inhibitor.

\* \* \* \* \*